US009296813B2

(12) United States Patent
Shulok et al.

(10) Patent No.: US 9,296,813 B2
(45) **Date of Patent: *Mar. 29, 2016**

(54) COMPOSITIONS AND METHODS OF USE FOR ANTIBODIES OF DICKKOPF-1

(71) Applicants: Janine R. Shulok, Newton, MA (US); Feng Cong, Quincy, MA (US); Mark C. Fishman, Newton Center, MA (US); Seth Ettenberg, Melrose, MA (US); Michael Bardroff, Munich (DE); Mariel Donzeau, Strasbourg (FR); Stefanie Urlinger, Nürnberg (DE)

(72) Inventors: Janine R. Shulok, Newton, MA (US); Feng Cong, Quincy, MA (US); Mark C. Fishman, Newton Center, MA (US); Seth Ettenberg, Melrose, MA (US); Michael Bardroff, Munich (DE); Mariel Donzeau, Strasbourg (FR); Stefanie Urlinger, Nürnberg (DE)

(73) Assignee: NOVARTIS AG, Basel (CH)

( * ) Notice: Subject to any disclaimer, the term of this patent is extended or adjusted under 35 U.S.C. 154(b) by 283 days.

This patent is subject to a terminal disclaimer.

(21) Appl. No.: 14/178,892

(22) Filed: Feb. 12, 2014

(65) Prior Publication Data

US 2014/0170147 A1 Jun. 19, 2014

Related U.S. Application Data

(62) Division of application No. 14/163,230, filed on Jan. 24, 2014, which is a division of application No. 12/160,875, filed on Sep. 23, 2011, now Pat. No. 8,673,306.

(60) Provisional application No. 60/759,216, filed on Jan. 13, 2006.

(51) Int. Cl.

| | |
|---|---|
| ***A61K 39/395*** | (2006.01) |
| ***C07K 16/22*** | (2006.01) |
| ***C07K 16/18*** | (2006.01) |
| ***A61K 31/675*** | (2006.01) |
| ***A61K 45/06*** | (2006.01) |
| *A61K 39/00* | (2006.01) |

(52) U.S. Cl.

CPC ............... *C07K 16/22* (2013.01); *A61K 31/675* (2013.01); *A61K 39/3955* (2013.01); *A61K 45/06* (2013.01); *C07K 16/18* (2013.01); *A61K 2039/505* (2013.01); *C07K 2317/21* (2013.01); *C07K 2317/55* (2013.01); *C07K 2317/565* (2013.01); *C07K 2317/567* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 6,682,736 | B1 | 1/2004 | Hanson et al. |
| 6,951,921 | B2 | 10/2005 | Ferrara et al. |
| 7,037,498 | B2 | 5/2006 | Cohen et al. |
| 7,807,155 | B2 | 10/2010 | Dipadova et al. |
| 2004/0137489 | A1 | 7/2004 | Shaughnessy |
| 2005/0069915 | A1 | 3/2005 | McCarthy et al. |
| 2005/0084494 | A1 | 4/2005 | Prockop et al. |

FOREIGN PATENT DOCUMENTS

| | | | |
|---|---|---|---|
| WO | WO95/24481 | A1 | 9/1995 |
| WO | WO98/46755 | A1 | 10/1998 |
| WO | WO00/06714 | A1 | 2/2000 |
| WO | WO00/18914 | A2 | 4/2000 |
| WO | WO02/086085 | A2 | 10/2001 |
| WO | WO02/066509 | A2 | 8/2002 |
| WO | WO03/053215 | A2 | 7/2003 |
| WO | WO03/070760 | A2 | 8/2003 |
| WO | WO2004/053063 | A2 | 6/2004 |
| WO | WO2006/017538 | A2 | 2/2006 |
| WO | WO2006/100582 | A1 | 9/2006 |
| WO | WO2007/054816 | A2 | 5/2007 |

OTHER PUBLICATIONS

Balint et al., "Antibody Engineering by Parsimonious Mutagenesis" Gene 137(1):109-118, 1993.

Davies et al., "Affinity Improvement of Single Antibody VH Domains: Residues in all Three Hypervariable Regions Affect Antigen Binding" Immunotechnology 2(3):169-179, 1996.

Holt et al., "Domain Antibodies: Proteins for Therapy" Trends in Biotechnology 21(11):484-490, Nov. 2003.

Little et al., "Of Mice and Men: Hybridoma and Recombinant Antibodies" Immunology Today 21(8):364-370, 2000.

Qing et al., "DKK-1 is a widely expressed, potent tumor-associated antigen in multiple myeloma recognized by cytotoxic T lymphocytes" Blood 106(11):976A, 2005.

Fedi et al., "Isolation and Biochemical Characterization of the Human Dkk-1 Homologue, a Novel Inhibitor of Mammalian Wnt Signaling", The Journal of Biological Chemistry 274(27):19465-19472, 1999.

Boyden et al., "High Bone Density Due to a Mutation in LDL-Receptor—Related Protein 5" The New England Journal of Medicine 346(20):1513-1521, 2002.

Tian et al., "The Role of the Wnt-Signaling Antagonist DKK1 in the Development of Osteolytic Lesions in Multiple Myeloma" The New England Journal of Medicine 349(26):2483-2494, 2003.

Morvan et al., "Deletion of a Single Allele of the Dkk1 Gene Leads to an Increase in Bone Formation and Bone Mass", Journal of Bone and Mineral Research 21(6):934-945, 2006.

(Continued)

*Primary Examiner* — Sharon Wen

(74) *Attorney, Agent, or Firm* — John Prince

(57) ABSTRACT

Antibodies and fragments that bind to the protein target Dickkopf (DKK1) are provided, as are methods of use and kits, for treating a target cell, in particular, a cell associated with an osteolytic condition.

19 Claims, 10 Drawing Sheets

(56) References Cited

OTHER PUBLICATIONS

Glinka et al., "Dickkopf-1 is a member of a new family of secreted proteins and functions in head induction" Nature 391(22):357-362, 1998.
Niehrs et al., "Function and biological roles of the Dickkopf family of Wnt modulators" Oncagene 25:7469-7481, 2006.
Rudikoff et al., "Single Amino Acid Substitution Altering Antigen-Binding Specificity" Proc Natl Acad Sci USA 79:1979-1983 Mar. 1982.
MacCallum et al., "Antibody-Antigen Interactions: Contact Analysis and Binding Site Topography" Journal of Molecular Biology 262:732-745, Oct. 11, 1996.
Pascalis et al., "Grafting of 'Abbreviated' Complementarity-Determining Regions Containing Specificity-Determining Residues Essential for Ligand Contact to Engineer a Less Immunogenic Humanized Monoclonal Antibody" The Journal of Immunology 169:3076-3084, 2002.
Casset et al., Biochemical and Biophysical Research Communication A Peptide Mimetic of an Anti-CD4 Monoclonal Antibody by Rational Design 307:198-205, 2003.
Vajdos et al., "Comprehensive Functional Maps of the Antigen-binding Site of an Anti-ErbB2 Antibody Obtained with Shotgun Scanning Mutagenesis" J. Molecular Biology 320(2):415-428, Jul. 5, 2002.
Chen et al. "Selection and Analysis of an Optimized Anti-VEGF Antibody: Crystal Struction of an Affinity-Matured Fab in Complex with Antigen" J. Mol. Biol. 293:865-881, 1999.
Wu et al., Humanization of a Murine Monoclonal Antibody by Simultaneous Optimization of Framework and CDR Residues J. Mol. Biol. 294:151-162, 1999.
Padlan et al., "Structure of an antibody-antigen complex: crystal structure of the HyHEL-10 Fab-lysozyme complex" Proc. Natl. Acad. Sci. 86(15):5938-5942, 1989.
Lamminmaki et al., "Crystal Structure of a Recombinant Anti-estradiol Fab Fragment in Complex with 17β-Estradiol" Journal Biological Chemistry 276(39):36687-36694, Sep. 28, 2001.
Aung et al., "Systematic Search for Gastric Cancer-Specific Genes Based on SAGE Data: Melanoma Inhibitory Activity . . . " Oncogene, 25:2546-2557, 2006.
Caricasole et al. "Induction of Dickkopf-1, a Negative Modulator of the Wnt Pathway, is Associated with Neuronal Degeneration in Alzheimer's Brain"; J. Neurosci.; 24(26):6021-6027, 2004.
Kuhnert et al. "Essential requirement for Wnt signaling in proliferation of adult small intestine and colon revealed by adenoviral expression ofDickkopf-1"; PNAS; 101(1):266-271, 2004.
Lee et al.; "A Potential Role for Dkk-1 in the Pathogenesis of Osteosarcoma Predicts Novel Diagnostic and Treatment Strategies"; British Journal of Cancer 97:1552-1559, 2007.
Qin et al.; "Proliferation and Migration Mediated by Dkk-1/Wnt/beta-catenin Cascade in a Model of Hepatocellular Carcinoma Cells"; Translational Research 150(5):281-294, 2007.
Yaccoby et al., "Antibody-Based Inhibition of DKK1 Suppresses Tumor-Induced Bone Resorption and Multiple Myeloma Growth in vivo" Blood 109(5):2106-2111, 2007.
Portolano et al., "Lack of Promiscuity in Autoantigen-Specific H and L Chain Combinations as Revealed by Human H and L Chain 'Roulette'" J. Immunol. 150:880-887 1993.
Clackson et al., "Making Antibody Fragments using Phage Display Libraries" Nature 352:624-628 (1991).
USPTO News: Biotechnology Art Group Discusses Enablement of Antibody Claims, by Christopher P. Singer, Jun. 14, 2007.
Larry R. Helms, Enablement Issues in the Examination of Antibodies, SPE, 2007.

A.

B.

| $K_a$ (1/Ms) | $K_d$ (1/s) | $K_D$ (M) |
|---|---|---|
| $4.6 \times 10^6$ (±0.4) | $9.0 \times 10^{-6}$ (±2.6) | $2.0 \times 10^{-12}$ (±0.7) |

SEQUENCE LISTING

```
<160> NUMBER OF SEQ ID NOS: 136

<210> SEQ ID NO 1
<211> LENGTH: 266
<212> TYPE: PRT
<213> ORGANISM: Homo sapiens

<400> SEQUENCE: 1

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125
```

```
Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265


<210> SEQ ID NO 2
<211> LENGTH: 124
<212> TYPE: PRT
<213> ORGANISM: Homo sapiens

<400> SEQUENCE: 2

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Leu His Trp Val Arg Gln Ala Pro Gly Lys Gly Leu Glu Trp Val
        35                  40                  45

Ser Ser Ile Ser Tyr Tyr Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser His Met Asp Lys Pro Pro Gly Tyr Val Phe Ala
            100                 105                 110

Phe Trp Gly Gln Gly Thr Leu Val Thr Val Ser Ser
        115                 120


<210> SEQ ID NO 3
<211> LENGTH: 114
<212> TYPE: PRT
<213> ORGANISM: Homo sapiens

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Ser Tyr Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Met Asp His Trp Gly Gln Gly Thr Leu Val Thr Val
            100                 105                 110

Ser Ser


<210> SEQ ID NO 4
<211> LENGTH: 115
<212> TYPE: PRT
<213> ORGANISM: Homo sapiens

<400> SEQUENCE: 4

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Gly Met Thr Trp Val Arg Gln Ala Pro Gly Lys Gly Leu Glu Trp Val
        35                  40                  45

Ser Gly Ile Ser Gly Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ile Tyr Met Asp Tyr Trp Gly Gln Gly Thr Leu Val Thr
            100                 105                 110

Val Ser Ser
        115


<210> SEQ ID NO 5
<211> LENGTH: 116
<212> TYPE: PRT
<213> ORGANISM: Homo sapiens

<400> SEQUENCE: 5

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Ile Asp Leu Asp Tyr Trp Gly Gln Gly Thr Leu Val
            100                 105                 110

Thr Val Ser Ser
        115


<210> SEQ ID NO 6
<211> LENGTH: 116
<212> TYPE: PRT
```

<213> ORGANISM: Homo sapiens

<400> SEQUENCE: 6

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ser Val Ile Ser Ser Asp Ser Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Gly Ile Asp Phe Asp His Trp Gly Gln Gly Thr Leu Val
100 105 110

Thr Val Ser Ser
115

<210> SEQ ID NO 7
<211> LENGTH: 120
<212> TYPE: PRT
<213> ORGANISM: Homo sapiens

<400> SEQUENCE: 7

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Tyr Ile Gly Trp Val Arg Gln Met Pro Gly Lys Gly Leu Glu Trp Met
35 40 45

Gly Ile Ile Tyr Pro Thr Asp Ser Tyr Thr Asn Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Ile Pro Phe Arg Met Arg Gly Phe Asp Tyr Trp Gly Gln
100 105 110

Gly Thr Leu Val Thr Val Ser Ser
115 120

<210> SEQ ID NO 8
<211> LENGTH: 115
<212> TYPE: PRT
<213> ORGANISM: Homo sapiens

<400> SEQUENCE: 8

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Gly Met Thr Trp Val Arg Gln Ala Pro Gly Lys Gly Leu Glu Trp Val
35 40 45

Ser Gly Ile Ser Gly Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Ile Tyr Met Asp Tyr Trp Gly Gln Gly Thr Leu Val Thr
100 105 110

Val Ser Ser
115

<210> SEQ ID NO 9
<211> LENGTH: 115
<212> TYPE: PRT
<213> ORGANISM: Homo sapiens

<400> SEQUENCE: 9

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Gly Met Thr Trp Val Arg Gln Ala Pro Gly Lys Gly Leu Glu Trp Val
35 40 45

Ser Gly Ile Ser Gly Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Ile Tyr Met Asp Tyr Trp Gly Gln Gly Thr Leu Val Thr
100 105 110

Val Ser Ser
115

<210> SEQ ID NO 10
<211> LENGTH: 115
<212> TYPE: PRT
<213> ORGANISM: Homo sapiens

<400> SEQUENCE: 10

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Gly Met Thr Trp Val Arg Gln Ala Pro Gly Lys Gly Leu Glu Trp Val
35 40 45

Ser Gly Ile Ser Gly Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Ile Tyr Met Asp Tyr Trp Gly Gln Gly Thr Leu Val Thr
100 105 110

Val Ser Ser
115

<210> SEQ ID NO 11

-continued

<211> LENGTH: 116
<212> TYPE: PRT
<213> ORGANISM: Homo sapiens

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Ile Asp Leu Asp Tyr Trp Gly Gln Gly Thr Leu Val
            100                 105                 110

Thr Val Ser Ser
        115

<210> SEQ ID NO 12
<211> LENGTH: 116
<212> TYPE: PRT
<213> ORGANISM: Homo sapiens

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Ile Asp Leu Asp Tyr Trp Gly Gln Gly Thr Leu Val
            100                 105                 110

Thr Val Ser Ser
        115

<210> SEQ ID NO 13
<211> LENGTH: 116
<212> TYPE: PRT
<213> ORGANISM: Homo sapiens

<400> SEQUENCE: 13

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

```
Ser Gly Ile Ser Tyr Ser Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Ile Asp Leu Asp Tyr Trp Gly Gln Gly Thr Leu Val
            100                 105                 110

Thr Val Ser Ser
        115


<210> SEQ ID NO 14
<211> LENGTH: 116
<212> TYPE: PRT
<213> ORGANISM: Homo sapiens

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Val Ile Ser Ser Asp Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Ile Asp Phe Asp His Trp Gly Gln Gly Thr Leu Val
            100                 105                 110

Thr Val Ser Ser
        115


<210> SEQ ID NO 15
<211> LENGTH: 118
<212> TYPE: PRT
<213> ORGANISM: Homo sapiens

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ser Ile Glu His Lys Asp Ala Gly Tyr Thr Thr Trp Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Ile Asp Phe Asp His Trp Gly Gln Gly Thr
            100                 105                 110

Leu Val Thr Val Ser Ser
        115
```

<210> SEQ ID NO 16
<211> LENGTH: 116
<212> TYPE: PRT
<213> ORGANISM: Homo sapiens

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Val Ile Ser Ser Asp Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Ile Asp Phe Asp His Trp Gly Gln Gly Thr Leu Val
            100                 105                 110

Thr Val Ser Ser
        115
```

<210> SEQ ID NO 17
<211> LENGTH: 116
<212> TYPE: PRT
<213> ORGANISM: Homo sapiens

<400> SEQUENCE: 17

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Val Ile Ser Ser Asp Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Ile Asp Phe Asp His Trp Gly Gln Gly Thr Leu Val
            100                 105                 110

Thr Val Ser Ser
        115
```

<210> SEQ ID NO 18
<211> LENGTH: 118
<212> TYPE: PRT
<213> ORGANISM: Homo sapiens

<400> SEQUENCE: 18

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
```

-continued 35 40 45

Ser Val Ile Glu His Lys Asp Lys Gly Gly Thr Thr Tyr Tyr Ala Ala
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg His Gly Ile Asp Phe Asp His Trp Gly Gln Gly Thr
100 105 110

Leu Val Thr Val Ser Ser
115

<210> SEQ ID NO 19
<211> LENGTH: 120
<212> TYPE: PRT
<213> ORGANISM: Homo sapiens

<400> SEQUENCE: 19

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Tyr Ile Gly Trp Val Arg Gln Met Pro Gly Lys Gly Leu Glu Trp Met
35 40 45

Gly Ile Ile Val Pro Gly Thr Ser Tyr Thr Ile Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Ile Pro Phe Arg Met Arg Gly Phe Asp Tyr Trp Gly Gln
100 105 110

Gly Thr Leu Val Thr Val Ser Ser
115 120

<210> SEQ ID NO 20
<211> LENGTH: 115
<212> TYPE: PRT
<213> ORGANISM: Homo sapiens

<400> SEQUENCE: 20

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Gly Met Thr Trp Val Arg Gln Ala Pro Gly Lys Gly Leu Glu Trp Val
35 40 45

Ser Gly Ile Ser Gly Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Ile Tyr Met Asp Tyr Trp Gly Gln Gly Thr Leu Val Thr
100 105 110

Val Ser Ser

115

<210> SEQ ID NO 21
<211> LENGTH: 109
<212> TYPE: PRT
<213> ORGANISM: Homo sapiens

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Lys Asn Tyr
            20                  25                  30

Leu Asn Trp Tyr Gln Gln Lys Pro Gly Lys Ala Pro Lys Leu Leu Ile
        35                  40                  45

Gly Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Gly Met Pro Pro
                85                  90                  95

Thr Phe Gly Gln Gly Thr Lys Val Glu Ile Lys Arg Thr
            100                 105
```

<210> SEQ ID NO 22
<211> LENGTH: 109
<212> TYPE: PRT
<213> ORGANISM: Homo sapiens

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu His Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asp Ser Ile Pro Met
                85                  90                  95

Thr Phe Gly Gln Gly Thr Lys Val Glu Ile Lys Arg Thr
            100                 105
```

<210> SEQ ID NO 23
<211> LENGTH: 110
<212> TYPE: PRT
<213> ORGANISM: Homo sapiens

<400> SEQUENCE: 23

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60
```

```
Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Gly Asp Glu Pro
                85                  90                  95

Ile Thr Phe Gly Gln Gly Thr Lys Val Glu Ile Lys Arg Thr
            100                 105                 110


<210> SEQ ID NO 24
<211> LENGTH: 112
<212> TYPE: PRT
<213> ORGANISM: Homo sapiens

<400> SEQUENCE: 24

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile His Asp Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Trp Asp Met Thr
                85                  90                  95

Val Asp Phe Val Phe Gly Gly Gly Thr Lys Leu Thr Val Leu Gly Gln
            100                 105                 110


<210> SEQ ID NO 25
<211> LENGTH: 113
<212> TYPE: PRT
<213> ORGANISM: Homo sapiens

<400> SEQUENCE: 25

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Ser Gly
                85                  90                  95

Asn Thr Lys Val Val Phe Gly Gly Gly Thr Lys Leu Thr Val Leu Gly
            100                 105                 110

Gln


<210> SEQ ID NO 26
<211> LENGTH: 112
<212> TYPE: PRT
<213> ORGANISM: Homo sapiens

<400> SEQUENCE: 26

Asp Ile Val Leu Thr Gln Pro Pro Ser Val Ser Gly Ala Pro Gly Gln
```

-continued

```
1               5                   10                  15

Arg Val Thr Ile Ser Cys Ser Gly Ser Ser Ser Asn Ile Gly Ser Ser
            20                  25                  30

Phe Val Asn Trp Tyr Gln Gln Leu Pro Gly Thr Ala Pro Lys Leu Leu
        35                  40                  45

Ile Gly Asn Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Ser Phe Asp Met Gly Ser
                85                  90                  95

Pro Asn Val Val Phe Gly Gly Gly Thr Lys Leu Thr Val Leu Gly Gln
            100                 105                 110


<210> SEQ ID NO 27
<211> LENGTH: 110
<212> TYPE: PRT
<213> ORGANISM: Homo sapiens

<400> SEQUENCE: 27

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Leu Ser Leu Pro
                85                  90                  95

Thr Thr Phe Gly Gln Gly Thr Lys Val Glu Ile Lys Arg Thr
            100                 105                 110


<210> SEQ ID NO 28
<211> LENGTH: 110
<212> TYPE: PRT
<213> ORGANISM: Homo sapiens

<400> SEQUENCE: 28

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Met Thr Leu Pro
                85                  90                  95

Leu Thr Phe Gly Gln Gly Thr Lys Val Glu Ile Asn Arg Thr
            100                 105                 110
```

<210> SEQ ID NO 29
<211> LENGTH: 110
<212> TYPE: PRT
<213> ORGANISM: Homo sapiens

<400> SEQUENCE: 29

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Leu Thr Leu Pro
                85                  90                  95

Leu Thr Phe Gly Gln Gly Thr Lys Val Glu Ile Lys Arg Thr
            100                 105                 110
```

<210> SEQ ID NO 30
<211> LENGTH: 113
<212> TYPE: PRT
<213> ORGANISM: Homo sapiens

<400> SEQUENCE: 30

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile His Asp Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Val Ser
                85                  90                  95

Pro Ile Thr Ala Val Phe Gly Gly Gly Thr Lys Leu Thr Val Leu Gly
            100                 105                 110

Gln
```

<210> SEQ ID NO 31
<211> LENGTH: 113
<212> TYPE: PRT
<213> ORGANISM: Homo sapiens

<400> SEQUENCE: 31

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile His Asp Gly Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Trp Ala Thr Ser
                85                  90                  95

Pro Leu Ser Ser Val Phe Gly Gly Gly Thr Lys Leu Thr Val Leu Gly
            100                 105                 110

Gln


<210> SEQ ID NO 32
<211> LENGTH: 112
<212> TYPE: PRT
<213> ORGANISM: Homo sapiens

<400> SEQUENCE: 32

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile His Asp Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Trp Asp Ser Leu
                85                  90                  95

Ser Phe Phe Val Phe Gly Gly Gly Thr Lys Leu Thr Val Leu Gly Gln
            100                 105                 110


<210> SEQ ID NO 33
<211> LENGTH: 113
<212> TYPE: PRT
<213> ORGANISM: Homo sapiens

<400> SEQUENCE: 33

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Thr Tyr Thr
                85                  90                  95

Pro Ile Ser Pro Val Phe Gly Gly Gly Thr Lys Leu Thr Val Leu Gly
            100                 105                 110

Gln


<210> SEQ ID NO 34
<211> LENGTH: 113
<212> TYPE: PRT
<213> ORGANISM: Homo sapiens

<400> SEQUENCE: 34
```

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Ser Gly
                85                  90                  95

Asn Thr Lys Val Val Phe Gly Gly Gly Thr Lys Leu Thr Val Leu Gly
            100                 105                 110

Gln


<210> SEQ ID NO 35
<211> LENGTH: 113
<212> TYPE: PRT
<213> ORGANISM: Homo sapiens

<400> SEQUENCE: 35

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Tyr Asp Gln Ile
                85                  90                  95

Lys Leu Ser Ala Val Phe Gly Gly Gly Thr Lys Leu Thr Val Leu Gly
            100                 105                 110

Gln


<210> SEQ ID NO 36
<211> LENGTH: 113
<212> TYPE: PRT
<213> ORGANISM: Homo sapiens

<400> SEQUENCE: 36

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Pro
                85                  90                  95
```

```
Thr Asp Ser Val Val Phe Gly Gly Gly Thr Lys Leu Thr Val Leu Gly
            100                 105                 110

Gln


<210> SEQ ID NO 37
<211> LENGTH: 113
<212> TYPE: PRT
<213> ORGANISM: Homo sapiens

<400> SEQUENCE: 37

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Ser Gly
                85                  90                  95

Asn Thr Lys Val Val Phe Gly Gly Gly Thr Lys Leu Thr Val Leu Gly
            100                 105                 110

Gln


<210> SEQ ID NO 38
<211> LENGTH: 112
<212> TYPE: PRT
<213> ORGANISM: Homo sapiens

<400> SEQUENCE: 38

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Ser
            20                  25                  30

Phe Val Asn Trp Tyr Gln Gln Leu Pro Gly Thr Ala Pro Lys Leu Leu
        35                  40                  45

Ile Gly Asn Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Ser Phe Asp Met Gly Ser
                85                  90                  95

Pro Asn Val Val Phe Gly Gly Gly Thr Lys Leu Thr Val Leu Gly Gln
            100                 105                 110


<210> SEQ ID NO 39
<211> LENGTH: 110
<212> TYPE: PRT
<213> ORGANISM: Homo sapiens

<400> SEQUENCE: 39

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Met Thr Leu Pro
                85                  90                  95

Leu Thr Phe Gly Gln Gly Thr Lys Val Glu Ile Lys Arg Thr
            100                 105                 110


<210> SEQ ID NO 40
<211> LENGTH: 17
<212> TYPE: PRT
<213> ORGANISM: Homo sapiens

<400> SEQUENCE: 40

Gly Ile Ser Gly Ser Gly Ser Tyr Thr Tyr Tyr Ala Asp Ser Val Lys
1               5                   10                  15

Phe


<210> SEQ ID NO 41
<211> LENGTH: 17
<212> TYPE: PRT
<213> ORGANISM: Homo sapiens

<400> SEQUENCE: 41

Gly Ile Ser Tyr Tyr Gly Gly Asn Thr Tyr Tyr Ala Asp Ser Val Lys
1               5                   10                  15

Phe


<210> SEQ ID NO 42
<211> LENGTH: 17
<212> TYPE: PRT
<213> ORGANISM: Homo sapiens

<400> SEQUENCE: 42

Gly Ile Ser Tyr Tyr Gly Gly Ser Thr Tyr Tyr Ala Asp Ser Val Lys
1               5                   10                  15

Phe


<210> SEQ ID NO 43
<211> LENGTH: 10
<212> TYPE: PRT
<213> ORGANISM: Homo sapiens

<400> SEQUENCE: 43

Gly Phe Thr Phe Ser Ser Tyr Gly Met Thr
1               5                   10


<210> SEQ ID NO 44
<211> LENGTH: 10
<212> TYPE: PRT
<213> ORGANISM: Homo sapiens

<400> SEQUENCE: 44

Gly Phe Thr Phe Asn Ser Tyr Gly Met Thr
1               5                   10


<210> SEQ ID NO 45
```

<211> LENGTH: 10
<212> TYPE: PRT
<213> ORGANISM: Homo sapiens

<400> SEQUENCE: 45

Gly Phe Thr Phe Ser Asn Tyr Gly Met Thr
1 5 10

<210> SEQ ID NO 46
<211> LENGTH: 10
<212> TYPE: PRT
<213> ORGANISM: Homo sapiens

<400> SEQUENCE: 46

Gly Phe Thr Phe Ser Ser Tyr Trp Met Thr
1 5 10

<210> SEQ ID NO 47
<211> LENGTH: 10
<212> TYPE: PRT
<213> ORGANISM: Homo sapiens

<400> SEQUENCE: 47

Gly Phe Thr Phe Ser Ser Tyr Ala Met Thr
1 5 10

<210> SEQ ID NO 48
<211> LENGTH: 10
<212> TYPE: PRT
<213> ORGANISM: Homo sapiens

<400> SEQUENCE: 48

Gly Phe Thr Phe Ser Ser Tyr Gly Met Ser
1 5 10

<210> SEQ ID NO 49
<211> LENGTH: 10
<212> TYPE: PRT
<213> ORGANISM: Homo sapiens

<400> SEQUENCE: 49

Gly Phe Thr Phe Ser Ser Tyr Gly Met Ser
1 5 10

<210> SEQ ID NO 50
<211> LENGTH: 10
<212> TYPE: PRT
<213> ORGANISM: Homo sapiens

<400> SEQUENCE: 50

Gly Phe Thr Phe Asn Asn Tyr Gly Met Thr
1 5 10

<210> SEQ ID NO 51
<211> LENGTH: 10
<212> TYPE: PRT
<213> ORGANISM: Homo sapiens

<400> SEQUENCE: 51

Gly Phe Thr Phe Ser Ser Tyr Trp Met Ser
1 5 10

<210> SEQ ID NO 52
<211> LENGTH: 10
<212> TYPE: PRT

<213> ORGANISM: Homo sapiens

<400> SEQUENCE: 52

Gly Phe Thr Phe Ser Ser Tyr Trp Met Ser
1 5 10

<210> SEQ ID NO 53
<211> LENGTH: 10
<212> TYPE: PRT
<213> ORGANISM: Homo sapiens

<400> SEQUENCE: 53

Gly Phe Thr Phe Ser Ser Tyr Trp Met Ser
1 5 10

<210> SEQ ID NO 54
<211> LENGTH: 10
<212> TYPE: PRT
<213> ORGANISM: Homo sapiens

<400> SEQUENCE: 54

Gly Phe Thr Phe Ser Ser Tyr Trp Met Ser
1 5 10

<210> SEQ ID NO 55
<211> LENGTH: 10
<212> TYPE: PRT
<213> ORGANISM: Homo sapiens

<400> SEQUENCE: 55

Gly Phe Thr Phe Ser Ser Tyr Trp Met Ser
1 5 10

<210> SEQ ID NO 56
<211> LENGTH: 10
<212> TYPE: PRT
<213> ORGANISM: Homo sapiens

<400> SEQUENCE: 56

Gly Phe Thr Phe Ser Ser Tyr Trp Met Ser
1 5 10

<210> SEQ ID NO 57
<211> LENGTH: 20
<212> TYPE: PRT
<213> ORGANISM: Homo sapiens

<400> SEQUENCE: 57

Trp Val Ser Gly Ile Ser Glu Arg Gly Val Tyr Ile Phe Tyr Ala Asp
1 5 10 15

Ser Val Lys Gly
20

<210> SEQ ID NO 58
<211> LENGTH: 20
<212> TYPE: PRT
<213> ORGANISM: Homo sapiens

<400> SEQUENCE: 58

Trp Val Ser Gly Ile Ser Gly Ser Gly Ser Tyr Thr Tyr Tyr Ala Asp
1 5 10 15

Ser Val Lys Gly
20

<210> SEQ ID NO 59
<211> LENGTH: 23
<212> TYPE: PRT
<213> ORGANISM: Homo sapiens

<400> SEQUENCE: 59

Trp Val Ser Asp Ile Glu His Lys Arg Arg Ala Gly Gly Ala Thr Ser
1 5 10 15

Tyr Ala Ala Ser Val Lys Gly
20

<210> SEQ ID NO 60
<211> LENGTH: 22
<212> TYPE: PRT
<213> ORGANISM: Homo sapiens

<400> SEQUENCE: 60

Trp Val Ser Met Ile Glu His Lys Thr Arg Gly Gly Thr Thr Asp Tyr
1 5 10 15

Ala Ala Pro Val Lys Gly
20

<210> SEQ ID NO 61
<211> LENGTH: 20
<212> TYPE: PRT
<213> ORGANISM: Homo sapiens

<400> SEQUENCE: 61

Trp Val Ser Gly Ile Ser Tyr Ser Gly Ser Asn Thr His Tyr Ala Asp
1 5 10 15

Ser Val Lys Gly
20

<210> SEQ ID NO 62
<211> LENGTH: 20
<212> TYPE: PRT
<213> ORGANISM: Homo sapiens

<400> SEQUENCE: 62

Trp Val Ser Val Ile Ser Ser Asp Ser Ser Ser Thr Tyr Tyr Ala Asp
1 5 10 15

Ser Val Lys Gly
20

<210> SEQ ID NO 63
<211> LENGTH: 20
<212> TYPE: PRT
<213> ORGANISM: Homo sapiens

<400> SEQUENCE: 63

Trp Val Ser Val Ile Ser Ser Asp Ser Ser Ser Thr Tyr Tyr Ala Asp
1 5 10 15

Ser Val Lys Gly
20

<210> SEQ ID NO 64
<211> LENGTH: 22
<212> TYPE: PRT
<213> ORGANISM: Homo sapiens

<400> SEQUENCE: 64

Trp Val Ser Val Ile Glu His Lys Ser Phe Gly Ser Ala Thr Phe Tyr 1 5 10 15

Ala Ala Ser Val Lys Gly
20

<210> SEQ ID NO 65
<211> LENGTH: 5
<212> TYPE: PRT
<213> ORGANISM: Homo sapiens

<400> SEQUENCE: 65

His Tyr Met Asp His
1 5

<210> SEQ ID NO 66
<211> LENGTH: 6
<212> TYPE: PRT
<213> ORGANISM: Homo sapiens

<400> SEQUENCE: 66

Thr Ile Tyr Met Asp Tyr
1 5

<210> SEQ ID NO 67
<211> LENGTH: 7
<212> TYPE: PRT
<213> ORGANISM: Homo sapiens

<400> SEQUENCE: 67

Met Gly Ile Asp Leu Asp Tyr
1 5

<210> SEQ ID NO 68
<211> LENGTH: 7
<212> TYPE: PRT
<213> ORGANISM: Homo sapiens

<400> SEQUENCE: 68

Met Gly Ile Asp Leu Asp Tyr
1 5

<210> SEQ ID NO 69
<211> LENGTH: 7
<212> TYPE: PRT
<213> ORGANISM: Homo sapiens

<400> SEQUENCE: 69

Met Gly Ile Asp Leu Asp Tyr
1 5

<210> SEQ ID NO 70
<211> LENGTH: 7
<212> TYPE: PRT
<213> ORGANISM: Homo sapiens

<400> SEQUENCE: 70

His Gly Ile Asp Phe Asp His
1 5

<210> SEQ ID NO 71
<211> LENGTH: 7
<212> TYPE: PRT
<213> ORGANISM: Homo sapiens

<400> SEQUENCE: 71

His Gly Ile Asp Phe Asp His
1 5

<210> SEQ ID NO 72
<211> LENGTH: 7
<212> TYPE: PRT
<213> ORGANISM: Homo sapiens

<400> SEQUENCE: 72

His Gly Ile Asp Phe Asp His
1 5

<210> SEQ ID NO 73
<211> LENGTH: 11
<212> TYPE: PRT
<213> ORGANISM: Homo sapiens

<400> SEQUENCE: 73

Arg Ala Ser Gln Asp Ile Ser Asn Tyr Leu His
1 5 10

<210> SEQ ID NO 74
<211> LENGTH: 12
<212> TYPE: PRT
<213> ORGANISM: Homo sapiens

<400> SEQUENCE: 74

Arg Ala Ser Gln Asn Leu Phe Ser Pro Tyr Leu Ala
1 5 10

<210> SEQ ID NO 75
<211> LENGTH: 14
<212> TYPE: PRT
<213> ORGANISM: Homo sapiens

<400> SEQUENCE: 75

Thr Gly Thr Ser Ser Asp Val Gly Gly Phe Asn Tyr Val Ser
1 5 10

<210> SEQ ID NO 76
<211> LENGTH: 14
<212> TYPE: PRT
<213> ORGANISM: Homo sapiens

<400> SEQUENCE: 76

Thr Gly Thr Ser Ser Asp Val Gly Gly Phe Asn Tyr Val Ser
1 5 10

<210> SEQ ID NO 77
<211> LENGTH: 14
<212> TYPE: PRT
<213> ORGANISM: Homo sapiens

<400> SEQUENCE: 77

Thr Gly Thr Ser Ser Asp Val Gly Gly Phe Asn Tyr Val Ser
1 5 10

<210> SEQ ID NO 78
<211> LENGTH: 14
<212> TYPE: PRT
<213> ORGANISM: Homo sapiens

<400> SEQUENCE: 78

Thr Gly Thr Ser Ser Asp Leu Gly Gly Tyr Asn Tyr Val Ser
1 5 10

<210> SEQ ID NO 79
<211> LENGTH: 14
<212> TYPE: PRT
<213> ORGANISM: Homo sapiens

<400> SEQUENCE: 79

Thr Gly Thr Ser Ser Asp Leu Gly Gly Tyr Asn Tyr Val Ser
1 5 10

<210> SEQ ID NO 80
<211> LENGTH: 14
<212> TYPE: PRT
<213> ORGANISM: Homo sapiens

<400> SEQUENCE: 80

Thr Gly Thr Ser Ser Asp Leu Gly Gly Tyr Asn Tyr Val Ser
1 5 10

<210> SEQ ID NO 81
<211> LENGTH: 11
<212> TYPE: PRT
<213> ORGANISM: Homo sapiens

<400> SEQUENCE: 81

Leu Leu Ile Tyr Gly Ala Ser Asn Leu Gln Ser
1 5 10

<210> SEQ ID NO 82
<211> LENGTH: 11
<212> TYPE: PRT
<213> ORGANISM: Homo sapiens

<400> SEQUENCE: 82

Leu Leu Ile Tyr Gly Ala Ser Asn Arg Ala Thr
1 5 10

<210> SEQ ID NO 83
<211> LENGTH: 11
<212> TYPE: PRT
<213> ORGANISM: Homo sapiens

<400> SEQUENCE: 83

Leu Met Ile His Asp Gly Ser Asn Arg Pro Ser
1 5 10

<210> SEQ ID NO 84
<211> LENGTH: 11
<212> TYPE: PRT
<213> ORGANISM: Homo sapiens

<400> SEQUENCE: 84

Leu Met Ile His Asp Gly Ser Asn Arg Pro Ser
1 5 10

<210> SEQ ID NO 85
<211> LENGTH: 11
<212> TYPE: PRT
<213> ORGANISM: Homo sapiens

<400> SEQUENCE: 85

Leu Met Ile His Asp Gly Ser Asn Arg Pro Ser
1 5 10

<210> SEQ ID NO 86
<211> LENGTH: 11
<212> TYPE: PRT
<213> ORGANISM: Homo sapiens

<400> SEQUENCE: 86

Leu Met Ile Tyr Asp Val Asn Asn Arg Pro Ser
1 5 10

<210> SEQ ID NO 87
<211> LENGTH: 11
<212> TYPE: PRT
<213> ORGANISM: Homo sapiens

<400> SEQUENCE: 87

Leu Met Ile Tyr Asp Val Asn Asn Arg Pro Ser
1 5 10

<210> SEQ ID NO 88
<211> LENGTH: 11
<212> TYPE: PRT
<213> ORGANISM: Homo sapiens

<400> SEQUENCE: 88

Leu Met Ile Tyr Asp Val Asn Asn Arg Pro Ser
1 5 10

<210> SEQ ID NO 89
<211> LENGTH: 8
<212> TYPE: PRT
<213> ORGANISM: Homo sapiens

<400> SEQUENCE: 89

Gln Gln Tyr Asp Ser Ile Pro Met
1 5

<210> SEQ ID NO 90
<211> LENGTH: 7
<212> TYPE: PRT
<213> ORGANISM: Homo sapiens

<400> SEQUENCE: 90

Gln Gln Tyr Leu Phe Pro Leu
1 5

<210> SEQ ID NO 91
<211> LENGTH: 9
<212> TYPE: PRT
<213> ORGANISM: Homo sapiens

<400> SEQUENCE: 91

Ser Thr Trp Asp Met Thr Val Asp Phe
1 5

<210> SEQ ID NO 92
<211> LENGTH: 9
<212> TYPE: PRT
<213> ORGANISM: Homo sapiens

<400> SEQUENCE: 92

Ser Thr Trp Asp Met Thr Val Asp Phe
1 5

<210> SEQ ID NO 93
<211> LENGTH: 10

<212> TYPE: PRT
<213> ORGANISM: Homo sapiens

<400> SEQUENCE: 93

Gln Ser Trp Gly Val Gly Pro Gly Gly Phe
1 5 10

<210> SEQ ID NO 94
<211> LENGTH: 10
<212> TYPE: PRT
<213> ORGANISM: Homo sapiens

<400> SEQUENCE: 94

Gln Ser Tyr Asp Pro Phe Leu Asp Val Val
1 5 10

<210> SEQ ID NO 95
<211> LENGTH: 10
<212> TYPE: PRT
<213> ORGANISM: Homo sapiens

<400> SEQUENCE: 95

Gln Ser Tyr Asp Ser Pro Thr Asp Ser Val
1 5 10

<210> SEQ ID NO 96
<211> LENGTH: 10
<212> TYPE: PRT
<213> ORGANISM: Homo sapiens

<400> SEQUENCE: 96

Gln Ser Tyr Ala Ser Gly Asn Thr Lys Val
1 5 10

<210> SEQ ID NO 97
<211> LENGTH: 654
<212> TYPE: DNA
<213> ORGANISM: Homo sapiens

<400> SEQUENCE: 97
gatatcgcac tgacccagcc agcttcagtg agcggctcac caggtcagag cattaccatc 60
tcgtgtacgg gtactagcag cgatgttggt ggttttaatt atgtgtcttg gtaccagcag 120
catcccggga aggcgccgaa acttatgatt catgatggtt ctaatcgtcc ctcaggcgtg 180
agcaaccgtt ttagcggatc caaaagcggc aacaccgcga gcctgaccat tagcggcctg 240
caagcggaag acgaagcgga ttattattgc cagtcttggg atgtttctcc tattactgct 300
gtgtttggcg gcggcacgaa gcttaccgtc ctaggtcagc ccaaggctgc cccctcggtc 360
actctgttcc cgccctcctc tgaggagctt caagccaaca aggccacact ggtgtgtctc 420
ataagtgact tctacccggg agccgtgaca gtggcctgga aggcagatag cagccccgtc 480
aaggcgggag tggagacaac cacaccctcc aaacaaagca acaacaagta cgcggccagc 540
agctatctga gcctgacgcc tgagcagtgg aagtcccaca gaagctacag ctgccaggtc 600
acgcatgaag ggagcaccgt ggaaaagaca gtggccccta cagaatgttc atag 654

<210> SEQ ID NO 98
<211> LENGTH: 654
<212> TYPE: DNA
<213> ORGANISM: Homo sapiens

<400> SEQUENCE: 98

-continued

```
gatatcgcac tgacccagcc agcttcagtg agcggctcac caggtcagag cattaccatc     60

tcgtgtacgg gtactagcag cgatcttggt ggttataatt atgtgtcttg gtaccagcag    120

catcccggga aggcgccgaa acttatgatt tatgatgtta ataatcgtcc ctcaggcgtg    180

agcaaccgtt ttagcggatc caaaagcggc aacaccgcga gcctgaccat tagcggcctg    240

caagcggaag acgaagcgga ttattattgc cagacttatg atcagattaa gttgtctgct    300

gtgtttggcg gcggcacgaa gcttaccgtc ctaggtcagc ccaaggctgc cccctcggtc    360

actctgttcc cgccctcctc tgaggagctt caagccaaca aggccacact ggtgtgtctc    420

ataagtgact tctacccggg agccgtgaca gtggcctgga aggcagatag cagccccgtc    480

aaggcgggag tggagacaac cacaccctcc aaacaaagca acaacaagta cgcggccagc    540

agctatctga gcctgacgcc tgagcagtgg aagtcccaca gaagctacag ctgccaggtc    600

acgcatgaag ggagcaccgt ggaaaagaca gtggccccta cagaatgttc atag          654


<210> SEQ ID NO 99
<211> LENGTH: 648
<212> TYPE: DNA
<213> ORGANISM: Homo sapiens

<400> SEQUENCE: 99

gatatcgtgc tgacccagag cccggcgacc ctgagcctgt ctccgggcga acgtgcgacc     60

ctgagctgca gagcgagcca gaatcttttt tctccttatc tggcttggta ccagcagaaa    120

ccaggtcaag caccgcgtct attaatttat ggtgcttcta atcgtgcaac tggggtcccg    180

gcgcgtttta gcggctctgg atccggcacg gattttaccc tgaccattag cagcctggaa    240

cctgaagact ttgcggtgta ttattgccag cagtatctta ctcttcctct tacctttggc    300

cagggtacga aagtcgagat caaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648


<210> SEQ ID NO 100
<211> LENGTH: 648
<212> TYPE: DNA
<213> ORGANISM: Homo sapiens

<400> SEQUENCE: 100

gatatcgtgc tgacccagag cccggcgacc ctgagcctgt ctccgggcga acgtgcgacc     60

ctgagctgca gagcgagcca gaatcttttt tctccttatc tggcttggta ccagcagaaa    120

ccaggtcaag caccgcgtct attaatttat ggtgcttcta atcgtgcaac tggggtcccg    180

gcgcgtttta gcggctctgg atccggcacg gattttaccc tgaccattag cagcctggaa    240

cctgaagact ttgcggtgta ttattgccag cagtatatga ctcttcctct tacctttggc    300

cagggtacga aagtcgagat caaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600
```

ggcctgagct cgcccgtcac aaagagcttc aacaggggag agtgttag 648

<210> SEQ ID NO 101
<211> LENGTH: 1347
<212> TYPE: DNA
<213> ORGANISM: Homo sapiens

<400> SEQUENCE: 101
caggcacagg tgcaattggt ggaaagcggc ggcggcctgg tgcaaccggg cggcagcctg 60
cgtctgagct gcgcggcctc cggatttacc ttttcttctt attggatgtc ttgggtgcgc 120
caagcccctg ggaagggtct cgagtgggtg agcggtatct cttattctgg tagcaatacc 180
cattatgcgg atagcgtgaa aggccgtttt accatttcac gtgataattc gaaaaacacc 240
ctgtatctgc aaatgaacag cctgcgtgcg gaagatacgg ccgtgtatta ttgcgcgcgt 300
atgggtattg atcttgatta ttggggccaa ggcaccctgg tcaccgtctc ctcagcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtcgt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctatagcaag ctcaccgtgg acaagagcag gtggcagcag 1260
gggaacgtct tctcatgctc cgtgatgcat gaggctctgc acaaccacta cacgcagaag 1320
agcctctccc tgtccccggg taaatga 1347

<210> SEQ ID NO 102
<211> LENGTH: 1347
<212> TYPE: DNA
<213> ORGANISM: Homo sapiens

<400> SEQUENCE: 102
caggcacagg tgcaattggt ggaaagcggc ggcggcctgg tgcaaccggg cggcagcctg 60
cgtctgagct gcgcggcctc cggatttacc ttttcttctt attggatgtc ttgggtgcgc 120
caagcccctg ggaagggtct cgagtgggtg agcgttatct cttctgattc tagctctacc 180
tattatgcgg atagcgtgaa aggccgtttt accatttcac gtgataattc gaaaaacacc 240
ctgtatctgc aaatgaacag cctgcgtgcg gaagatacgg ccgtgtatta ttgcgcgcgt 300
catggtattg attttgatca ttggggccaa ggcaccctgg tcaccgtctc ctcagcctcc 360
accaagggcc catcggtctt ccccctggca ccctcctcca agagcacctc tgggggcaca 420

-continued gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtcgt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctatagcaag ctcaccgtgg acaagagcag gtggcagcag 1260
gggaacgtct tctcatgctc cgtgatgcat gaggctctgc acaaccacta cacgcagaag 1320
agcctctccc tgtccccggg taaatga 1347

<210> SEQ ID NO 103
<211> LENGTH: 1338
<212> TYPE: DNA
<213> ORGANISM: Homo sapiens

<400> SEQUENCE: 103
caggtgcagc tggtggagag cggcggagga ctggtgcagc ctggcggcag cctgagactg 60
agctgtgccg ccagcggctt caccttcaac aactacggca tgacctgggt gaggcaggcc 120
cctggcaagg gcctggagtg ggtgtccggc atcagcggca gcggcagcta cacctactac 180
gccgacagcg tgaagggcag gttcaccatc agccgggaca acagcaagaa caccctgtac 240
ctgcagatga acagcctgag agccgaggac accgccgtgt actactgtgc ccggaccatc 300
tacatggact actggggcca gggcaccctg gtcaccgtct cctcagcctc caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtcg tgaccgtgcc ctccagcagc ttgggcaccc agacctacat ctgcaacgtg 600
aatcacaagc ccagcaacac caaggtggac aagagagttg agcccaaatc ttgtgacaaa 660
actcacacat gcccaccgtg cccagcacct gaactcctgg ggggaccgtc agtcttcctc 720
ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acaacagcac gtaccgtgtg 900
gtcagcgtcc tcaccgtcct gcaccaggac tggctgaatg gcaaggagta caagtgcaag 960
gtctccaaca aagccctccc agcccccatc gagaaaacca tctccaaagc caaagggcag 1020
ccccgagaac cacaggtgta caccctgccc ccatcccggg aggagatgac caagaaccag 1080
gtcagcctga cctgcctggt caaaggcttc tatcccagcg acatcgccgt ggagtgggag 1140
agcaatgggc agccggagaa caactacaag accacgcctc ccgtgctgga ctccgacggc 1200

-continued

```
tccttcttcc tctatagcaa gctcaccgtg gacaagagca ggtggcagca ggggaacgtc   1260

ttctcatgct ccgtgatgca tgaggctctg cacaaccact acacgcagaa gagcctctcc   1320

ctgtccccgg gtaaatga                                                 1338
```

<210> SEQ ID NO 104
<211> LENGTH: 654
<212> TYPE: DNA
<213> ORGANISM: Homo sapiens

<400> SEQUENCE: 104

```
gatatcgccc tgacccagcc cgccagcgtg tccggcagcc ctggccagag catcaccatc     60

agctgtaccg gcaccagcag cgatgtgggc ggcttcaact acgtgtcctg gtatcagcag    120

caccccggca aggcccccaa gctgatgatc cacgacggca gcaatagacc cagcggcgtg    180

tccaatagat tcagcggcag caagagcggc aacaccgcca gcctgaccat cagcggcctg    240

caggctgagg acgaggccga ctactactgc cagagctggg atgtgagccc catcaccgcc    300

gtgtttggcg gcggaacaaa gcttaccgtc ctaggtcagc ccaaggctgc cccctcggtc    360

actctgttcc cgccctcctc tgaggagctt caagccaaca aggccacact ggtgtgtctc    420

ataagtgact tctacccggg agccgtgaca gtggcctgga aggcagatag cagccccgtc    480

aaggcgggag tggagacaac cacaccctcc aaacaaagca acaacaagta cgcggccagc    540

agctatctga gcctgacgcc tgagcagtgg aagtcccaca gaagctacag ctgccaggtc    600

acgcatgaag ggagcaccgt ggaaaagaca gtggccccta cagaatgttc atag          654
```

<210> SEQ ID NO 105
<211> LENGTH: 654
<212> TYPE: DNA
<213> ORGANISM: Homo sapiens

<400> SEQUENCE: 105

```
gatatcgccc tgacccagcc cgccagcgtg tccggcagcc ctggccagag catcaccatc     60

agctgtaccg gcaccagcag cgacctgggc ggctacaact acgtgtcctg gtatcagcag    120

caccccggca aggcccccaa gctgatgatc tacgacgtga acaacagacc tagcggcgtg    180

tccaacagat tcagcggcag caagagcggc aacaccgcca gcctgaccat ctctggcctg    240

caggctgagg acgaggccga ctactactgc cagacctacg accagatcaa gctgtccgcc    300

gtgtttggcg gcggaacaaa gcttaccgtc ctaggtcagc ccaaggctgc cccctcggtc    360

actctgttcc cgccctcctc tgaggagctt caagccaaca aggccacact ggtgtgtctc    420

ataagtgact tctacccggg agccgtgaca gtggcctgga aggcagatag cagccccgtc    480

aaggcgggag tggagacaac cacaccctcc aaacaaagca acaacaagta cgcggccagc    540

agctatctga gcctgacgcc tgagcagtgg aagtcccaca gaagctacag ctgccaggtc    600

acgcatgaag ggagcaccgt ggaaaagaca gtggccccta cagaatgttc atag          654
```

<210> SEQ ID NO 106
<211> LENGTH: 648
<212> TYPE: DNA
<213> ORGANISM: Homo sapiens

<400> SEQUENCE: 106

```
gacatcgtgc tgacccagag ccccgccacc ctgagcctga gccctggcga gagagccacc     60

ctgtcttgta gggccagcca gaacctgttc agcccttacc tggcctggta tcagcagaag    120
```

cccggccagg cccccagact gctgatctac ggcgccagca acagagccac cggcgtgccc 180
gccagattca gcggcagcgg ctccggcacc gacttcaccc tgaccatcag cagcctggag 240
cctgaggatt tcgccgtgta ctactgccag cagtacctga ccctgcccct gaccttcggc 300
cagggcacca aggtcgagat caaacgaact gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 107
<211> LENGTH: 648
<212> TYPE: DNA
<213> ORGANISM: Homo sapiens

<400> SEQUENCE: 107
gacatcgtgc tgacccagag ccccgccacc ctgagcctga gccctggcga gagagccacc 60
ctgtcttgta gggccagcca gaacctgttc agcccttacc tggcctggta tcagcagaag 120
cccggccagg cccccagact gctgatctac ggcgccagca acagagccac cggcgtgccc 180
gccagattca gcggcagcgg ctccggcacc gacttcaccc tgaccatcag cagcctggag 240
cctgaggatt tcgccgtgta ctactgccag cagtacatga ccctgcctct gaccttcggc 300
cagggcacca aggtcgagat caaacgaact gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 108
<211> LENGTH: 1347
<212> TYPE: DNA
<213> ORGANISM: Homo sapiens

<400> SEQUENCE: 108
caggcccagg tgcagctggt ggagagcggc ggaggactgg tgcagcctgg cggcagcctg 60
agactgagct gtgccgccag cggcttcacc ttcagcagct actggatgag ctgggtgagg 120
caggcccctg gcaagggcct ggagtgggtg tccggcatca gctacagcgg cagcaatacc 180
cactacgccg acagcgtgaa gggcaggttc accatcagcc gggacaacag caagaacacc 240
ctgtacctgc agatgaacag cctgagagcc gaggacaccg ccgtgtacta ctgtgcccgg 300
atgggcatcg acctggatta ctggggccag ggcaccctgg tcaccgtctc ctcagcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtcgt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctatagcaag ctcaccgtgg acaagagcag gtggcagcag 1260
gggaacgtct tctcatgctc cgtgatgcat gaggctctgc acaaccacta cacgcagaag 1320
agcctctccc tgtccccggg taaatga 1347

<210> SEQ ID NO 109
<211> LENGTH: 1347
<212> TYPE: DNA
<213> ORGANISM: Homo sapiens

<400> SEQUENCE: 109
caggcccagg tgcagctggt ggagagcggc ggaggactgg tgcagcctgg cggcagcctg 60
agactgagct gtgccgccag cggcttcacc ttcagcagct actggatgag ctgggtgagg 120
caggcccctg gcaagggcct ggagtgggtg tccgtgatca gcagcgatag cagcagcacc 180
tactacgccg atagcgtgaa gggccggttc accatcagcc gggacaacag caagaacacc 240
ctgtacctgc agatgaacag cctgagagcc gaggacaccg ccgtgtacta ctgtgccagg 300
cacggcatcg acttcgacca ctggggccag ggcaccctgg tcaccgtctc ctcagcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtcgt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctatagcaag ctcaccgtgg acaagagcag gtggcagcag 1260
gggaacgtct tctcatgctc cgtgatgcat gaggctctgc acaaccacta cacgcagaag 1320
agcctctccc tgtccccggg taaatga 1347

<210> SEQ ID NO 110

<211> LENGTH: 1338
<212> TYPE: DNA
<213> ORGANISM: Homo sapiens

<400> SEQUENCE: 110

```
caggtgcaat tggtggaaag cggcggcggc ctggtgcaac cgggcggcag cctgcgtctg     60
agctgcgcgg cctccggatt tacctttaat aattatggta tgacttgggt gcgccaagcc    120
cctgggaagg gtctcgagtg ggtgagcggt atctctggtt ctggtagcta tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtactatt    300
tatatggatt attggggcca aggcaccctg gtcaccgtct cctcagcctc caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtcg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac cacaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtccccgg gtaaatga                                                 1338
```

<210> SEQ ID NO 111
<211> LENGTH: 217
<212> TYPE: PRT
<213> ORGANISM: Homo sapiens

<400> SEQUENCE: 111

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile His Asp Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Val Ser
                85                  90                  95

Pro Ile Thr Ala Val Phe Gly Gly Gly Thr Lys Leu Thr Val Leu Gly
```

```
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 112
<211> LENGTH: 217
<212> TYPE: PRT
<213> ORGANISM: Homo sapiens

<400> SEQUENCE: 112

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Tyr Asp Gln Ile
                85                  90                  95

Lys Leu Ser Ala Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 113
<211> LENGTH: 215
<212> TYPE: PRT
<213> ORGANISM: Homo sapiens
```

<400> SEQUENCE: 113

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Leu Thr Leu Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 114
<211> LENGTH: 215
<212> TYPE: PRT
<213> ORGANISM: Homo sapiens

<400> SEQUENCE: 114

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu Phe Ser Pro
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Met Thr Leu Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

-continued

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 115
<211> LENGTH: 446
<212> TYPE: PRT
<213> ORGANISM: Homo sapiens

<400> SEQUENCE: 115

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Ile Asp Leu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

-continued

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 116
<211> LENGTH: 446
<212> TYPE: PRT
<213> ORGANISM: Homo sapiens

<400> SEQUENCE: 116

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ser Val Ile Ser Ser Asp Ser Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Gly Ile Asp Phe Asp His Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Arg Val Glu Pro Lys Ser Cys Asp Lys Thr His Thr
210 215 220

Cys Pro Pro Cys Pro Ala Pro Glu Leu Leu Gly Gly Pro Ser Val Phe 225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 117
<211> LENGTH: 445
<212> TYPE: PRT
<213> ORGANISM: Homo sapiens

<400> SEQUENCE: 117

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Gly Met Thr Trp Val Arg Gln Ala Pro Gly Lys Gly Leu Glu Trp Val
35 40 45

Ser Gly Ile Ser Gly Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Ile Tyr Met Asp Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

-continued

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Arg Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 118
<211> LENGTH: 111
<212> TYPE: PRT
<213> ORGANISM: Homo sapiens

<400> SEQUENCE: 118

Thr Arg Cys Asp Ile Ala Leu Thr Gln Pro Ala Ser Val Ser Gly Ser
1 5 10 15

Pro Gly Gln Ser Ile Thr Ile Ser Cys Thr Gly Thr Ser Ser Asp Leu
20 25 30

Gly Gly Tyr Asn Tyr Val Ser Trp Tyr Gln Gln His Pro Gly Lys Ala
35 40 45

Pro Lys Leu Met Ile Tyr Asp Val Asn Asn Arg Pro Ser Gly Val Ser
50 55 60

Asn Arg Phe Ser Gly Ser Lys Ser Gly Asn Thr Ala Ser Leu Thr Ile
65 70 75 80

Ser Gly Leu Gln Ala Glu Asp Glu Ala Asp Tyr Tyr Cys Gln Thr Tyr
85 90 95

Asp Gln Ile Lys Leu Ser Ala Val Phe Gly Gly Gly Thr Lys Leu
100 105 110

<210> SEQ ID NO 119
<211> LENGTH: 117
<212> TYPE: PRT
<213> ORGANISM: Homo sapiens

<400> SEQUENCE: 119

Gly Val Gln Ala Gln Val Gln Leu Val Glu Ser Gly Gly Gly Leu Val
1 5 10 15

Gln Pro Gly Gly Ser Leu Arg Leu Ser Cys Ala Ala Ser Gly Phe Thr
20 25 30

Phe Ser Ser Tyr Trp Met Ser Trp Val Arg Gln Ala Pro Gly Lys Gly
35 40 45

Leu Glu Trp Val Ser Val Ile Ser Ser Asp Ser Ser Ser Thr Tyr Tyr
50 55 60

Ala Asp Ser Val Lys Gly Arg Phe Thr Ile Ser Arg Asp Asn Ser Lys
65 70 75 80

Asn Thr Leu Tyr Leu Gln Met Asn Ser Leu Arg Ala Glu Asp Thr Ala
85 90 95

Val Tyr Tyr Cys Ala Arg His Gly Ile Asp Phe Asp His Trp Gly Gln
100 105 110

Gly Thr Leu Val Thr
115

<210> SEQ ID NO 120
<211> LENGTH: 333
<212> TYPE: DNA
<213> ORGANISM: Homo sapiens

<400> SEQUENCE: 120
acgcgttgcg atatcgccct gacccagccc gccagcgtgt ccggcagccc tggccagagc 60
atcaccatca gctgtaccgg caccagcagc gacctgggcg gctacaacta cgtgtcctgg 120
tatcagcagc accccggcaa ggcccccaag ctgatgatct acgacgtgaa caacagacct 180
agcggcgtgt ccaacagatt cagcggcagc aagagcggca acaccgccag cctgaccatc 240
tctggcctgc aggctgagga cgaggccgac tactactgcc agacctacga ccagatcaag 300
ctgtccgccg tgtttggcgg cggaacaaag ctt 333

<210> SEQ ID NO 121
<211> LENGTH: 361
<212> TYPE: DNA
<213> ORGANISM: Homo sapiens

<400> SEQUENCE: 121
gagtccattg ggagtgcagg cccaggtgca gctggtggag agcggcggag gactggtgca 60
gcctggcggc agcctgagac tgagctgtgc cgccagcggc ttcaccttca gcagctactg 120
gatgagctgg gtgaggcagg cccctggcaa gggcctggag tgggtgtccg tgatcagcag 180
cgatagcagc agcacctact acgccgatag cgtgaagggc cggttcacca tcagccggga 240
caacagcaag aacaccctgt acctgcagat gaacagcctg agagccgagg acaccgccgt 300
gtactactgt gccaggcacg gcatcgactt cgaccactgg ggccagggca ccctggtcac 360
c 361

<210> SEQ ID NO 122
<211> LENGTH: 259
<212> TYPE: PRT
<213> ORGANISM: Homo sapiens

<400> SEQUENCE: 122

```
Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gln Gly Leu Ala Phe Gly
    50                  55                  60

Gly Ser Lys Lys Gly Lys Asn Leu Gly Gln Ala Tyr Pro Cys Ser Ser
65                  70                  75                  80

Asp Lys Glu Cys Glu Val Gly Arg Tyr Cys His Ser Pro His Gln Gly
                85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile
```

<210> SEQ ID NO 123
<211> LENGTH: 350
<212> TYPE: PRT
<213> ORGANISM: Homo sapiens

<400> SEQUENCE: 123

```
Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Lys
65                  70                  75                  80
```

Ala Ser Ser Glu Val Asn Leu Ala Asn Leu Pro Pro Ser Tyr His Asn
85 90 95

Glu Thr Asn Thr Asp Thr Lys Val Gly Asn Asn Thr Ile His Val His
100 105 110

Arg Glu Ile His Lys Ile Thr Asn Asn Gln Thr Gly Gln Met Val Phe
115 120 125

Ser Glu Thr Val Ile Thr Ser Val Gly Asp Glu Glu Gly Arg Arg Ser
130 135 140

His Glu Cys Ile Ile Asp Glu Asp Cys Gly Pro Ser Met Tyr Cys Gln
145 150 155 160

Phe Ala Ser Phe Gln Tyr Thr Cys Gln Pro Cys Arg Gly Gln Arg Met
165 170 175

Leu Cys Thr Arg Asp Ser Glu Cys Cys Gly Asp Gln Leu Cys Val Trp
180 185 190

Gly His Cys Thr Lys Met Ala Thr Arg Gly Ser Asn Gly Thr Ile Cys
195 200 205

Asp Asn Gln Arg Asp Cys Gln Pro Gly Leu Cys Cys Ala Phe Gln Arg
210 215 220

Gly Leu Leu Phe Pro Val Cys Thr Pro Leu Pro Val Glu Gly Glu Leu
225 230 235 240

Cys His Asp Pro Ala Ser Arg Leu Leu Asp Leu Ile Thr Trp Glu Leu
245 250 255

Glu Pro Asp Gly Ala Leu Asp Arg Cys Pro Cys Ala Ser Gly Leu Leu
260 265 270

Cys Gln Pro His Ser His Ser Leu Val Tyr Val Cys Lys Pro Thr Phe
275 280 285

Val Gly Ser Arg Asp Gln Asp Gly Glu Ile Leu Leu Pro Arg Glu Val
290 295 300

Pro Asp Glu Tyr Glu Val Gly Ser Phe Met Glu Glu Val Arg Gln Glu
305 310 315 320

Leu Glu Asp Leu Glu Arg Ser Leu Thr Glu Glu Met Ala Leu Gly Glu
325 330 335

Pro Ala Ala Ala Ala Ala Ala Leu Leu Gly Gly Glu Glu Ile
340 345 350

<210> SEQ ID NO 124
<211> LENGTH: 224
<212> TYPE: PRT
<213> ORGANISM: Homo sapiens

<400> SEQUENCE: 124

Met Val Ala Ala Val Leu Leu Gly Leu Ser Trp Leu Cys Ser Pro Leu
1 5 10 15

Gly Ala Leu Val Leu Asp Phe Asn Asn Ile Arg Ser Ser Ala Asp Leu
20 25 30

His Gly Ala Arg Lys Gly Ser Gln Cys Leu Ser Asp Thr Asp Cys Asn
35 40 45

Thr Arg Lys Phe Cys Leu Gln Pro Arg Asp Glu Lys Pro Phe Cys Ala
50 55 60

Thr Cys Arg Gly Leu Arg Arg Arg Cys Gln Arg Asp Ala Met Cys Cys
65 70 75 80

Pro Gly Thr Leu Cys Val Asn Asp Val Cys Thr Thr Met Glu Asp Ala
85 90 95

Thr Pro Ile Leu Glu Arg Gln Leu Asp Glu Gln Asp Gly Thr His Ala 100 105 110

Glu Gly Thr Thr Gly His Pro Val Gln Glu Asn Gln Pro Lys Arg Lys
115 120 125

Pro Ser Ile Lys Lys Ser Gln Gly Arg Lys Gly Gln Glu Gly Glu Ser
130 135 140

Cys Leu Arg Thr Phe Asp Cys Gly Pro Gly Leu Cys Cys Ala Arg His
145 150 155 160

Phe Trp Thr Lys Ile Cys Lys Pro Val Leu Leu Glu Gly Gln Val Cys
165 170 175

Ser Arg Arg Gly His Lys Asp Thr Ala Gln Ala Pro Glu Ile Phe Gln
180 185 190

Arg Cys Asp Cys Gly Pro Gly Leu Leu Cys Arg Ser Gln Leu Thr Ser
195 200 205

Asn Arg Gln His Ala Arg Leu Arg Val Cys Gln Lys Ile Glu Lys Leu
210 215 220

<210> SEQ ID NO 125
<211> LENGTH: 127
<212> TYPE: PRT
<213> ORGANISM: Homo sapiens
<220> FEATURE:
<221> NAME/KEY: MISC_FEATURE
<222> LOCATION: (99)..(116)
<223> OTHER INFORMATION: wherein X may be any amino acid

<400> SEQUENCE: 125

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Xaa Xaa Xaa Xaa Xaa Xaa Xaa Xaa Xaa Xaa Xaa Xaa Xaa Xaa
100 105 110

Xaa Xaa Xaa Xaa Trp Gly Gln Gly Thr Leu Val Thr Val Ser Ser
115 120 125

<210> SEQ ID NO 126
<211> LENGTH: 127
<212> TYPE: PRT
<213> ORGANISM: Homo sapiens
<220> FEATURE:
<221> NAME/KEY: MISC_FEATURE
<222> LOCATION: (99)..(116)
<223> OTHER INFORMATION: wherein X may be any amino acid

<400> SEQUENCE: 126

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

```
Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125


<210> SEQ ID NO 127
<211> LENGTH: 110
<212> TYPE: PRT
<213> ORGANISM: Homo sapiens
<220> FEATURE:
<221> NAME/KEY: MISC_FEATURE
<222> LOCATION: (90)..(97)
<223> OTHER INFORMATION: wherein X may be any amino acid

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Val Tyr Tyr Cys Xaa Xaa Xaa Xaa Xaa Xaa Xaa
                85                  90                  95

Xaa Thr Phe Gly Gln Gly Thr Lys Val Glu Ile Lys Arg Thr
            100                 105                 110


<210> SEQ ID NO 128
<211> LENGTH: 111
<212> TYPE: PRT
<213> ORGANISM: Homo sapiens
<220> FEATURE:
<221> NAME/KEY: MISC_FEATURE
<222> LOCATION: (91)..(98)
<223> OTHER INFORMATION: wherein X may be any amino acid

<400> SEQUENCE: 128

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Val Tyr Tyr Cys Xaa Xaa Xaa Xaa Xaa Xaa
                85                  90                  95
```

Xaa Xaa Thr Phe Gly Gln Gly Thr Lys Val Glu Ile Lys Arg Thr
100 105 110

<210> SEQ ID NO 129
<211> LENGTH: 113
<212> TYPE: PRT
<213> ORGANISM: Homo sapiens
<220> FEATURE:
<221> NAME/KEY: MISC_FEATURE
<222> LOCATION: (91)..(100)
<223> OTHER INFORMATION: wherein X may be any amino acid

<400> SEQUENCE: 129

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Xaa Xaa Xaa Xaa Xaa Xaa
85 90 95

Xaa Xaa Xaa Xaa Val Phe Gly Gly Gly Thr Lys Leu Thr Val Leu Gly
100 105 110

Gln

<210> SEQ ID NO 130
<211> LENGTH: 112
<212> TYPE: PRT
<213> ORGANISM: Homo sapiens
<220> FEATURE:
<221> NAME/KEY: MISC_FEATURE
<222> LOCATION: (90)..(99)
<223> OTHER INFORMATION: wherein X may be any amino acid

<400> SEQUENCE: 130

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Ser Asn
20 25 30

Tyr Val Ser Trp Tyr Gln Gln Leu Pro Gly Thr Ala Pro Lys Leu Leu
35 40 45

Ile Tyr Asp Asn Asn Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ser Glu Asp Glu Ala Asp Tyr Tyr Cys Xaa Xaa Xaa Xaa Xaa Xaa Xaa
85 90 95

Xaa Xaa Xaa Val Phe Gly Gly Gly Thr Lys Leu Thr Val Leu Gly Gln
100 105 110

<210> SEQ ID NO 131
<211> LENGTH: 11
<212> TYPE: PRT
<213> ORGANISM: Homo sapiens
<220> FEATURE:
<221> NAME/KEY: MISC_FEATURE
<222> LOCATION: (5)..(11)

<223> OTHER INFORMATION: wherein X may be any amino acid

<400> SEQUENCE: 131

Arg Ala Ser Gln Xaa Xaa Xaa Xaa Xaa Tyr Xaa
1 5 10

<210> SEQ ID NO 132
<211> LENGTH: 11
<212> TYPE: PRT
<213> ORGANISM: Homo sapiens
<220> FEATURE:
<221> NAME/KEY: MISC_FEATURE
<222> LOCATION: (9)..(11)

<400> SEQUENCE: 132

Leu Leu Ile Tyr Gly Ala Ser Asn Xaa Xaa Xaa
1 5 10

<210> SEQ ID NO 133
<211> LENGTH: 8
<212> TYPE: PRT
<213> ORGANISM: Homo sapiens
<220> FEATURE:
<221> NAME/KEY: MISC_FEATURE
<222> LOCATION: (4)..(8)
<223> OTHER INFORMATION: wherein X may be any amino acid

<400> SEQUENCE: 133

Gln Gln Tyr Xaa Xaa Xaa Pro Xaa
1 5

<210> SEQ ID NO 134
<211> LENGTH: 14
<212> TYPE: PRT
<213> ORGANISM: Homo sapiens

<400> SEQUENCE: 134

Thr Gly Thr Ser Ser Asp Val Gly Gly Phe Asn Tyr Val Ser
1 5 10

<210> SEQ ID NO 135
<211> LENGTH: 11
<212> TYPE: PRT
<213> ORGANISM: Homo sapiens
<220> FEATURE:
<221> NAME/KEY: MISC_FEATURE
<222> LOCATION: (4)..(7)
<223> OTHER INFORMATION: wherein X may be any amino acid

<400> SEQUENCE: 135

Leu Met Ile Xaa Asp Xaa Xaa Asn Arg Pro Ser
1 5 10

<210> SEQ ID NO 136
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: wherein X may be any amino acid

<400> SEQUENCE: 136

Xaa Xaa Trp Asp Xaa Xaa Xaa Xaa Xaa
1 5

COMPOSITIONS AND METHODS OF USE FOR ANTIBODIES OF DICKKOPF-1

PRIORITY INFORMATION

This U.S. application is a divisional application of Ser. No. 14/163,230, filed Jan. 24, 2014, which is a divisional application of Ser. No. 12/160,875, filed Jan. 12, 2007, which claims priority to U.S. Provisional Application No. 60/759,216, filed Jan. 13, 2006, the contents of which are incorporated herein by reference in their entirety.

FIELD OF USE

The present invention relates to compositions and methods of use for antibodies of Dickkopf-1 ("DKK1"), Dickkopf-4 ("DKK4"), or both, to treat DKK-related abnormalities of bone density, metabolism, diabetes, cancers and the like.

BACKGROUND OF THE INVENTION

The Wnt signaling pathway are involved in the control of embryonic development and neoplastic processes. Extracellular Wnt proteins are responsible for the growth and differentiation of many cell types, including in particular the growth, differentiation and regulation of osteoblasts, osteoclasts and adipocytes.

Many cancers are associated with bone tissues and can result in osteoblastic lesions such as those found in prostate cancer, or in osteolytic lesions such as those found in lung cancer, breast cancer, and multiple myeloma (e.g., Tian et al., 2003 New England J. Med. 349:2483-2494).

Members of the Wnt gene family encode secreted glycoproteins that are required for a variety of developmental processes (Fedi et al., 1999 J. Bio. Chem. 274:19465-19472). A Wnt family member protein initiates a signaling pathway that is important for the growth and differentiation of osteoblasts, which cause bone deposition. In addition to bone formation, bone resorption is an ongoing normal process conducted by cells known as osteoclasts. In contrast, receptor activator of nuclear factor-kappa B ligand (RANKL) is the final mediator of osteoclastic bone resorption, where it plays a major role in the pathogenesis of postmenopausal osteoporosis, as well as in bone loss associated with rheumatoid arthritis, metastatic cancer, multiple myeloma, aromatase inhibitor therapy and androgen deprivation therapy (see, e.g., Lewiecki (2006) Expert Opin Biol Ther. 6: 1041-50). Osteoprotegrin (OPG), which is expressed by osteoblasts, inhibits RANKL, thereby decreasing osteoclast activity and formation. The balance between anabolic bone formation and analytic bone resorption regulates normal bone density, while an increase in one or the other leads to increased bone density or increased bone loss, respectively.

Wnt binds and acts through other cell surface proteins and Wnt signaling can contribute to the neoplastic process. Furthermore, genetic alterations can affect a cellular protein complex known as adenomatous polyposis coli involving a protein β-catenin, and these complexes have been observed in cells of patients with diseases such as human colon cancer, melanomas, and hepatocellular carcinomas, indicating that aberrations of Wnt signaling pathways are relevant to the development of these and possibly other human cancers (Fedi et al., 1999 J. Bio. Chem. 274:19465-19472).

There are at least two families of proteins that inhibit Wnt signaling, namely the secreted frizzled-related family and the Dickkopf (DKK) family. The DKK family currently contains four family members, namely DKK1 (human DNA accno. NM_012242; PRT accno. 094907), DKK2 (human accno. NM_014421; PRT accno. NP_055236), DKK3 (human accno. NM_015881; PRT accno. AAQ88744), and DKK4 (human accno. NM_014420; PRT accno. NP_055235).

Dickkopf-1 (DKK1) is a secreted inhibitor of the Wnt/β-catenin signaling pathway. See, e.g., U.S. patent application 2005-0079173 to Niehrs; U.S. patent application 2004-0234515 to McCarthy. DKK1 possesses the ability to inhibit Wnt-induced axis duplication, and genetic analysis indicates that DKK1 acts upstream to inhibit Wnt signaling. DKK1 is also important in skeletal development as demonstrated by effects on the loss of bone structures in chicken and mouse embryos after exposure to elevated levels of DKK1 (Tian et al., 2003 New England J. Med. 349:2483-2494). Elevated DKK1 serum levels has been associated with prostate cancer, and elevated DKK1 and RANKL levels in bone marrow plasma and peripheral blood in patients with multiple myeloma are associated with the presence of focal bone lesions See, e.g., Tian 2003, OMIM accno. 605189. DKK1 also plays a role in adipogenesis, chondrogenesis, proliferation of the gastrointestinal epithelial proliferation, bone loss associated with rheumatisms, and initiation of hair follicle placode formation. OMIM accno. 605189.

Dickkopf-4 (DKK4) is less well characterized but is likewise a secreted inhibitor of the Wnt pathway. DKK4 has been shown to be deposited in plaques in patients with Alzheimers disease and is expressed in muscle. Wnt has no known role in muscle development, therefore it is postulated herein that DKK4 has an inhibitory role on muscle development.

There is a need for compositions and methods to treat cancers and bone density abnormalities, including such agents that interfere or neutralize DKK1 and/or DKK4 mediated antagonism of Wnt signaling.

SUMMARY OF THE INVENTION

An embodiment of the invention herein provides an antibody or an antigen binding portion thereof that selectively binds to and neutralizes a DKK1 and/or a DKK4 polypeptide or a fragment thereof. In a preferred embodiment, the antibody is a DKK1/4 neutralizing antibody. In various embodiments, the antigen-binding portion of the DKK1/4 neutralizing antibody does not bind a DKK2 or a DKK3.

In one embodiment the antibody or an antigen binding portion thereof is arranged within an immunoglobulin-like scaffold, such as a framework selected from, e.g., a human, humanized, humaneered, shark or camelid scaffold, and/or may additionally be recombinant, chimeric, or CDR grafted antibodies. For instance, technology designed to minimize the Human Anti-murine Antibody response (humaneering technology of Kalobios or humanization technology of PDL) are contemplated within the invention. Further, antigen binding portions specific to DKK1 or DKK4 may also be within non-immunoglobulin-like scaffold, including, e.g., arrayed within an adnectin, fibrinogen, ankyrin-derived repeats, etc. type of framework.

In a particular embodiment, the Dkk1 antibody is characterized as having an antigen-binding region that is specific for target protein DKK1, and the antibody or functional fragment binds to DKK1 or a fragment thereof. In a related embodiment, the DKK4 antibody is characterized as having an antigen-binding region that is specific for target protein DKK4, and the antibody or functional fragment binds to DKK4 or a fragment thereof. In a related embodiment, the Dkk4 antibody is characterized as having an antigen-binding region that is specific for target protein DKK4, and the antibody or functional fragment binds to DKK4 or a fragment thereof. In a preferred embodiment, the antibody or antigen-binding portion thereof binds to a DKK1 and a DKK4 polypeptide, but not to a DKK2 or DKK3 polypeptide.

In another embodiment the antibody or an antigen binding portion thereof is monoclonal. In another embodiment, the antigen-binding portion is polyclonal. In various embodiments, the DKK1 antibody or an antigen binding portion thereof binds a peptide consisting of 30 contiguous amino acids of a DKK1 or a DKK4 polypeptide.

In a related embodiment, the binding to DKK1 or DKK4 is determined at least by one of the following assays: inhibition of DKK1 or DKK4 antagonism of Wnt-signaled transcription; surface plasmon resonance affinity determination, enzyme-linked immunosorbent assay binding; electrochemiluminescence-based binding analysis; FMAT, SET, SPR, ALP, TopFlash, blood serum concentration of biomarkers such as osteocalcin (OCN), procollagen type 1 nitrogenous propeptide (P1NP) and osteoprotegrin (OPG), and binding to cell surface receptor(s) such as Frizzled (Fz), LRP (LRP5/6) or Kremen (Krm). In certain embodiments, the Dkk1 antibody or antigen-binding portion possesses at least one of the following properties: selectivity for DKK1 that is at least $10^3$-fold, $10^4$-fold or $10^5$-fold greater than for human DKK2 or DKK3; binds to DKK1 or DKK4 with a $K_{on}$ of less than 100 nM, 50 nM, 10 nM, 1.0 nM, 500 pM, 100 pM, 50 pM or 10 pM; and has an off-rate for DKK1 of less than $10^{-2}$ per sec, $10^{-3}$ per sec, $10^{-4}$ per sec, or $10^{-5}$ per sec.

In a related embodiment, an antibody of the invention competes with DKK1 and/or DKK4 for binding to LRP5/6. In a related embodiment, an antibody of the invention competes with DKK1 and/or DKK4 for binding to Krm.

In still another embodiment, the invention provides an isolated antigen-binding region of any of the above antibodies or functional fragments of these antibodies, and amino acid sequences of these. Thus in certain embodiments, the invention provides isolated amino acid sequences selected from the group of SEQ ID NOs: 2-20 and SEQ ID NOs: 40-72 and conservative or humaneered variants of these sequences.

Further, in certain additional embodiments, the invention provides amino acid sequences SEQ ID NOs: 2-20, 65-72, and conservative or humaneered variants of these sequences, which provide isolated antigen-binding regions each of which is an H-CDR-3.

In a related embodiment, the isolated antigen-binding region is an H-CDR2 region having an amino acid sequence, selected from SEQ ID NOs: 2-20, 57-64, and conservative or humaneered variants of these. In still another related embodiment, the isolated antigen-binding region is a consensus H-CDR2 region depicted in sequence selected from the group of SEQ ID NO: 40 having amino acid sequence GISGSGSYTYYADSVKF, SEQ ID NO: 41 having amino acid sequence GISYYGGNTYYADSVKF, and SEQ ID NO: 42 having amino acid sequence GISYYGGSTYYADSVKF, and conservative or humaneered variants of amino acid residues of these sequences.

In certain embodiments, the novel sequence provided is SEQ ID NOs: 2-5, 8-11, 20, 49-56, and conservative or humaneered variants of these, which provide an isolated antigen-binding region which is an H-CDR1 region.

In a related embodiment, the isolated antigen-binding region is a consensus H-CDR1 region having an amino acid sequence (using the one letter amino acid code) selected from amino acid sequences GFTFSSYGMT (SEQ ID NO: 43), GFTFNSYGMT (SEQ ID NO: 44), GFTFSNYGMT (SEQ ID NO: 45), GFTFSSYWMT (SEQ ID NO: 46), GFTFSSYAMT (SEQ ID NO: 47), GFTFSSYGMS (SEQ ID NO: 48) and conservative or humaneered variants of any of these sequences.

In another embodiment, the invention provides amino acid sequences which are isolated antigen-binding regions having an L-CDR3 region, such as amino acid sequences selected from SEQ ID NOs: 21-39, 89-96, and conservative or humaneered variants of these sequences. In still another related embodiment, the isolated antigen-binding region is an L-CDR1 region having an amino acid sequence selected from SEQ ID NOs: 21-39, 73-80, and conservative or humaneered variants of these sequences. In yet another related embodiment, the isolated antigen-binding region is an L-CDR2 region having an amino acid sequence selected from SEQ ID NOs: 21-39, 81-88, and conservative or humaneered variants of these sequences.

In certain embodiments, the isolated antigen-binding region is a variable light chain having an amino acid sequence selected from SEQ ID NOs: 21-39, and conservative or humaneered variants of these sequences.

In another embodiment, the invention provides a nucleotide sequence selected from the group of SEQ ID NOs: 97-103. In a related embodiment, each of these nucleotide sequences encodes an amino acid sequence and conservative or humaneered variants of these encoded amino acid sequences are also within the scope of the invention herein. In another related embodiment, the nucleotide sequence of each of SEQ ID NOs: 97-100 encodes an antigen binding light chain. In a further related embodiment, the nucleotide sequence of each of SEQ ID NOs: 101-103 encodes an antigen binding heavy chain. In yet another related embodiment, each of these nucleotide sequences is further optimized for expression in a cell. Preferred cells include, but are not limited to, e.g., Chinese hamster (e.g., CHO) cells, baculovirus, yeast, bacteria, myeloma cells, and/or *H. sapiens*.

Preferably, sequences are optimized for expression and for production and clinical use. Characteristics to be optimization for clinical use include but are not limited to, e.g., half-life, pharmacokinetics (PK), antigenicity, effector function, FcRn clearance, and patient response including antibody dependent cell cytotoxicity (ADCC) or complement dependent cytotoxicity (CDC) activities.

In a further embodiment, the invention provides an isolated antigen-binding region having a heavy chain encoded by a nucleotide sequence selected from the group of SEQ ID NOs: 101-103. In a related embodiment, the invention provides an isolated antigen-binding region having a light chain encoded by a nucleotide sequence selected from the group of SEQ ID NOs: 97-100. In yet another related embodiment, the invention provides an isolated antigen-binding region having a light chain encoded by a nucleotide sequence selected from the group of SEQ ID NOs: 97-100, and a heavy chain encoded by a nucleotide sequence selected from the group of SEQ ID NOs: 101-103.

In certain embodiments, the invention provides a nucleotide sequence selected from the group of SEQ ID NOs: 104-110. In a related embodiment, each of these nucleotide sequences encodes an amino acid sequence and conservative or humaneered variants of these amino acid sequences are also within the scope of the invention herein. In another related embodiment, the nucleotide sequence of each of SEQ ID NOs: 104-107 encodes an antigen binding light chain. In a further related embodiment, the nucleotide sequence of each of SEQ ID NOs: 108-110 encodes an antigen binding heavy chain. In yet another related embodiment, each of these nucleotide sequences is optimized for expression and/or for clinical use.

In a further embodiment, the invention provides an isolated antigen-binding region having a heavy chain encoded by a nucleotide sequence selected from the group of SEQ ID NOs: 108-110. In another related embodiment, the invention provides an isolated antigen-binding region having a light chain encoded by a nucleotide sequence selected from the group of SEQ ID NOs: 104-107. In yet another related embodiment, the invention provides an isolated antigen-binding region having a light chain encoded by a nucleotide sequence selected from the group of SEQ ID NOs: 104-107, and a heavy chain encoded by a nucleotide sequence selected from the group of SEQ ID NOs: 108-110.

In other embodiments, the invention provides an amino acid sequence selected from the group of SEQ ID NOs: 111-117, and provides conservative variants of these sequences. In a related embodiment, each of SEQ ID NOs: 111-114 depicts an antigen binding light chain. In another embodiment, each of SEQ ID NOs: 115-117 depicts an antigen binding heavy chain. In yet another related embodiment, the amino acid sequence is optimized for expression and/or for clinical use.

In a further embodiment, the invention provides an isolated antigen-binding region having a heavy chain depicted in an amino acid sequence selected from the group of SEQ ID NOs: 115-117, and provides conservative variants of these sequences. In a related embodiment, the invention provides an isolated antigen-binding region having a light chain depicted in an amino acid sequence selected from the group of SEQ ID NOs: 111-114, and provides conservative variants of these sequences. In yet another related embodiment, the invention provides an isolated antigen-binding region having a heavy chain depicted in an amino acid sequence selected from the group of SEQ ID NOs: 115-117, and provides conservative variants of these sequences, and a light chain depicted in an amino acid sequence selected from the group of SEQ ID NOs: 111-114, and provides conservative variants of these sequences.

In another embodiment, the invention provides a nucleotide sequence selected from the group of SEQ ID NOs: 120-121, and/or the an isolated antigen-binding region having a variable region of a light chain or a heavy chain encoded by the respective nucleotide sequences. In a related embodiment, each of these nucleotide sequences encodes an amino acid sequence, and conservative or humaneered variants of these amino acid sequences are also within the scope of the invention. In another related embodiment, the nucleotide sequence of SEQ ID NO: 120 encodes an antigen binding light chain. In a further related embodiment, the nucleotide sequence of SEQ ID NOs: 121 encodes an antigen binding heavy chain. In yet another related embodiment, each of these nucleotide sequences is further optimized for expression and/or for clinical use.

In certain embodiments, the invention provides an amino acid sequence selected from the group of 118-119 and conservative or humaneered variants of these sequences. In a related embodiment, SEQ ID NO: 118 depicts an antigen binding variable region of a light chain. In another related embodiment, SEQ ID NO: 119 depicts an antigen binding variable region of a heavy chain. In still another related embodiment, the amino acid sequence is optimized for expression and/or for clinical use.

In other embodiments, the invention provides an amino acid sequence having at least 60, 70, 80, 90, 95, 96, 97, 98 or 99% identity with the CDR regions depicted in SEQ ID NOs: 2-39. In a related embodiment, the invention provides, an amino acid sequence having at least 60, 70, 80, 90, 95, 96, 97, 98 or 99% identity with a sequence depicted in SEQ ID NOs: 111-120. In yet another related embodiment, the invention provides, a nucleotide sequence having at least 60, 70, 80, 90, 95, 96, 97, 98 or 99% identity with a sequence depicted in SEQ ID NOs: 97-110 and 120-121.

In a certain embodiment, any of the above isolated antibodies is an IgG. In a related embodiment, any of the above isolated antibodies is an IgG1, an IgG2, an IgG3 or an IgG4. In another embodiment, the antibody is an IgE, an IgM, an IgD or an IgA. In a related embodiment, the invention is selected from a monoclonal or a polyclonal antibody composition. In further embodiments, the antibody is chimeric, humanized, humaneered, recombinant, etc. In yet another embodiment, the invention provides an isolated human or humanized antibody or functional fragment of it, having an antigen-binding region that is specific for an epitope of DKK1, and the antibody or functional fragment binds to DKK1 or DKK4, or otherwise blocks binding of DKK1 or DKK4 to a cell surface receptor (e.g., receptors such as LRP5/6, Kremen, Frizzled). In certain embodiments the antibody or fragment of it prevents, treats, or ameliorates development of osteolytic lesions. In other embodiments, the anti-DKK composition of the invention prevents, treats, or ameliorates a DKK1- or DKK4-associated cancer or disease.

In a related embodiment, the invention provides an isolated human or humanized antibody or functional fragment of it, having an antigen-binding region that is specific for an epitope of target DKK1 or DKK4, and the epitope contains six or more amino acid residues from a polypeptide fragment comprising the CYS1-linker-CYS2 domains of DKK1 and/or DKK4. In a related embodiment, the epitope is a conformational epitope. In a preferred embodiment, the epitope resides within the CYS2 domain. In a particular embodiment, the epitope comprises a modified amino acid residue. In a related embodiment, the epitope contains at least one glycosylated amino acid residue.

Functional fragments include Fv and Fab fragments (including single chain versions such as scFv), as well other antigen-binding regions of an antibody, including those that are linked to a non-immunoglobulin scaffold and heavy chain antibodies such as camelid and shark antibodies and nanobodies. In a related embodiment, the isolated antibody as described above is an IgG. In another related embodiment, the isolated antibody as described above is an IgG1, an IgG2, IgG3 or an IgG4. In another embodiment, the antibody is an IgE, an IgM or an IgA. In a related embodiment, the invention is a polyclonal antibody composition.

In another embodiment, the invention provides a pharmaceutical composition having at least one of any of the above antibodies or functional fragments or conservative variants, and a pharmaceutically acceptable carrier or excipient of it.

In still another embodiment, the invention provides for a transgenic animal carrying a gene encoding any of the above antibodies or functional fragments of them.

In certain embodiments, the invention provides a method for treating a disorder or condition associated with DKK1 or DKK4 expression. As used herein, "DKK1-associated diseases" or "DKK4-associated diseases" include, but are not limited to, osteolytic lesions—especially osteolytic lesions associated with a myeloma, especially a multiple myeloma, or with cancers of the bone, breast, colon, melanocytes, hepatocytes, epithelium, esophagus, brain, lung, prostate or pancreas or metastasis thereof; bone loss associated with transplantation. Further diseases or disorders include but are not limited to, e.g., osteosarcoma, prostate cancer, hepatocellular carcinoma (HCC), myeloma including multiple myeloma, diabetes, obesity, muscle wasting, Alzheimers disease, osteoporosis, osteopenia, rheumatism, colitis and/or unwanted hair loss. The method involves administering to a subject in need thereof an effective amount of any of the above pharmaceutical compositions.

In a related embodiment, the disorder or condition to be treated is a bone density abnormality. In another related embodiment, the bone density abnormality to be treated is the presence of an osteolytic lesion in the subject.

In another embodiment, the disorder or condition to be treated is an osteoporotic condition, such as an osteolytic lesion associated with a cancer. In a related embodiment, the cancer to be treated is a myeloma, such as multiple myeloma, or a cancer of the bone, breast, colon, melanocytes, hepatocytes, epithelium, esophagus, brain, lung, prostate or pancreas or metastasis thereof. In other embodiments, the osteoporotic condition is osteoporosis or osteopenia or osteosarcoma.

In certain embodiments, any of the above methods further involve administering a chemotherapeutic agent. In a related embodiment, the chemotherapeutic agent is an anti-cancer agent. In another related embodiment, the chemotherapeutic agent is an anti-osteoporotic agent.

In still another embodiment, the invention provides a method for treating a target cell, the method involving blocking DKK1 or DKK4 interaction with the cell with any of the above antibodies or functional fragments of them. In general, the target cell bears a receptor that binds DKK1 or DKK4. In one embodiment, the target cell is an osteoblast, wherein treatment with the neutralizing anti-DKK1/4 composition of the invention will enhance proliferation and stimulate bone formation. In one embodiment, the target cell is a muscle cell, wherein treatment will counteract muscle wasting.

In a related embodiment, the method further involves treating a patient with the target cell with a chemotherapeutic agent or radiation. In a related embodiment, following administering or contacting, any of the methods above further involves observing amelioration or retardation of development of an osteolytic lesion.

In yet another embodiment, the invention provides a method for identifying DKK1 or DKK4 in serum. This method involves detecting DKK1 or DKK4 with any of the above antibodies or antibody fragments further having a detectable label. The label is radioactive, fluorescent, magnetic, paramagnetic, or chemiluminescent.

In another embodiment, any of the above human or humanized antibodies or antibody fragments are synthetic.

In another embodiment, the invention provides a pharmaceutical composition of any of the above antibodies or functional fragments of these antibodies and an additional therapeutic agent. The additional therapeutic agent can be selected from the group consisting of an anti-cancer agent; an anti-osteoporotic agent; an antibiotic; an antimetabolic agent; an antidiabetic agent; an anti-inflammatory agent; an anti-angiogenic agent; a growth factor; and a cytokine.

The invention further relates to a method of preventing or treating proliferative diseases or diseases, such as a cancer, in a mammal, particularly a human, with a combination of pharmaceutical agents which comprises:

(a) a DKK1/4 neutralizing agent of the invention; and (b) one or more pharmaceutically active agents;

wherein at least one pharmaceutically active agent is an anti-cancer therapeutic.

The invention further relates to pharmaceutical compositions comprising:

(a) a DKK1/4 neutralizing antibody;

(b) a pharmaceutically active agent; and (c) a pharmaceutically acceptable carrier;

wherein at least one pharmaceutically active agent is an anti-cancer therapeutic.

The present invention further relates to a commercial package or product comprising:

(a) a pharmaceutical formulation of a DKK1/4 neutralizing antibody; and (b) a pharmaceutical formulation of a pharmaceutically active agent for simultaneous, concurrent, separate or sequential use;

wherein at least one pharmaceutically active agent is an anti-cancer therapeutic.

In a certain embodiment, the invention provides an antibody having a first amino acid sequence which is a heavy chain selected from SEQ ID NOs: 2-20, and a sequence having at least 60, 70, 80, 90, 95, 96, 97, 98 or 99 percent sequence identity in the CDR regions with the CDR regions having SEQ ID NOs: 2-20; and a second amino acid sequence which is a light chain selected from SEQ ID NOs: 21-39, and a sequence having at least 60, 70, 80, 90, 95, 96, 97, 98 or 99 percent sequence identity in the CDR regions with the CDR regions shown in SEQ ID NOs: 21-39.

In still another embodiment, the invention provides an immunoconjugate made out of a first component which is an antibody or fragment as described above and a second component having a second amino acid sequence. For example, the immunoconjugate is a cytotoxin, or the immunoconjugate is a binding protein or antibody having a binding specificity for a target that is different from DKK1 or DKK4. For example, the target of the binding specificity different from DKK1 or DKK4 is a tumor antigen or tumor-associated protein on a surface of a cancer cell.

In certain embodiments, the invention provides for any of the above antibodies to be a bispecific antibody.

In another embodiment, the invention provides a kit having any of the above antibodies or antibody fragments. In some embodiments, the kit further contains a pharmaceutically acceptable carrier or excipient of it. In other related embodiments, any of the above antibodies in the kit is present in a unit dose. In yet another embodiment, the kit is an ELISA diagnostic kit. In a related embodiment, the kit includes instructions for use in administering any of the above antibodies to a subject.

DETAILED DESCRIPTION OF THE INVENTION

Figure 1:
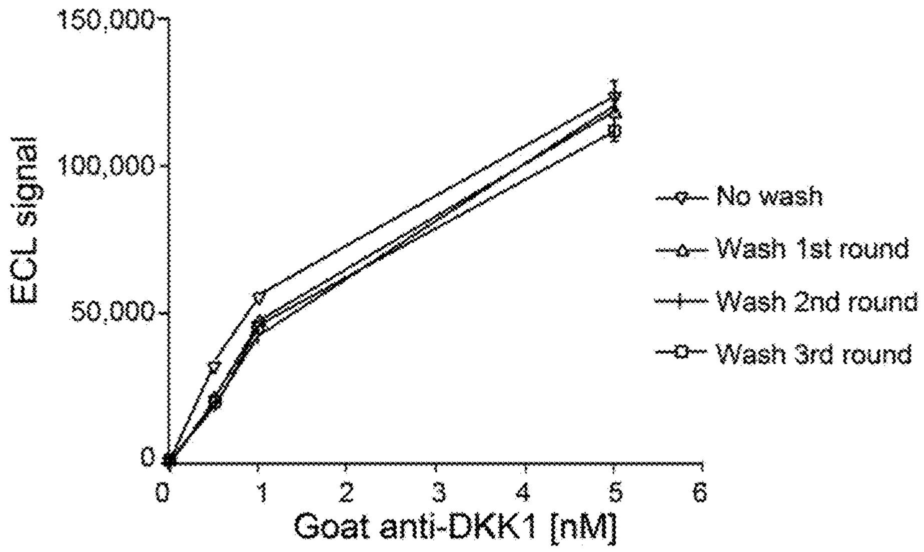
FIG. 1 is a graph illustrating no significant loss of His-Strep-tagged DKK1 from the Strep-Tactin-coated beads when the non-washed beads are compared with those beads washed with different HuCAL® stringencies.

The present invention relates to isolated DKK1/4 antibodies, particularly human antibodies, that bind specifically to DKK1 or DKK4 and that inhibit functional properties of DKK1 or DKK4. In a preferred embodiment, the DKK1/4 antibody does not specifically bind to DKK2 or DKK3. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunoconjugates or bispecific molecules of the invention. The invention also relates to methods of using the antibodies to inhibit a disorder or condition associated DKK1 or DKK4. Contemplated diseases and disorders include, but are not limited to, osteolytic lesions—especially osteolytic lesions associated with a myeloma, especially a multiple myeloma, or with cancers of the bone, breast, colon, melanocytes, hepatocytes, epithelium, esophagus, brain, lung, prostate or pancreas or metastasis thereof; bone loss associated with transplantation. Further diseases or disorders include but are not limited to, e.g., osteosarcoma, prostate cancer, hepatocellular carcinoma (HCC), myeloma including multiple myeloma, diabetes, obesity, muscle wasting, Alzheimers disease, osteoporosis, osteopenia, rheumatism, colitis and/or unwanted hair loss.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and capable of the transmission of such a signal across the plasma membrane of a cell. An example of a "cell surface receptor" of the present invention is a receptor to which the DKK1 or the DKK4 protein molecule binds. Such cell surface receptors include, but are not limited to, Frizzled (Fz), LRP (LRP5 and LRP6), and Kremen (Krm).

As used herein, the term "antibody" refers to polyclonal antibodies, monoclonal antibodies, humanized antibodies, single-chain antibodies, and fragments thereof such as $F_{ab}$, $F_{(ab')2}$, $F_v$, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as $F_{ab}$, $F_{(ab')2}$, $F_v$, and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "polyclonal antibody" refers to an antibody composition having a heterogeneous antibody population. Polyclonal antibodies are often derived from the pooled serum from immunized animals or from selected humans.

As used herein, the phrase "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

A "naturally occurring antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antigen portion"), as used herein, refers to the protein sequence that binds the target, e.g., one or more CDRs. It includes, e.g., full length antibodies, one or more fragments of an antibody, and/or CDRs on a non-immunoglobulin-related scaffold that retain the ability to specifically bind to an antigen (e.g., DKK1). The antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a $F(ab)_z$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

As used herein, an "antigen" or an "epitope" interchangeably refer to a polypeptide sequence on a target protein specifically recognized by an antigen-binding portion of an antibody, antibody fragment, or their equivalents. An antigen or epitope comprises at least 6 amino acids, which may be contiguous within a target sequence, or non-contiguous. A conformational epitope may comprise non-contiguous residues, and optionally may contain naturally or synthetically modified amino acid residues. Modifications to residues include, but are not limited to: phosphorylation, glycosylation, PEGylation, ubiquitinization, furanylization, and the like.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85: 5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

As described herein, the conservative variants include amino acid residues in any of the amino acid sequences identified, particularly conservative changes that are well known to one of ordinary skill in the art of protein engineering.

An "isolated antibody", as used herein, refers to an antibody that is substantially free of other antibodies having different antigenic specificities (e.g., an isolated antibody that specifically binds DKK1 is substantially free of antibodies that specifically bind antigens other than DKK1). An isolated antibody that specifically binds DKK1 may, however, have cross-reactivity to other antigens, such as DKK1 molecules from other species, or other family members such as DKK4 or related paralogs. Moreover, an isolated antibody may be substantially free of other cellular material and/or chemicals.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

As used herein, the term "humanized antibodies" means that at least a portion of the framework regions of an immunoglobulin are derived from human immunoglobulin sequences. A "humanized" antibodies such as antibodies with CDR sequences derived from the germline of another species, especially a mammalian species, e.g., a mouse, that have been grafted onto human framework sequences. Example technologies include humanization technology of PDL.

As used herein, the term "humaneered antibodies" means antibodies that bind the same epitope but differ in sequence. Example technologies include humaneered antibodies produced by humaneering technology of Kalobios, wherein the sequence of the antigen-binging region is derived by, e.g., mutation, rather than due to conservative amino acid replacements.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgA, IgD, IgM, IgE, IgG such as IgG1, IgG2, IgG3 or IgG4) that is provided by the heavy chain constant region genes.

The phrases "an antibody recognizing an antigen" and "an antibody specific for an antigen" are used interchangeably herein with the term "an antibody which binds specifically to an antigen." As used herein, an antibody that "specifically binds to human DKK1" is intended to refer to an antibody that binds to human DKK1 with a $K_D$ of $5\times10^{-9}$M or less, $2\times10^{-9}$M or less, or $1\times10^{-10}$ M or less. An antibody that "cross-reacts with an antigen other than human DKK1" is intended to refer to an antibody that binds that antigen with a $K_D$ of $0.5\times10^{-8}$M or less, $5\times10^{-9}$M or less, or $2\times10^{-9}$ M or less. An antibody that "does not cross-react with a particular antigen" is intended to refer to an antibody that binds to that antigen, with a $K_D$ of $1.5\times10^{-8}$ M or greater, or a $K_D$ of $5\text{-}10\times10^{-8}$ M or $1\times10^{-7}$ M or greater. In certain embodiments, such antibodies that do not cross-react with the antigen exhibit essentially undetectable binding against these proteins in standard binding assays. As used herein, an antibody that "inhibits binding of DKK1 to a cell surface receptor" such as LRP, Fz or Krm, refers to an antibody that inhibits DKK1 binding to the receptor with a K of 1 nM or less, 0.75 nM or less, 0.5 nM or less, or 0.25 nM or less.

As used herein, "osteolysis" refers to a decrease in bone density, which may be due to various mechanisms of action including, e.g., decreased osteoblast activity, increased osteoclast activity. Osteolysis therefore encompasses mechanisms that generically affect bone mineral density. As used herein, an antibody that "inhibits osteolytic activity" is intended to refer to an antibody that inhibits loss of bone density either by increasing bone formation or blocking a bone resorption.

The term "$K_{assoc}$" or "$K_a$", as used herein, is intended to refer to the association rate of a particular antibody-antigen interaction, whereas the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, by FMAT, or by using a biosensor system such as a Biacore® system.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

In order to get a higher avidity probe, a dimeric conjugate (two molecules of JWJ-1 coupled to a FACS marker) can be constructed, thus making low affinity interactions (such as with the germline antibody) more readily detected by FACS. In addition, another means to increase the avidity of antigen binding involves generating dimers or multimers of any of the fibronectin constructs described herein of the DKK1 or DKK4 antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in DKK1 or DKK4 hybrids to create such higher order structures.

As used herein, the term "cross-reactivity" refers to an antibody or population of antibodies binding to epitopes on other antigens. This can be caused either by low avidity or specificity of the antibody or by multiple distinct antigens having identical or very similar epitopes. Cross reactivity is sometimes desirable when one wants general binding to a related group of antigens or when attempting cross-species labeling when the antigen epitope sequence is not highly conserved in evolution.

As used herein, the term "high affinity" or "high specificity" for an IgG antibody refers to an antibody having a $K_D$ of $10^{-8}$M or less, $10^{-9}$M or less, or $10^{-10}$ M or less for a target antigen. However, "high affinity" binding can vary for other antibody isotypes. For example, "high affinity" binding for an IgM isotype refers to an antibody having a $K_D$ of $10^{-7}$M or less, or $10^{-8}$M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

As used herein, the term, "optimized" means that a nucleotide sequence has been altered to encode an amino acid sequence using codons that are preferred in the production cell or organism, and/or the nucleotide sequence has been altered to remove latent splice donor or splice acceptor sites. Optimized codon tables are well known in the art for a wide variety of species. Sequences for splice donor and acceptor sites are also known in the art and latent splice sites may be identified, e.g., by analysis of transcript or expression data. Production cells include, but are not limited to, a prokaryotic cell such as e.g., a prokaryotic cell such as a baculovirus or a bacteria (*E. coli*), or a eukaryotic cell, for example, yeast (e.g., *Pichia*), a Chinese Hamster Ovary cell (CHO), a myeloma cell or a human cell. The optimized nucleotide sequence is engineered to retain completely or as much as possible the amino acid sequence and residue number originally encoded by the starting nucleotide sequence, which is also known as the "parental" sequence. The optimized sequences herein have been engineered to have codons that are preferred in the production cells, however optimized expression of these sequences in other eukaryotic and prokaryotic cells is also envisioned herein. The amino acid sequences encoded by optimized nucleotide sequences are optionally referred to as optimized.

In related embodiments, polypeptide sequences of neutralizing anti-DKK1/4 compositions of the invention, and the nucleotides that encode them, are preferably optimized for production and clinical use. Characteristics that may be optimization for clinical use include, but are not limited to, e.g., half-life, pharmacokinetics (PK), antigenicity, effector function, FcRn clearance, and patient response including antibody dependent cell cytotoxicity (ADCC) or complement dependent cytotoxicity (CDC) activities.

As used herein, "DKK1-associated diseases" or "DKK4-associated diseases" include, but are not limited to, osteolytic lesions—especially osteolytic lesions associated with a myeloma, especially a multiple myeloma, or with cancers of the bone, breast, colon, melanocytes, hepatocytes, epithelium, esophagus, brain, lung, prostate or pancreas or metastasis thereof; bone loss associated with transplantation. Further diseases or disorders include but are not limited to, e.g., osteosarcoma, prostate cancer, hepatocellular carcinoma (HCC), myeloma including multiple myeloma, diabetes, obesity, muscle wasting, Alzheimers disease, osteoporosis, osteopenia, rheumatism, colitis and/or unwanted hair loss.

As used herein, a "treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. The "pathology" of cancer includes all phenomena that compromise the well being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Treatment of patients suffering from clinical, biochemical, radiological or subjective symptoms of the disease, such as osteolysis, may include alleviating some or all of such symptoms or reducing the predisposition to the disease.

In general, a neutralizing anti-DKK1/4 composition of the invention prevents, treats, or ameliorates Wnt-related diseases associated with DKK1 or DKK4 or both, but not diseases associated with DKK2, DKK3 or with other modulators of the Wnt pathway.

Various aspects of the invention are described in further detail in the following subsections.

The Wnt pathway is a major regulator of mesenchymal stem cell (MSC) differentiation into osteoblasts. It is also an important survival factor for active osteoblasts. Dickkopf-1 (DKK1) is a Wnt pathway antagonist expressed predominantly in bone in adults and is upregulated in myeloma patients with osteolytic lesions. A neutralizing anti-DKK1/4 antibody is a truly anabolic agent, which acts through increasing osteoblastic activity while simultaneously decreasing osteoclastic activity. In contrast, current drugs such as PTH, which are marketed as anabolic agents, in fact increase markers associated with both osteoblast ands osteoblasts.

Provided in the invention are polyclonal and monoclonal antibodies selected for binding to DKK1. A preferred antibody has an affinity of less than 10 pM against human DKK1. In some embodiments, the anti-DKK1 antibody crossreacts with DKK4 (Kd~300 pM) but not DKK2 (affinity analysis ongoing).

A preferred epitope for an anti-DKK1 or anti-DKK4 antibody is mapped to the Cys-2 domain (AAs 189-263), which is known to be responsible for both LRP6 and Kremen binding. In one embodiment, the epitope includes at least six, and at most thirty, amino acid residues from the Cys-2 domain of a DKK1 or a DKK4 polypeptide. In a certain embodiment, the epitope includes a stretch of at least six contiguous amino acids. In another embodiments, the preferred binding site is non-linear, i.e., includes non-contiguous amino acid residues. In some embodiments, binding depends on N-glycosylation. Only one N-glycosylation site is predicted, at residue 256 in the Cys-2 domain.

In the present invention, a neutralizing anti-DKK1 antibody blocks the interaction of DKK1 with LRP6 in both ELISA and cell surface binding assays. As expected this effectively neutralizes the Wnt suppressive activity of DKK1 at EC50's below 1 nM in vitro.

In an in vitro model of osteoblast differentiation, mouse 10T1/2 cells are treated with Wnt3A to stimulate secretion of alkaline phosphatase (AP), a marker for osteoblast activity. DKK1 blocks AP production in this model and antibodies of the invention fully reverses this inhibition.

In certain embodiments, an antibody of the invention exhibits dose linear pharmacokinetics (AUC) in mice, with a dose dependent terminal half-life of 35-96 hours in mice over a dose of 20-200 μg/mouse.

Using the intratibial model of osteolytic prostate tumor metastasis, antibodies of the invention inhibit tumor-induced cortical bone damage. Effects on trabecular bone are confounded in this model by the observation that both tumor implants and sham implants cause mechanical damage to the bone, which results in an initial increase in woven bone that is later remodeled, thus causing a decrease in apparent bone volume. In a certain embodiment, an antibody of the invention increases the production of woven bone in both tumor and sham implanted tibias and inhibits the decrease in bone volume accompanying remodeling.

In related embodiments, changes in bone markers (osteocalcin, sRANKL, OPG, AP, TRAP) are used to demonstrate clinical effects of antibodies of the invention on bone-related diseases and to predict clinical outcomes of treatments with pharmaceutically effective levels of a neutralizing anti-DKK1 antibody as provided herein. Krm binds DKK in approx same region as LRP. Krm needed for Wnt signal inhibition via DKK interaction with LRP. Krm-DKK-LRP complexed in order to be internalized for Wnt pathway deactivation.

A neutralizing anti-DKK1/4 composition of the invention preferably binds DKK1 or DKK4, blocking their interaction with LRP and/or Krm, thereby neutralizing DKK1 or DKK4 effect on Wnt signaling pathway. Wnt pathway reactivation occurs only where DKK1 and/or DKK4 are limiting.

Standard assays to evaluate the binding ability of the antibodies toward DKK1 of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis, BioVeris SET assay, FMAT, chemiluminescense, and/or SPR assays—signal inhibition or release assays. Assays to evaluate the effects of the antibodies on functional properties of DKK1 are described in further detail in the Examples.

Accordingly, an antibody that "inhibits" one or more of these DKK1 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits DKK1 activity effects such a statistically significant decrease by at least 10% of the measured parameter, by at least 50%, 80% or 90%, and in certain embodiments an antibody of the invention may inhibit greater than 95%, 98% or 99% of DKK1 functional activity.

Dickkopf Family Members

Appropriate bone metabolism involves a complex web of regulatory pathways and interconnections between osteoblasts, osteoclasts and the surrounding stroma. Imbalances in these regulatory mechanisms are involved in osteolytic conditions such as osteoporosis, tumor-induced osteolytic lesions, renal and liver transplant induced bone loss, and anti-hormone chemotherapy induced-bone loss. These conditions can have severe symptoms including bone pain, fractures, vertebral compression, and reduced mobility. Most treatments approved or currently under clinical evaluation act predominantly by inhibiting osteoclast function. For example, bisphosphonates such as zoledronic acid (Zometa) are the current standard of care and act by inhibiting osteoclast function and survival. While bisphosphonates are generally effective, some patients do not respond robustly or discontinue use due to renal toxicity or osteonecrosis [Markowitz 2003] [Ruggiero 2004]. In addition there are multiple investigational drugs targeting osteoclast development such as RANKL and M-CSF neutralizing antibodies, or osteoclast function such as Cathepsin K inhibitors.

Stimulation of osteoblast activity would provide a novel mechanism by which to treat osteolytic disease. The Wnt pathway plays a major role in osteoblast differentiation and activity, while the Dickkopf (DKK) family of antagonists in particular have been identified as key regulators of this process in vitro (see [Krishnan 2006] for review). In vitro, Wnt is an essential osteoblast survival and differentiation factor. Clinical validation for the role of the Wnt pathway is provided by mutations in the Wnt co-receptor, LRP5. Inactivating mutations in LRP5 result in osteoporosis-pseudoglioma syndrome (OPPG) [Ai 2005], while activating mutations result in high bone mass [Boyden 2002]. These activating mutations are found in the extracellular domain and have been demonstrated to impair binding to the Dickkopf (DKK) family of Wnt antagonists.

DKK1 has been reported to be overexpressed in myeloma cells from patients with bone lesions but absent in normal plasma cells or in plasma cells from patients without bone lesions [Tian 2004] [Politou 2006]. Such an overexpression of DKK1 by myeloma cells may upset the normal balance between osteoblasts and osteoclasts by blocking osteoblast differentiation, and thus promoting bone resorption. Moreover, some of the anti-tumor treatments used for myeloma, such as dexamethasone, have been reported to upregulate DKK1 [Ohnaka 2004]. Therefore, an anti-DKK1 neutralizing antibody should allow reactivation of the Wnt pathway in osteolytic lesions, while not affecting Wnt signaling in other tissues where DKK1 levels are relatively low or where other antagonists predominate. In adults, DKK1 has been reported to be highly expressed only in bone [Li 2006], suggesting an ongoing role for DKK1 in regulating bone metabolism in adults.

Transgenic mice overexpressing Wnt1 in breast tissue develop mammary carcinomas [Tsukamoto 1988] and ~90% of human colorectal cancers have mutations in either APC or β-catenin, two cytoplasmic components of the Wnt pathway [Morin 1997] [Rowan 2000]. This type of evidence raises concerns that activation of the Wnt pathway could be a risk for increased tumor initiation or progression. In addition, DKKs are down regulated in colorectal tumors and melanomas, suggesting a potential tumor suppressive role.

A DKK polypeptide of the invention includes DKK1 (SEQ ID NO:1) and DKK4 (SEQ ID NO:124), as well as DKK2 (SEQ ID NO: 122) and DKK3 (SEQ ID NO:123). DKK family members have two CYS domains (CYS1 and CYS2) as shown in the Table A—DKK1 Family Member PileUp. DKK proteins contains an acid N-terminal signal peptide, two CYS domains containing clusters of cysteine residues separated by a divergent linker region, and a potential C-terminal N-glycosylation site. The CYS2 domain in DKK4 has a lipid-binding function that may facilitate WNT/DKK interactions at the plasma membrane. OMIM accno. 605417.

TABLE A

DKK1 Family Member PileUp

| | | | | | | |
|---|---|---|---|---|---|---|
| hDKK1 | ~~~~~~~~~~ | ~~~~~~~~~~ | ~~~~~~~~~~ | ~~~~~~~~~~ | ~~~~~~~~~~ | |
| hDKK2 | ~~~~~~~~~~ | ~~~~~~~~~~ | ~~~~~~~~~~ | ~~~~~~~~~~ | ~~~~~~~~~~ | |
| hDKK3 | MQRLGATLLC | LLLAAAVPTA | PAPAPTATSA | PVKPGPALSY | PQEEATLNEM | |
| hDKK4 | ~~~~~~~~~~ | ~~~~~~~~~~ | ~~~~~~~~~~ | ~~~~~~~~~~ | ~~~~~~~~~~ | |
| hDKK1 | ~~~~~~~~~~ | ~~~~~~~~~~ | ~~~~~~~~~~ | ~~~~~~~~~~ | ~~~~~~~~~~ | |
| hDKK2 | ~~~~~~~~~~ | ~~~~~~~~~~ | ~~~~~~~~~~ | ~~~~~~~~~~ | ~~~~~~~~~~ | |
| hDKK3 | MQRLGATLLC | LLLAAAVPTA | PAPAPTATSA | PVKPGPALSY | PQEEATLNEM | |
| hDKK4 | ~~~~~~~~~~ | ~~~~~~~~~~ | ~~~~~~~~~~ | ~~~~~~~~~~ | ~~~~~~~~~~ | |
| | 51 | | | | 100 | |
| hDKK1 | ~~~~~~~~~M | MALGAAGATR | VFVAMVAAAL | GGHPLLGVSA | TLNSVLNSNA | |
| hDKK2 | ~~~~~~~~~M | AALMRSKDSS | CCLLLLAAVL | ....MVESSQ | IGSSRAKLNS | |
| hDKK3 | MQRLGATLLC | TQHKLRSAVE | EMEAEEAAAK | ASSEVNLANL | PPSYHNETNT | |
| hDKK4 | ~~~~~~~~~~ | ~~~~~~~~~~ | ~~~~~~~~~~ | ~~~~~~~~~~ | ~~~~~~~~~~ | |
| | 101 | | | | 150 | |
| hDKK1 | IKNLPPPLGG | AAGHPGSAVS | AAPGILYPG. | ..GNKYQTID | NYQPYPCAED | |
| hDKK2 | IKS...SLGG | ET..PGQAAN | RSAG.MYQGL | AFGGSKKGKN | LGQAYPCSSD | |
| hDKK3 | DTKVGNNTIH | VHREIHKITN | NQTGQMVFSE | TVITSVGDEE | GRRSHECIID | |
| hDKK4 | ~~~~~~MVAA | VLLGLSWLCS | PLGALVLDFN | NIRSSADLHG | ARKGSQCLSD | |
| | 151 | | CYS1 | | 200 | |
| hDKK1 | EECGTDEYCA | SPTRGGDAGV | QICLACRKRR | KRCMRHAMCC | PGNYCKNGIC | |
| hDKK2 | KECEVGRYCH | SPHQGSSA.. | ..CMVCRRKK | KRCHRDGMCC | PSTRCNNGIC | |
| hDKK3 | EDCGPSMYCQ | .....FASFQ | YTCQPCRGQR | MLCTRDSECC | GDQLCVWGHC | CYS1 |
| hDKK4 | TDCNTRKFCL | QPRD....EK | PFCATCRGLR | RRCQRDAMCC | PGTLCVNDVC | |
| | 201 | | | | 250 | |
| hDKK1 | VSSDQN..HF | RGEI...EET | ITESFGNDH. | STLD.GYSRR | TTLSSKMYHT | |
| hDKK2 | IPVTES..IL | TPHIPALDGT | RHRDRNHGHY | SNHDLGWQNL | GRPHTKMSHI | |
| hDKK3 | TKMA...... | .......... | .......... | .......... | .........T | |
| hDKK4 | TTMEDATPIL | ERQLDEQDGT | .HAEGTTGH. | .PVQENQPKR | KPSIKKSQGR | |
| | 251 | | | CYS2 | 300 | |
| hDKK1 | KGQEGSVCLR | SSDCASGLC | A..RHFWSKI | CKPVLKEGQV | CTKHRRK... | |
| hDKK2 | KGHEGDPCLR | SSDCIEGFCC | A..RHFWTKI | CKPVLHQGEV | CTKQRKK... | |
| hDKK3 | RGSNGTICDN | QRDCQPGLCC | AFQRGLLFPV | DTPLPVEGEL | CHDPASRLLD | |
| hDKK4 | KGQEGESCLR | TFDCGPGLCC | A..RHFWTKI | CKPVLLEGQV | CSRRGHK... | |
| | | | | | | CYS2 |
| | 301 | | | | 350 | |
| hDKK1 | ...G.SHGLE | IFQRCYCGEG | LSCRIQKDHH | QASNSSRLHT | CQRH~~~~~~ | |
| hDKK2 | ...G.SHGLE | IFQRCDCAKG | LSCKVWKD.A | TYSSKARLHV | CQKI~~~~~~ | |
| hDKK3 | LITWELEPDG | ALDRCPCASG | LLC....... | QPHSHSLVYV | CKPTFVGSRD | |
| hDKK4 | ...DTAQAPE | IFQRCDCGPG | LLCRSQLTSN | R..QHARLRV | CQKIEKL~~~ | |

TABLE A-continued

| DKK1 Family Member PileUp | | | | | | |
|---|---|---|---|---|---|---|
| | 351 | | | | 400 | |
| hDKK1 | ~~~~~~~~~~ | ~~~~~~~~~~ | ~~~~~~~~~~ | ~~~~~~~~~~ | ~~~~~~~~~~ | |
| hDKK2 | ~~~~~~~~~~ | ~~~~~~~~~~ | ~~~~~~~~~~ | ~~~~~~~~~~ | ~~~~~~~~~~ | |
| hDKK3 | QDGEILLPRE | VPDEYEVGSF | MEEVRQELED | LERSLTEEMA | LGEPAAAAAA | |
| hDKK4 | ~~~~~~~~~~ | ~~~~~~~~~~ | ~~~~~~~~~~ | ~~~~~~~~~~ | ~~~~~~~~~~ | |
| | 401 | | | | | |
| hDKK1 | ~~~~~~~ | (SEQ ID NO: 1) | | | | |
| hDKK2 | ~~~~~~~ | (SEQ ID NO: 122) | | | | |
| hDKK3 | LLGGEEI | (SEQ ID NO: 123) | | | | |
| hDKK4 | ~~~~~~~ | (SEQ ID NO: 124) | | | | |

Antibodies Against DKK1 and DKK4

In a preferred embodiment, the antibody of the invention is specific to a human DKK protein. In a more preferred embodiment, the antibody of the invention A DKK1 or DKK4 neutralizing antibody is distinct from the Wnt pathway modifications that have been linked to tumor promotion. The Wnt pathway is regulated by a complex network of extracellular ligands, receptors and antagonists of which DKK1 is only one. Due to the restricted expression of DKK1 in adults and its functional redundancy with other Wnt antagonists a neutralizing DKK1 antibody is unlikely to cause widespread activation of Wnt signaling or therefore, tumorigenesis. This is further supported by two observations: first, activating LRP5 mutations (inhibiting DKK binding) induce a high bone mass phenotype but have no apparent increased cancer risk [Moon 2004], while DKK1 heterozygous null or Doubleridge mice have decreased DKK1 levels, high bone mass phenotype, but no reported increased rate of tumor formation [MacDonald 2004].

An anti-DKK1 antibody should positively impact myeloma-induced osteolytic disease while not increasing the risk of de novo tumorigenesis. It is expected that such an antibody would be used in combination with anti-tumor chemotherapies and possibly with anti-bone resorption drugs that inhibit osteoclast function.

Polyclonal Antibodies

Antibodies of the invention may be polyclonal antibodies, especially human polyclonal antibodies. Polyclonals are derived from the pooled serum from immunized animals or from selected humans.

Monoclonal Antibodies

Antibodies of the invention are preferably the human monoclonal antibodies, such as the isolated and structurally characterized, e.g., in Examples 1-8. Specific $V_H$ amino acid sequences of the antibodies are shown, e.g., in SEQ ID NOs: 2-20. Specific $V_L$ amino acid sequences of the antibodies are shown, e.g., in SEQ ID NOs: 21-39.

A $V_H$ amino acid sequence of the antibody may be optimized for expression in a mammalian cell, e.g., such as the sequence shown in SEQ ID NO: 119. A $V_L$ amino acid sequence of the antibodies may be optimized for expression in a mammalian cell, e.g., such as the sequence shown in SEQ ID NO: 118. Likewise, sequences may be optimized for expression in, e.g., yeast, bacteria, hamster and other cells, depending on which expression system is preferred for the characteristic being optimized. Other antibodies of the invention include amino acids that have been mutated, yet have at least 60, 70, 80, 90, 95, 96, 97, 98 or 99 percent identity in the CDR regions with the CDR regions depicted in the sequences described above.

Further, full length light chain parental nucleotide sequences are shown in SEQ ID NOs: 97-100. Full length heavy chain parental nucleotide sequences are shown in SEQ ID NOs: 101-103. Full length light chain nucleotide sequences optimized for expression in a mammalian cell are shown in SEQ ID NOs: 104-107. Full length heavy chain nucleotide sequences optimized for expression in a mammalian cell are shown in SEQ ID NOs: 108-110. Full length light chain amino acid sequences encoded by optimized light chain nucleotide sequences are shown in SEQ ID NOs: 111-114. Full length heavy chain amino acid sequences encoded by optimized heavy chain nucleotide sequences are shown in SEQ ID NOs: 115-117. Other antibodies of the invention include amino acids or nucleic acids that have been mutated, yet have at least 60, 70, 80, 90, 95, 96, 97, 98 or 99 percent identity to the sequences described above.

Since each of these antibodies can bind to DKK1, the $V_H$, $V_L$, full length light chain, and full length heavy chain sequences (nucleotide sequences and amino acid sequences) can be "mixed and matched" to create other anti-DKK1 binding molecules of the invention. DKK1 binding of such "mixed and matched" antibodies can be tested using the binding assays described above and in the Examples (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. The $V_H$, $V_L$, full length light chain, and full length heavy chain sequences of the antibodies of the present invention are particularly amenable for mixing and matching, since these antibodies use $V_H$, $V_L$, full length light chain, and full length heavy chain sequences derived from the same germline sequences and thus exhibit structural similarity.

Accordingly, in one aspect, the invention provides an isolated monoclonal antibody or antigen binding portion thereof having: a $V_H$ region comprising an amino acid sequence selected from the group consisting of SEQ ID NOs: 2-20 and 119; and a $V_L$ region comprising an amino acid sequence selected from the group consisting of SEQ ID NOs: 21-39 and 118; wherein the antibody specifically binds DKK1.

Examples of heavy and light chain combinations include: a $V_H$ region comprising the amino acid sequence of SEQ ID NO: 2 and a $V_L$ region comprising the amino acid sequence of SEQ ID NO: 21; or a $V_H$ region comprising SEQ ID NO: 3 and a $V_L$ region comprising SEQ ID NO: 22; or a $V_H$ region comprising SEQ ID NO: 4 and a $V_L$ region comprising SEQ ID NO: 23; or a $V_H$ region comprising SEQ ID NO: 5 and a $V_L$ region comprising SEQ ID NO: 24; or a $V_H$ region comprising SEQ ID NO: 6 and a $V_L$ region comprising SEQ ID NO: 25; or a $V_H$ region comprising SEQ ID NO: 7 and a $V_L$ region comprising SEQ ID NO: 28; or a $V_H$ region comprising SEQ ID NO: 8 and a $V_L$ region comprising SEQ ID NO: 29; or a $V_H$ region comprising SEQ ID NO: 9 and a $V_L$ region comprising SEQ ID NO: 30; or a $V_H$ region comprising SEQ ID NO: 10 and a $V_L$ region comprising SEQ ID NO: 31; or a $V_H$ region comprising SEQ ID NO: 11 and a $V_L$ region comprising SEQ ID NO: 32; or a $V_H$ region comprising SEQ ID NO: 12 and a $V_L$ region comprising SEQ ID NO: 33; or a $V_H$ region comprising SEQ ID NO: 119 and a $V_L$ region comprising SEQ ID NO: 118.

In another aspect, the invention provides an isolated monoclonal antibody or antigen binding portion thereof having: a full length heavy chain comprising an amino acid sequence selected from the group consisting of SEQ ID NOs: 115-117; and a full length light chain comprising an amino acid sequence selected from the group consisting of SEQ ID NOs: 111-114.

Thus, examples of full length heavy chain and full length light chain combinations, respectively, include: SEQ ID NO: 115 with SEQ ID NO: 111; or SEQ ID NO: 116 with SEQ ID NO: 112; or SEQ ID NO: 117 with SEQ ID NO: 113; or SEQ ID NO: 117 with SEQ ID NO: 114.

In another aspect, the invention provides an isolated monoclonal antibody or antigen binding portion thereof comprising a full length heavy chain encoded by a nucleotide sequence selected from the group consisting of SEQ ID NOs: 101-103; and a full length light chain encoded by a nucleotide sequence selected from the group consisting of SEQ ID NOs: 97-100.

Thus, examples of nucleotides that encode full length heavy and light chains, respectively, that may be combined include: SEQ ID NO: 101 and 97; or SEQ ID NO: 102 and 98; or a SEQ ID NO: 103 and 99; or SEQ ID NO: 103 and 100.

In yet another aspect, the invention provides an isolated monoclonal antibody or antigen binding portion that has been optimized for expression in the cell having: a full length heavy chain comprising a nucleotide sequence selected from the group consisting of SEQ ID NOs: 108-110; and a full length light chain comprising a nucleotide sequence selected from the group consisting of SEQ ID NOs: 104-107.

In yet another aspect, the invention provides antibodies that comprise the heavy chain and light chain CDR1s, CDR2s and CDR3s of the antibodies, or combinations thereof. The amino acid sequences of the $V_H$ CDR1s of the antibodies are shown in SEQ ID NOs: 2-5, 8-11, 20, and 49-56. The amino acid sequences of the $V_H$ CDR2s of the antibodies and are shown in SEQ ID NOs: 2-20 and 57-64. The amino acid sequences of the $V_H$ CDR3s of the antibodies are shown in SEQ ID NOs: 2-20 and 65-72. The amino acid sequences of the $V_L$ CDR1s of the antibodies are shown in SEQ ID NOs: 21-39 and 73-80. The amino acid sequences of the $V_L$ CDR2s of the antibodies are shown in SEQ ID NOs: 21-39 and 81-88. The amino acid sequences of the $V_L$ CDR3s of the antibodies are shown in SEQ ID NOs: 21-39 and 89-96. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to DKK1 and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3 to create other anti-DKK1 binding molecules of the invention. DKK1 binding of such "mixed and matched" antibodies can be tested using the binding assays described above and in the Examples (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). Furthermore, CDR1, CDR2 and/or CDR3 sequence from a particular $V_H$ or $V_L$ sequence may be specifically or randomly mutated to create antibodies that may be tested for affinity or binding characteristics. It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

An isolated monoclonal antibody, or antigen binding portion thereof has: a $V_H$ region CDR1 comprising an amino acid sequence selected from the group consisting of SEQ ID NOs: 2-5, 8-11, 20 and 49-56; a $V_H$ region CDR2 comprising an amino acid sequence selected from the group consisting of SEQ ID NOs: 2-20 and 57-64; a $V_H$ region CDR3 comprising an amino acid sequence selected from the group consisting of SEQ ID NOs: 2-20 and 65-72; a $V_L$ region CDR1 comprising an amino acid sequence selected from the group consisting of SEQ ID NOs: 21-39 and 73-80; a $V_L$ region CDR2 comprising an amino acid sequence selected from the group consisting of SEQ ID NOs: 21-39 and 81-88; and a $V_L$ region CDR3 comprising an amino acid sequence selected from the group consisting of SEQ ID NOs: 21-39 and 89-96; wherein the antibody specifically binds DKK1.

In a certain embodiment, the antibody consists of: a $V_H$ region CDR1 comprising SEQ ID NO: 2; a $V_H$ region CDR2 comprising SEQ ID NO: 6; a $V_H$ region CDR3 comprising SEQ ID NO: 7; a $V_L$ region CDR1 comprising SEQ ID NO: 21; a $V_L$ region CDR2 comprising SEQ ID NO: 22; and a $V_L$ region CDR3 comprising SEQ ID NO: 23.

In another embodiment, the antibody consists of: a $V_H$ region CDR1 comprising SEQ ID NO: 3; a $V_H$ region CDR2 comprising SEQ ID NO: 12; a $V_H$ region CDR3 comprising SEQ ID NO: 13; a $V_L$ region CDR1 comprising SEQ ID NO: 24; a $V_L$ region CDR2 comprising SEQ ID NO: 25; and a $V_L$ region CDR3 comprising SEQ ID NO: 26.

In yet another embodiment, the antibody consists of: a $V_H$ region CDR1 comprising SEQ ID NO: 4; a $V_H$ region CDR2 comprising SEQ $V_H$ ID NO: 14; a $V_H$ region CDR3 comprising SEQ ID NO: 15; a $V_L$ region CDR1 comprising SEQ ID NO: 27; a $V_L$ region CDR2 comprising SEQ ID NO: 28; and a $V_L$ region CDR3 comprising SEQ ID NO: 29.

In another embodiment, the antibody consists of: a $V_H$ region CDR1 comprising SEQ ID NO: 5; a $V_H$ region CDR2 comprising SEQ ID NO: 16; a $V_H$ region CDR3 comprising SEQ ID NO: 17; a $V_L$ region CDR1 comprising SEQ ID NO: 30; a $V_L$ region CDR2 comprising SEQ ID NO: 31; and a $V_L$ region CDR3 comprising SEQ ID NO: 32.

In a certain embodiment, the antibody consists of: a $V_H$ region CDR1 comprising SEQ ID NO: 8; a $V_H$ region CDR2 comprising SEQ ID NO: 18; a $V_H$ region CDR3 comprising SEQ ID NO: 19; a $V_L$ region CDR1 comprising SEQ ID NO: 33; a $V_L$ region CDR2 comprising SEQ ID NO: 34; and a $V_L$ region CDR3 comprising SEQ ID NO: 35.

In another embodiment, the antibody consists of: a $V_H$ region CDR1 comprising SEQ ID NO: 9; a $V_H$ region CDR2 comprising SEQ ID NO: 10; a $V_H$ region CDR3 comprising SEQ ID NO: 11; a $V_L$ region CDR1 comprising SEQ ID NO: $V_H$ 36; a $V_L$ region CDR2 comprising SEQ ID NO: 37; and a $V_L$ region CDR3 comprising SEQ ID NO: 38.

As used herein, a human antibody comprises heavy or $V_L$ regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the neutralizing anti-DKK1/4 composition of the Invention.

For example, the invention provides an isolated monoclonal antibody, or antigen binding portion thereof, comprising a $V_H$ region and a $V_L$ region, wherein: the $V_H$ region comprises an amino acid sequence that is at least 80% homologous to an amino acid sequence selected from the group consisting of SEQ ID NOs: 2-20 and 119; the $V_L$ region comprises an amino acid sequence that is at least 80% homologous to an amino acid sequence selected from the group consisting of SEQ ID NOs: 21-39 and 118; the antibody specifically binds to DKK1 and/or DKK4, and the antibody exhibits at least one of the following functional properties: the antibody neutralizes binding of a DKK1 protein to LRP6, Fz and/or Krm, or the antibody neutralizes binding of a DKK4 protein to LRP, Pz and/or Krm.

In a further example, the invention provides an isolated monoclonal antibody, or antigen binding portion thereof, comprising a full length heavy chain and a full length light chain, wherein: the full length heavy chain comprises an amino acid sequence that is at least 80% homologous to an amino acid sequence selected from the group consisting of SEQ ID NOs: 115-117; the full length light chain comprises an amino acid sequence that is at least 80% homologous to an amino acid sequence selected from the group consisting of SEQ ID NOs: 111-114; the antibody specifically binds to DKK1, and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In another example, the invention provides an isolated monoclonal antibody, or antigen binding portion thereof, comprising a full length heavy chain and a full length light chain, wherein: the full length heavy chain comprises a nucleotide sequence that is at least 80% homologous to a nucleotide sequence selected from the group consisting of SEQ ID NOs: 101-103; the full length light chain comprises a nucleotide sequence that is at least 80% homologous to a nucleotide sequence selected from the group consisting of SEQ ID NOs: 97-100; the antibody specifically binds to DKK1, and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In another example, the invention provides an isolated monoclonal antibody, or antigen binding portion thereof that has been optimized for expression in a cell, comprising a full length heavy chain and a full length light chain, wherein: the full length heavy chain comprises a nucleotide sequence that is at least 80% homologous to a nucleotide sequence selected from the group consisting of SEQ ID NOs: 108-110; the full length light chain comprises a nucleotide sequence that is at least 80% homologous to a nucleotide sequence selected from the group consisting of SEQ ID NOs: 104-107; the antibody specifically binds to DKK1, and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In another example, the invention provides an isolated monoclonal antibody, or antigen binding portion thereof that has been optimized for expression in a cell, comprising a $V_H$ region and a $V_L$ region, wherein: the full length heavy chain comprises a nucleotide sequence that is at least 80% homologous to a nucleotide sequence selected from the group consisting of SEQ ID NO: 121; the full length light chain comprises a nucleotide sequence that is at least 80% homologous to a nucleotide sequence selected from the group consisting of SEQ ID NO: 120; the antibody specifically binds to DKK1, and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In various embodiments, the antibody may exhibit one or more, two or more, or three of the functional properties discussed above. The antibody can be, for example, a human antibody, a humanized antibody or a chimeric antibody.

As used herein, the percent homology between two amino acid sequences or two nucleotide sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used. See http:www.ncbi.nhn.nih.gov.

Antibodies with Conservative Modifications

In certain embodiments, an antibody of the invention has a $V_H$ region consisting of CDR1, CDR2, and CDR3 sequences and a $V_L$ region consisting of CDR1, CDR2, and CDR3 sequences, wherein one or more of these CDR sequences have specified amino acid sequences based on the antibodies described herein or conservative modifications thereof, and wherein the antibodies retain the desired functional properties of the neutralizing anti-DKK1/4 composition of the invention. Accordingly, the invention provides an isolated monoclonal antibody, or antigen binding portion thereof, consisting of a $V_H$ region consisting of CDR1, CDR2, and CDR3 sequences and a $V_L$ region consisting of CDR1, CDR2, and CDR3 sequences, wherein: the $V_H$ regions of CDR1 is sequences consisting of amino acid sequences selected from the group consisting of amino acid sequences of SEQ ID NOs: 2-5, 8-11, 20, 49-56, and conservative modifications thereof; the $V_H$ region of CDR2 is sequences consisting of amino acid sequences selected from the group consisting of amino acid sequences of SEQ ID NOs: 2-20, 57-64, and conservative modifications thereof; the $V_H$ region of CDR3 is sequences consisting of amino acid sequences selected from the group consisting of amino acid sequences of SEQ ID NOs: 2-20, 65-72, and conservative modifications thereof; the $V_L$ regions of CDR1 is sequences consisting of amino acid sequences selected from the group consisting of amino acid sequences of SEQ ID NOs: 21-39, 73-80, and conservative modifications thereof; the $V_L$ regions of CDR2 is sequences consisting of amino acid sequences selected from the group consisting of amino acid sequences of SEQ ID NOs: 21-39, 81-88, and conservative modifications thereof; the $V_L$ regions of CDR3 is sequences consisting of amino acid sequences selected from the group consisting of amino acid sequences of SEQ ID NOs: 21-39, 89-96, and conservative modifications thereof; the antibody specifically binds to DKK1; and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In various embodiments, the antibody may exhibit one or more, two or more, or three or more of the functional properties listed discussed above. Such antibodies can be, for example, human antibodies, humanized antibodies or chimeric antibodies.

In other embodiments, an antibody of the invention has a full length heavy chain sequence and a full length light chain sequence, wherein one or more of these sequences have specified amino acid sequences based on the antibodies described herein or conservative modifications thereof, and wherein the antibodies retain the desired functional properties of the neutralizing anti-DKK1/4 composition of the invention. Accordingly, the invention provides an isolated monoclonal antibody, or antigen binding portion thereof, consisting of a full length heavy chain and a full length light chain wherein: the full length heavy chain has amino acid sequences selected from the group of SEQ ID NOs: 115-117, and conservative modifications thereof; and the full length light chain has amino acid sequences selected from the group of SEQ ID NOs: 111-114, and conservative modifications thereof; the antibody specifically binds to DKK1; and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In various embodiments, the antibody may exhibit one or more, two or more, or three or more of the functional properties listed discussed above. Such antibodies can be, for example, human antibodies, humanized antibodies or chimeric antibodies.

In other embodiments, an antibody of the invention optimized for expression in a cell has a $V_H$ region sequence and a $V_L$ region sequence, wherein one or more of these sequences have specified amino acid sequences based on the antibodies described herein or conservative modifications thereof, and wherein the antibodies retain the desired functional properties of the neutralizing anti-DKK1/4 composition of the invention. Accordingly, the invention provides an isolated monoclonal antibody, or antigen binding portion thereof, consisting of a $V_H$ region and a $V_L$ region wherein: the $V_H$ region has amino acid sequences selected from the group of SEQ ID NO: 119, and conservative modifications thereof; and the $V_L$ region has amino acid sequences selected from the group of SEQ ID NOs: 118, and conservative modifications thereof; the antibody specifically binds to DKK1; and the antibody exhibits at least one of the following functional properties: the antibody inhibits binding DKK1 protein to the DKK1 receptor or the antibody inhibits DKK1 receptor binding preventing or ameliorating osteolysis or the antibody inhibits DKK1 receptor binding preventing or ameliorating osteolytic lesions or the antibody inhibits DKK1 receptor binding preventing or ameliorating cancer.

In various embodiments, the antibody may exhibit one or more, two or more, or three or more of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Neutralizing Anti-DKK1/4 Composition of the Invention In another embodiment, the invention provides antibodies that bind to the same epitope as do the various neutralizing anti-DKK1/4 composition of the invention provided herein.

Such additional antibodies can be identified based on their ability to cross-compete (e.g., to competitively inhibit the binding of, in a statistically significant manner) with other antibodies of the invention in standard DKK1 binding assays. The ability of a test antibody to inhibit the binding of antibodies of the present invention to human DKK1 demonstrates that the test antibody can compete with that antibody for binding to human DKK1; such an antibody may, according to non-limiting hypotheses, bind to the same or a related (e.g., a structurally similar or spatially proximal) epitope on human DKK1 as the antibody with which it competes. In a certain embodiment, the antibody that binds to the same epitope on human DKK1 as the antibodies of the present invention is a human monoclonal antibody. Such human monoclonal antibodies can be prepared and isolated as described in the Examples.

Camelid and Other Heavy Chain Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for DKK1. In certain embodiments herein, the camelid antibody or nanobody is naturally produced in the camelid animal, i.e., is produced by the camelid following immunization with DKK1 or a peptide fragment thereof, using techniques described herein for other antibodies. Alternatively, the neutralizing anti-DKK1/4 camelid nanobody is engineered, i.e., produced by selection for example from a library of phage displaying appropriately mutagenized camelid nanobody proteins using panning procedures with DKK1 and/or DKK4 as a target as described in the examples herein. Engineered nanobodies can further be customized by genetic engineering to have a half life in a recipient subject of from 45 minutes to two weeks.

In addition to Camelid antibodies, heavy chain antibodies occur naturally in other animal including but not limited to, e.g., certain species of shark and pufferfish (see, e.g., PCT publication WO 03/014161). Although variable domains derived from such heavy chain antibodies may be used in the invention, the use of Camelid-derived heavy chain antibodies and/or of the variable domain sequences thereof is preferred optimization, humanization, humaneering, and the like and/or for clinical use in humans.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i. e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a $V_H$ region comprising CDR1 sequences having an amino acid sequence selected from the group consisting of SEQ ID NOs: 2-5, 8-11, 20, 49-56; CDR2 sequences having an amino acid sequence selected from the group consisting of SEQ ID NOs: 2-20 and 57-64; CDR3 sequences having an amino acid sequence selected from the group consisting of SEQ ID NOs: 2-20 and 65-72, respectively; and a $V_L$ region having CDR1 sequences having an amino acid sequence selected from the group consisting of SEQ ID NOs: 21-39 and 73-80; CDR2 sequences having an amino acid sequence selected from the group consisting of SEQ ID NOs: 21-39 and 81-88; and CDR3 sequences consisting of an amino acid sequence selected from the group consisting of SEQ ID NOs: 21-39 and 89-96, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and $V_L$ region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated neutralizing anti-DKK1/4 composition, or antigen binding portions thereof, consisting of a $V_H$ region having: a $V_H$ CDR1 region consisting of an amino acid sequence selected from the group having SEQ ID NOs: 2-5, 8-11, 20, 49-56 or an amino acid sequence having one, two, three, four or five amino acid substitutions, deletions or additions as compared to SEQ ID NOs: 2-5, 8-11, 20, 49-56; a $V_H$ CDR2 region having an amino acid sequence selected from the group consisting of SEQ ID NOs: 2-20 and 57-64, or an amino acid sequence having one, two, three, four or five amino acid substitutions, deletions or additions as compared to SEQ ID NOs: 2-20 and 57-64; a $V_H$ CDR3 region having an amino acid sequence selected from the group consisting of SEQ ID NOs: 2-20 and 65-72, or an amino acid sequence having one, two, three, four or five amino acid substitutions, deletions or additions as compared to SEQ ID NOs: 2-20 and 65-72; a $V_L$ CDR1 region having an amino acid sequence selected from the group consisting of SEQ ID NOs: 21-39 and 73-80, or an amino acid sequence having one, two, three, four or five amino acid substitutions, deletions or additions as compared to SEQ ID NOs: 21-39 and 73-80; a $V_L$ CDR2 region having an amino acid sequence selected from the group consisting of SEQ ID NOs: 21-39 and 81-88, or an amino acid sequence having one, two, three, four or five amino acid substitutions, deletions or additions as compared to SEQ ID NOs: 21-39 and 81-88; and a $V_L$ CDR3 region having an amino acid sequence selected from the group consisting of SEQ ID NOs: 21-39 and 89-96, or an amino acid sequence having one, two, three, four or five amino acid substitutions, deletions or additions as compared to SEQ ID NOs: 21-39 and 89-96.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "back mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis. Such "back mutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et at.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et at.

In another embodiment, one or more amino acid residues are altered to thereby alter the ability of the antibody to fix complement. This approach is described further in PCT Publication WO 94/29351 by Bodmer et at.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for an "antigen'. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Non-Immunoglobulin Scaffolds

A wide variety of antibody/immunoglobulin frameworks or scaffolds can be employed so long as the resulting polypeptide includes at least one binding region which is specific for the target protein. Such frameworks or scaffolds include the five main idiotypes of human immunoglobulins, or fragments thereof (such as those disclosed elsewhere herein), and include immunoglobulins of other animal species, preferably having humanized aspects. Single heavy-chain antibodies such as those identified in camelids and/or shark are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO: 1 or SEQ ID NO:122. Such compounds are known herein as "polypeptides comprising a target-specific binding region". Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (*Pieris* Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

(i) Adnectins—Compound Therapeutics

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—*Pieris*

Anticalins® are products developed by the company *Pieris* ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris Brassicae* has been used to develop anticalins by mutagenizing the set of four loops. One example of a patent application describing "anticalins" is PCT WO 199916873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in W0200104144 and examples of "ubiquitin-like" proteins are described in WO2004106368.

Methods of Engineering Antibodies

As discussed above, the anti-DKK1 antibodies having $V_H$ and $V_L$ sequences or full length heavy and light chain sequences shown herein can be used to create new anti-DKK1/4 antibodies by modifying full length heavy chain and/or light chain sequences, $V_H$ and/or $V_L$ sequences, or the constant region(s) attached thereto. Thus, in another aspect of the invention, the structural features of an anti-DKK1 antibody of the invention are used to create structurally related anti-DKK1/4 antibodies that retain at least one functional property of the antibodies of the invention, such as binding to human DKK1 or DKK4 or both and also inhibiting one or more functional properties of DKK1 or DKK4 or both.

For example, one or more CDR regions of the antibodies of the present invention, or mutations thereof, can be combined recombinantly with known framework regions and/or other CDRs to create additional, recombinantly-engineered, anti-DKK1 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-DKK1 antibody consisting of: a $V_H$ region antibody sequence having a CDR1 sequence selected from the group consisting of SEQ ID NOs: 2-5, 8-11, 20, 49-56, a CDR2 sequence selected from the group consisting of SEQ ID NOs: 2-20 and 57-64 and/or a CDR3 sequence selected from the group consisting of SEQ ID NOs: 2-20 and 65-72; and a $V_L$ region antibody sequence having a CDR1 sequence selected from the group consisting of SEQ ID NOs: 21-39 and 73-80, a CDR2 sequence selected from the group consisting of SEQ ID NOs: 21-39 and 81-88 and/or a CDR3 sequence selected from the group consisting of SEQ ID NOs: 21-39 and 89-96; altering at least one amino acid residue within the $V_H$ region antibody sequence and/or the $V_L$ region antibody sequence to create at least one altered antibody sequence; and expressing the altered antibody sequence as a protein.

Accordingly, in another embodiment, the invention provides a method for preparing an anti-DKK1 antibody consisting of: a full length heavy chain antibody sequence having a sequence selected from the group of SEQ ID NOs: 115-117; and a full length light chain antibody sequence having a sequence selected from the group of SEQ ID NOs: 111-114; altering at least one amino acid residue within the full length heavy chain antibody sequence and/or the full length light chain antibody sequence to create at least one altered antibody sequence; and expressing the altered antibody sequence as a protein.

In another embodiment, the invention provides a method for preparing a neutralizing anti-DKK1/4 composition optimized for mammalian expression consisting of: a $V_H$ region antibody sequence having a sequence selected from the group of SEQ ID NO: 119; and a $V_L$ region antibody sequence having a sequence selected from the group of SEQ ID NO: 118; altering at least one amino acid residue within the $V_H$ region antibody sequence and/or the $V_L$ region antibody sequence to create at least one altered antibody sequence; and expressing the altered antibody sequence as a protein.

Standard molecular biology techniques can be used to prepare and express the altered antibody sequence. The antibody encoded by the altered antibody sequence(s) is one that retains one, some or all of the functional properties of the neutralizing anti-DKK1/4 compositions described herein, which functional properties include, but are not limited to, specifically binding to human DKK1; and the antibody exhibits at least one of the following functional properties: the antibody inhibits binding of DKK1 protein to the DKK1 receptor, or the antibody inhibits DKK1 receptor binding preventing or ameliorating osteolysis, or the antibody inhibits DKK1 receptor binding thereby preventing or ameliorating osteolytic lesions, or the antibody inhibits DKK1 receptor binding preventing or ameliorating cancer.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-DKK1 antibody coding sequence and the resulting modified anti-DKK1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

The Fc constant region of an antibody is critical for determining serum half-life and effector functions, i.e., antibody dependent cell cytotoxicity (ADCC) or complement dependent cytotoxicity (CDC) activities. One can engineer specific mutants of the Fc fragment to alter the effector function and/or serum half-life (see, e.g., Xencor technology, see also, e.g., WO2004029207).

One method to alter effector function and serum half-life of an antibody is to graft the variable region of an antibody fragment with an Fc fragment having the appropriate effector function. IgG1 or IgG4 isotypes can be selected for cell killing activity, whereas IgG2 isotype can be used for silent or neutralizing antibodies (with no cell killing activity).

Silent antibodies with long serum half-life can be obtained by making chimeric fusion of variable regions of an antibody with a serum protein such as HSA or a protein binding to such serum protein, such HSA-binding protein.

Effector functions can also be altered by modulating the glycosylation pattern of the antibody. Glycart (e.g., U.S. Pat. No. 6,602,684), Biowa (e.g., U.S. Pat. No. 6,946,292) and Genentech (e.g WO03/035835) have engineered mammalian cell lines to produce antibodies with increased or decreased effector function. Especially, non fucosylated antibodies will have enhanced ADCC activities. Glycofi has also developed yeast cell lines capable of producing specific glycoforms of antibodies.

Nucleic Acid Molecules Encoding Antibodies of the Invention

Another aspect of the invention pertains to nucleic acid molecules that encode the antibodies of the invention. Examples of full length light chain parental nucleotide sequences are shown in SEQ ID NOs: 97-100. Examples of full length heavy chain parental nucleotide sequences are shown in SEQ ID NOs: 101-103. Examples of full length light chain nucleotide sequences optimized for expression in a cell are shown in SEQ ID NOs: 104-107. Examples of full length heavy chain nucleotide sequences optimized for expression in a cell are shown in SEQ ID NOs: 108-110.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, an IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence $(Gly4-Ser)_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Production of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against DKK1 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-DKK1 antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-DKK1 antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-DKK1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Human antibody libraries screens may be used to identify an antibody of the invention. Choice of screening technologies include, but are not limited to, e.g. phage display (Morphosys), the type of libraries (e.g., HuCal library from Morphosys), affinity maturation technology and further codon optimization sequence.

Generation of Human Monoclonal Antibodies Against DKK1.

Purified recombinant human DKK1 derived from *E. coli*, baculovirus or HEK-EBNA cells, or purified recombinant human DKK1 conjugated to keyhole limpet hemocyanin (KLH), is used as the antigen.

Fully human monoclonal antibodies to DKK1 are prepared using HCo7, HCo12 and HCo17 strains of HuMab transgenic mice and the KM strain of transgenic transchromosomic mice, each of which express human antibody genes. In each of these mouse strains, the endogenous mouse kappa light chain gene can be homozygously disrupted as described in Chen et al., 1993 EMBO J. 12:811-820 and the endogenous mouse heavy chain gene can be homozygously disrupted as described in Example 1 of PCT Publication WO 01109187. Each of these mouse strains carries a human kappa light chain transgene, KCo5, as described in Fishwild et al., 1996 Nature Biotechnology 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187. The HCo17 stain carries the HCo17 human heavy chain transgene. The KNM strain contains the SC20 transchromosome as described in PCT Publication WO 02/43478.

To generate fully human monoclonal antibodies to DKK1, HuMab mice and KM mice are immunized with purified recombinant DKK1 derived from *E. coli* or DKK1-KLH conjugate as antigen. General immunization schemes for HuMab mice are described in Lonberg, N. et al., 1994 Nature 368 (6474): 856-859; Fishwild, D. et al., 1996 Nature Biotechnology 14:845-851 and PCT Publication WO 98/24884. The mice are 6-16 weeks of age upon the first infusion of antigen. A purified recombinant preparation (5-50 μg) of DKK1 antigen (e.g., purified from transfected *E. coli* cells expressing DKK1) is used to immunize the HuMab mice and KM mice intraperitonealy, subcutaneously (Sc) or by footpad injection.

Transgenic mice are immunized twice with antigen in complete Freund's adjuvant or Ribi adjuvant either intraperitonealy (IP), subcutaneously (Sc) or by footpad (FP), followed by 3-21 days IP, Sc or FP immunization (up to a total of 11 immunizations) with the antigen in incomplete Freund's or Ribi adjuvant. The immune response is monitored by retroorbital bleeds. The plasma is screened by ELISA, and mice with sufficient titers of anti-DKK1 human immunogolobulin are used for fusions. Mice are boosted intravenously with antigen 3 and 2 days before sacrifice and removal of the spleen. Typically, 10-35 fusions for each antigen are performed. Several dozen mice are immunized for each antigen. A total of 82 mice of the HCo7, HCo12, HCo17 and KM mice strains are immunized with DKK1.

To select HuMab or KM mice producing antibodies that bound DKK1, sera from immunized mice can be tested by ELISA as described by Fishwild, D. et al., 1996. Briefly, microtiter plates are coated with purified recombinant DKK1 from *E. coli* at 1-2 μg/ml in PBS, 50 μl/wells incubated 4° C. overnight then blocked with 200 μl/well of 5% chicken serum in PBS/Tween (0.05%). Dilutions of plasma from DKK1-immunized mice are added to each well and incubated for 1-2 hours at ambient temperature. The plates are washed with PBS/Tween and then incubated with a goat-anti-human IgG Fc polyclonal antibody conjugated with horseradish peroxidase (HRP) for 1 hour at room temperature. After washing, the plates are developed with ABTS substrate (Sigma, A-1888, 0.22 mg/ml) and analyzed by spectrophotometer at OD 415-495. Mice that developed the highest titers of anti-DKK1 antibodies are used for fusions. Fusions are performed and hybridoma supernatants are tested for anti-DKK1 activity by ELISA.

The mouse splenocytes, isolated from the HuMab mice and KM mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of SP2/0 nonsecreting mouse myeloma cells (ATCC, CRL 1581) with 50% PEG (Sigma). Cells are plated at approximately $1\times10^5$/well in flat bottom microtiter plate, followed by about two week incubation in selective medium containing 10% fetal bovine serum, 10% P388D 1(ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mglnni gentamycin and 1×HAT (Sigma, CRL P-7185). After 1-2 weeks, cells are cultured in medium in which the HAT is replaced with HT. Individual wells are then screened by ELISA for human anti-DKK1 monoclonal IgG antibodies. Once extensive hybridoma growth occurred, medium is monitored usually after 10-14 days. The antibody secreting hybridomas are replated, screened again and, if still positive for human IgG, anti-DKK1 monoclonal antibodies are subcloned at least twice by limiting dilution. The stable subclones are then cultured in vitro to generate small amounts of antibody in tissue culture medium for further characterization.

Immunization of Human Ig Mice

When human Ig mice are used to raise human antibodies of the invention, such mice can be immunized with a purified or enriched preparation of DKK1 antigen and/or recombinant DKK1, or an DKK1 fusion protein, as described by Lonberg, N. et al., 1994 Nature 368(6474): 856-859; Fishwild, D. et al., 1996 Nature Biotechnology 14: 845-851; and PCT Publication. WO 98124884 and WO 01/14424. The mice can be 6-16 weeks of age upon the first infusion. For example, a purified or recombinant preparation (5-50 μg) of DKK1 antigen can be used to immunize the human Ig mice intraperitoneally.

Detailed procedures to generate fully human monoclonal antibodies to DKK1 are described above. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-DKK1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo 12 transgene can be bred together into a single mouse having two different human heavy chain transgenes (HCo7/HCo12).

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −a 80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and $V_H$ regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and antigen binding antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P.A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Pharmaceutical Compositions

In another aspect, the present invention provides a composition, e.g., a pharmaceutical composition, containing one or a combination of a neutralizing anti-DKK1/4 composition, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents.

For example, the combination therapy can include an anti-DKK1 antibody of the present invention combined with at least one other anti-inflammatory or anti-osteoprotic agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 per cent to about ninety-nine percent of active ingredient, from about 0.1 per cent to about 70 per cent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 200 mg/kg, and more usually 0.01 to 50 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-20 mg/kg. An exemplary treatment regime entails administration once per week, once every two weeks, once every three weeks, once every four weeks, once a month, once every 3 months or once every three to 6 months. Dosage regimens for an anti-DKK1 antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring patient blood levels of antibody to the target antigen or of some biomarker such as OCN, OPG or P1NP. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-DKK1 antibody of the invention can results in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. No. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun 153:1038); antibodies (P. G. Bloeman et al., 1995 FEBS Lett. 357:140; M. Owais et al., 1995 Antimicrob. Agents Chernother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

The Combinations

The invention further relates to a method of preventing or treating proliferative diseases or diseases, such as a cancer, in a mammal, particularly a human, with a combination of pharmaceutical agents which comprises (a) a neutralizing anti-DKK1/4 composition; and (b) one or more pharmaceutically active agents.

The invention further relates to pharmaceutical compositions comprising:

(a) a neutralizing anti-DKK1/4 composition;

(b) a pharmaceutically active agent; and (c) a pharmaceutically acceptable carrier.

The present invention further relates to a commercial package or product comprising:

(a) a pharmaceutical formulation of a neutralizing anti-DKK1/4 composition; and (b) a pharmaceutical formulation of a pharmaceutically active agent for simultaneous, concurrent, separate or sequential use.

The Pharmaceutically Active Agents

The term "pharmaceutically active agents" is a broad one covering many pharmaceutically active agents having different mechanisms of action. Combinations of some of these with DKK1/4 neutralizing antibodies/compositions can result in improvements in cancer therapy. Generally, pharmaceutically active agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are anti-mitotic agents.

By the term "pharmaceutically active agent" is meant especially any pharmaceutically active agent other than a neutralizing anti-DKK1/4 composition or a derivative thereof. It includes, but is not limited to:

i. an aromatase inhibitor;

ii. an anti-estrogen, an anti-androgen or a gonadorelin agonist;

iii. a topoisomerase I inhibitor or a topoisomerase II inhibitor;

iv. a microtubule active agent, an alkylating agent, an antineoplastic anti-metabolite or a platin compound;

v. a compound targeting/decreasing a protein or lipid kinase activity or a protein or lipid phosphatase activity, a further anti-angiogenic compound or a compound which induces cell differentiation processes;

vi. monoclonal antibodies;

vii. a cyclooxygenase inhibitor, a bisphosphonate, a heparanase inhibitor, a biological response modifier;

viii. an inhibitor of Ras oncogenic isoforms;

ix. a telomerase inhibitor;

x. a protease inhibitor, a matrix metalloproteinase inhibitor, a methionine aminopeptidase inhibitor, or a proteasome inhibitor;

xi. agents used in the treatment of hematologic malignancies or compounds which target, decrease or inhibit the activity of Flt-3;

xii. an HSP90 inhibitor;

xiii. antiproliferative antibodies;

xiv. a histone deacetylase (HDAC) inhibitor;

xv. a compound which targets, decreases or inhibits the activity/function of serine/threonine mTOR kinase;

xvi. a somatostatin receptor antagonist;

xvii. an anti-leukemic compound;

xviii. tumor cell damaging approaches;

xix. an EDG binder;

xx. a ribonucleotide reductase inhibitor;

xxi. an S-adenosylmethionine decarboxylase inhibitor;

xxii. a monoclonal antibody of VEGF or VEGFR;

xxiii. photodynamic therapy;

xxiv. an angiostatic steroid;

xxv. an implant containing corticosteroids;

xxvi. an AT1 receptor antagonist; and xxvii. an ACE inhibitor.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketokonazole, vorozole, fadrozole, anastrozole and letrozole. Exemestane is marketed as AROMASIN; formestane as LENTARON; fadrozole as AFEMA; anastrozole as ARIMIDEX; letrozole as FEMARA or FEMAR; and aminoglutethimide as ORIMETEN. A combination of the invention comprising a pharmaceutically active agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered in the form as it is marketed, e.g., NOLVADEX; and raloxifene hydrochloride is marketed as EVISTA. Fulvestrant can be formulated as disclosed in U.S. Pat. No. 4,659,516 and is marketed as FASLODEX. A combination of the invention comprising a pharmaceutically active agent which is an anti-estrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and is marketed as ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound Al in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX, daunorubicin, including liposomal formulation, e.g., DAUNOSOME, epirubicin, idarubicin and nemorubicin; the anthraquinones mitoxantrone and losoxantrone; and the podophillotoxines etoposide and teniposide. Etoposide is marketed as ETOPOPHOS; teniposide as VM 26-BRISTOL; doxorubicin as ADRIBLASTIN or ADRIAMYCIN; epirubicin as FARMORUBICIN; idarubicin as ZAVEDOS; and mitoxantrone as NOVANTRON.

The term "microtubule active agent" as used herein, relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine and epothilonesand derivatives thereof, e.g., epothilone B or a derivative thereof. Paclitaxel is marketed as TAXOL; docetaxel as TAXOTERE; vinblastine sulfate as VINBLASTIN R.P; and vincristine sulfate as FARMISTIN. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE; ONXOL, CYTOTAX Discodermolide can be obtained, e.g., as disclosed in U.S. Pat. No. 5,010,099. Also included are Epotholine derivatives which are disclosed in U.S. Pat. No. 6,194,181, WO 98/10121, WO 98/25929, WO 98/08849, WO 99/43653, WO 98/22461 and WO 00/31247. Especially preferred are Epotholine A and/or B.

The term “alkylating agent”, as used herein, includes, but is not limited to, cyclophosphamide, ifosfamide, melphalan or nitrosourea (BCNU or Gliadel), or temozolamide (TEMODAR).Cyclophosphamide can be administered, e.g., in the form as it is marketed, e.g., under the trademark CYCLOSTIN; and ifosfamide as HOLOXAN.

The term “anti-neoplastic anti-metabolite” includes, but is not limited to, 5-fluorouracil (5-FU); capecitabine; gemcitabine; DNA de-methylating agents, such as 5-azacytidine and decitabine; methotrexate; edatrexate; and folic acid antagonists such as, but not limited to, pemetrexed. Capecitabine can be administered, e.g., in the form as it is marketed, e.g., under the trademark XELODA; and gemcitabine as GEMZAR.

The term “platin compound”, as used herein, includes, but is not limited to, carboplatin, cis-platin, cisplatinum, oxaliplatin, Satraplatin and platinum agents such as ZD0473. Carboplatin can be administered, e.g., in the form as it is marketed, e.g., CARBOPLAT; and oxaliplatin as ELOXATIN.

The term “compounds targeting/decreasing a protein or lipid kinase activity; or a protein or lipid phosphatase activity; or further anti-angiogenic compounds”, as used herein, includes, but is not limited to, protein tyrosine kinase and/or serine and/or theroine kinase inhibitors or lipid kinase inhibitors, for example:

i) compounds targeting, decreasing or inhibiting the activity of the vascular endothelial growth factor-receptors (VEGF), such as compounds which target, decrease or inhibit the activity of VEGF, especially compounds which inhibit the VEGF receptor, such as, but not limited to, 7H-pyrrolo[2,3-d]pyrimidine derivatives (AEE788); BAY 43-9006; isolcholine compounds disclosed in WO 00/09495 such as (4-tert-butyl-phenyl)-94-pyridin-4-ylmethyl-isoquinolin-1-yl)-amine (AAL881); and ii) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;

iii) compounds targeting, decreasing or inhibiting the activity of the fibroblast growth factor-receptors (FGFR);

iv) compounds targeting, decreasing or inhibiting the activity of the insulin-like growth factor receptor 1 (IGF-1R), such as compounds which target, decrease or inhibit the activity of IGF-IR, especially compounds which inhibit the IGF-1R receptor. Compounds include but are not limited to the compounds disclosed in WO 02/092599 and derivatives thereof of 4-amino-5-phenyl-7-cyclobutyl-pyrrolo[2,3-d]pyrimidine derivatives (AEW541);

v) compounds targeting, decreasing or inhibiting the activity of the Trk receptor tyrosine kinase family;

vi) compounds targeting, decreasing or inhibiting the activity of the Axl receptor tyrosine kinase family;

vii) compounds targeting, decreasing or inhibiting the activity of the c-Met receptor;

viii) compounds targeting, decreasing or inhibiting the activity of the Ret receptor tyrosine kinase;

ix) compounds targeting, decreasing or inhibiting the activity of the Kit/SCFR receptor tyrosine kinase;

x) compounds targeting, decreasing or inhibiting the activity of the C-kit receptor tyrosine kinases (part of the PDGFR family), such as compounds which target, decrease or inhibit the activity of the c-Kit receptor tyrosine kinase family, especially compounds which inhibit the c-Kit receptor, e.g., imatinib;

xi) compounds targeting, decreasing or inhibiting the activity of members of the c Ab1 family and their gene-fusion products, e.g., BCR-Ab1 kinase, such as compounds which target decrease or inhibit the activity of c-AbI family members and their gene fusion products, e.g., a N-phenyl-2-pyrimidine-amine derivative, e.g., imatinib, PD180970, AG957, NSC 680410 or PD173955 from ParkeDavis; BMS354825 xii) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352 or QAN697, a P13K inhibitor;

xiii) compounds targeting, decreasing or inhibiting the activity of protein-tyrosine kinase, such as imatinib mesylate (GLEEVEC); tyrphostin or pyrymidylaminobenzamide and derivatives thereof (AMN107). A tyrphostin is preferably a low molecular weight (Mr<1500) compound, or a pharmaceutically acceptable salt thereof, especially a compound selected from the benzylidenemalonitrile class or the S arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; AG957 and adaphostin (4-{[(2,5-dihydroxyphenyl)methyl]amino}-benzoic acid adamantyl ester, NSC 680410, adaphostin);

xiv) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF-related ligands, and are in particular those compounds, proteins or monoclonal antibodies generically and specifically disclosed in WO 97/02266, e.g., the compound of Example 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347, e.g., compound known as CP 358774, WO 96/33980, e.g., compound ZD 1839; and WO 95/03283, e.g., compound ZM105180, e.g., trastuzumab (HERCEPTIN®), cetuximab, Iressa, OSI-774, CI 1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541, erlotinib and gefitinib. Erlotinib can be administered in the form as it is marketed, e.g. TARCEVA, and gefitinib as IRESSA, human monoclonal antibodies against the epidermal growth factor receptor including ABX-EGFR; and xv) Compounds which target, decrease or inhibit the activity/function of serine/theronine mTOR kinase are especially compounds, proteins or antibodies which target/inhibit members of the mTOR kinase family, e.g., RAD, RAD001, CCI-779, ABT578, SAR543, rapamycin and derivatives/analogs thereof, AP23573 and AP23841 from Ariad, everolimus (CERTICAN) and sirolimus. CERTICAN (everolimus, RAD) an investigational novel proliferation signal inhibitor that prevents proliferation of T-cells and vascular smooth muscle cells.

When referring to antibody, it is to include intact monoclonal antibodies, nanobodies, polyclonal antibodies, multispecific antibodies formed from at least 2 intact antibodies, and antibodies fragments so long as they exhibit the desired biological activity.

The phrase "compound which targets, decreases or inhibits the activity of a protein or lipid phosphatase" as used herein includes but is not limited to inhibitors of phosphatase 1, phosphatase 2A, PTEN or CDC25, e.g., okadaic acid or a derivative thereof The term "monoclonal antibodies", as used herein, includes, but is not limited to bevacizumab, cetuximab, trastuzumab, Ibritumomab tiuxetan, denosumab, anti-CD40, anti-GM-CSF, and tositumomab and iodine I 131. Bevacizumab can be administered in the form as it is marketed, e.g. AVASTIN; cetuximab as ERBITUX; trastuzumab as HERCEPTIN; Rituximab as MABTHERA; Ibritumomab tiuxetan as ZEVULIN; anti-RANKL as denosumab (AMG 162), anti-CD40 as HCD122 (U.S. patent application 2002-0106371), and tositumomab and iodine I 131 as BEXXAR.

The phrase "further anti-angiogenic compounds" includes but is not limited to compounds having another mechanism for their activity, e.g., unrelated to protein or lipid kinase inhibition, e.g., thalidomide (THALOMID) and TNP-470.

The phrase "compounds which induce cell differentiation processes" as used herein, include but is not limited to retinoic acid, α-, γ- or δ-tocopherol or α-, γ- or δ-tocotrienol.

The term "cyclooxygenase inhibitor" as used herein includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid, lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., DIDRONEL; "clodronic acid" as BONEFOS; "tiludronic acid" as SKELID; "pamidronic acid" as AREDIA; "alendronic acid" as FOSAMAX; "ibandronic acid" as BONDRANAT; "risedronic acid" as ACTONEL; and "zoledronic acid" as ZOMETA.

The term "heparanase inhibitor", as used herein, refers to compounds which target, decrease or inhibit heparin sulphate degradation. The term includes, but is not limited to, PI 88.

The term "biological response modifier", as used herein, includes, but is not limited to lymphokine or interferons, e.g., interferon γ.

The term "inhibitor of Ras oncogenic isoforms", as used herein, includes, but is not limited to H-Ras, K-Ras or N-Ras, as used herein, refers to compounds which target, decrease or inhibit the oncogenic activity of Ras, e.g., a farnesyl transferase inhibitor (FTI), e.g., L-744832, DK8G557 or R115777 (ZARNESTRA).

The term "telomerase inhibitor", as used herein, includes, but is not limited to compounds which target, decrease or inhibit the activity of telomerase. Compounds which target, decrease or inhibit the activity of telomerase are especially compounds which inhibit the telomerase receptor, e.g., telomestatin.

The term "matrix metalloproteinase inhibitor" or (MMP inhibitor), as used herein, includes, but is not limited to, collagen peptidomimetic and non-peptidomimetic inhibitors; tetracycline derivatives, e.g., hydroxamate peptidomimetic inhibitor batimastat; and its orally-bioavailable analogue marimastat (BB-2516), prinomastat (AG3340), metastat (NSC 683551) BMS 279251, BAY 12-9566, TAA211, MMI270B or AAJ996.

The term "methionine aminopeptidase inhibitor", as used herein, includes, but is not limited to, compounds which target, decrease or inhibit the activity of methionine aminopeptidase. Compounds which target, decrease or inhibit the activity of methionine aminopeptidase are, e.g., bengamide or a derivative thereof.

The term "proteasome inhibitors", as used herein, includes compounds which target, decrease or inhibit the activity of the proteosome. Compounds which target, decrease or inhibit the activity of the proteosome include, but are not limited to, PS-341; MLN 341. bortezomib or Velcade.

The phrase "agent used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

The phrase "compounds which target, decrease or inhibit the activity of Flt-3" as used herein, includes, but is not limited to compounds, proteins or antibodies which inhibit Flt-3, e.g., N-benzoyl-staurosporine, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, e.g., 17-allylamino,17-demethoxygeldanamycin (17AAG), a geldanamycin derivative; other geldanamycin-related compounds; radicicol and HDAC inhibitors.

The term "an antiproliferative antibody" as used herein, includes, but is not limited to trastuzumab (HERCEPTIN), trastuzumab-DM1, erlotinib (TARCEVA), bevacizumab (AVASTIN), rituximab (RITUXAN), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "HDAC inhibitor", as used herein relates to relates to compounds which inhibit the histone deacetylase and which possess anti-proliferative activity. This includes but is not limited to compounds disclosed in WO 02/22577, especially N-hydroxy-3-[4-[[(2-hydroxyethyl)[2-(1H-indol-3-yl)ethyl]-amino]methyl]phenyl]-2E-2-propenamide, and N-hydroxy-3-[4-[[[2-(2-methyl-1H-indol-3-yl)-ethyl]-amino]methyl]phenyl]-2E-2-propenamide and pharmaceutically acceptable salts thereof (LBH589). It further especially includes Suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, Oxamflatin, apicidin, Depsipeptide; depudecin and trapoxin.

The phrase "compound which targets, decreases or inhibits the activity/function of serine/theronine mTOR kinase" as used herein, includes but is not limited to compounds, proteins or antibodies which target/inhibit members of the mTOR kinase family, e.g., RAD, RAD001, CCI-779, ABT578, SAR543, rapamycin and derivatives/analogs thereof, AP23573 and AP23841 from Ariad, everolimus (CERTICAN) and sirolimus (RAPAMUNE), CCI-779 and ABT578. CERTICAN (everolimus, RAD) an investigational novel proliferation signal inhibitor that prevents proliferation of T-cells and vascular smooth muscle cells.

The term "somatostatin receptor antagonist", as used herein, includes, but is not limited to, agents which target, treat or inhibit the somatostatin receptor, such as octreoride and SOM230.

The term "anti-leukemic compound" as used herein, includes, but is not limited to Ara-C, a pyrimidine analog, which is the 2'-α-hydroxy ribose (arabinoside) derivative of deoxycytidine. Also included is the purine analog of hypoxanthine, 6-mercaptopurine (6-MP) and fludarabine phosphate.

The phrase "tumor cell damaging approaches" refers to approaches, such as ionizing radiation. The term "ionizing radiation", referred to above and hereinafter, means ionizing radiation that occurs as either electromagnetic rays, such as X-rays and gamma rays; or particles, such as alpha, beta and gamma particles. Ionizing radiation is provided in, but not limited to, radiation therapy and is known in the art. See Hellman, Cancer, 4th Edition, Vol. 1, Devita et al., Eds., pp. 248-275 (1993).

The term "EDG binder" as used herein, includes, but is not limited to, a class of immunosuppressants that modulates lymphocyte recirculation, such as FTY720.

The term "ribonucleotide reductase inhibitor" as used herein, includes, but is not limited to, pyrimidine or purine nucleoside analogs including, but not limited to, fludarabine and/or ara-C; 6-thioguanine; 5-FU; cladribine; 6-mercaptopurine, especially in combination with ara-C against ALL; and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL 8. See Nandy et al., Acta Oncologica, Vol. 33, No. 8, pp. 953-961 (1994).

The term "S-adenosylmethionine decarboxylase inhibitors", as used herein, includes, but is not limited to, the compounds disclosed in U.S. Pat. No. 5,461,076.

The phrase "monoclonal antibodies of VEGF or VEGFR", as used herein, includes but is not limited to, compounds disclosed in WO 98/35958, e.g., 1-(4-chloroanilino)-4-(4-pyridylmethyl)phthalazine or a pharmaceutically acceptable salt thereof, e.g., the succinate, or in WO 00/09495, WO 00/27820, WO 00/59509, WO 98/11223, WO 00/27819 and EP 0 769 947; those as described by Prewett et al., Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999) in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g., rhuMAb and RHUFab; VEGF aptamer, e.g., Macugon; FLT-4 inhibitors; FLT-3 inhibitors; VEGFR-2 IgG1 antibody; Angiozyme (RPI 4610); and Avastan.

The term "photodynamic therapy", as used herein, refers to therapy which uses certain chemicals known as photosensitizing agents to treat or prevent cancers. Examples of photodynamic therapy include, but are not limited to, treatment with agents, such as, e.g., VISUDYNE and porfimer sodium.

The term "angiostatic steroid", as used herein, includes, but is not limited to agents which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

The phrase "Implant containing corticosteroids" as used herein, includes, but is not limited to agents, such as, e.g., fluocinolone and dexamethasone.

The term "AT1 receptor antagonist" as used herein, includes, but is not limited to agents, such as DIOVAN.

The term "ACE inhibitor" as used herein, includes, but is not limited to CIBACEN, benazepril, enazepril (LOTENSIN), captopril, enalapril, fosinopril, lisinopril, moexipril, quinapril, ramipril, perindopril and trandolapril.

Other pharmaceutically active agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

In each case where citations of patent applications or scientific publications are given, in particular with regard to the respective compound claims and the final products of the working examples therein, the subject matter of the final products, the pharmaceutical preparations and the claims is hereby incorporated into the present application by reference to these publications. Comprised are likewise the corresponding stereoisomers, as well as the corresponding crystal modifications, e.g., solvates and polymorphs, which are disclosed therein. The compounds used as active ingredients in the combinations disclosed herein can be prepared and administered as described in the cited documents, respectively.

The structure of the active agents identified by code numbers, generic or trade names may be taken from the actual edition of the standard compendium "The Merck Index" or from databases, e.g., Patents International, e.g., IMS World Publications, or the publications mentioned above and below. The corresponding content thereof is hereby incorporated by reference.

It will be understood that references to the components (a) and (b) are meant to also include the pharmaceutically acceptable salts of any of the active substances. If active substances comprised by components (a) and/or (b) have, for example, at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization.

Thus, in a first aspect, the present invention relates to a method for the prevention of treatment of proliferative diseases or diseases that are triggered by persistent angiogenesis in a mammal, preferably a human patient, which comprises treating the patient concurrently or sequentially with pharmaceutically effective amounts of a combination of:

(a) a neutralizing anti-DKK1/4 composition; and (b) an pharmaceutically active agent.

In preferred embodiment, the present invention provides a pharmaceutical preparation comprising:

(a) a neutralizing anti-DKK1/4 composition; and (b) one or more pharmaceutically active agents selected from the group consisting of an aromatase inhibitor; an anti-estrogen; an anti-androgen; a gonadorelin agonist; a topoisomerase I inhibitor; a topoisomerase II inhibitor; a microtubule active agent; an alkylating agent; an anti-neoplastic anti-metabolite; a platin compound; a compound targeting/decreasing a protein or lipid kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier; an inhibitor of Ras oncogenic isoforms; a telomerase inhibitor; a protease inhibitor, a matrix metalloproteinase inhibitor, a methionine aminopeptidase inhibitor; a proteasome inhibitor; agents which target, decrease or inhibit the activity of Flt-3; an HSP90 inhibitor; antiproliferative antibodies; an HDAC inhibitor; a compound which targets, decreases or inhibits the activity/function of serine/theronine mTOR kinase; a somatostatin receptor antagonist; an anti-leukemic compound; tumor cell damaging approaches; an EDG binder; a ribonucleotide reductase inhibitor; an S-adenosylmethionine decarboxylase inhibitor; a monoclonal antibody of VEGF or VEGFR; photodynamic therapy; an Angiostatic steroid; an implant containing corticosteroids; an AT1 receptor antagonist; and an ACE inhibitor.

Any of the combination of components (a) and (b), the method of treating a warm-blooded animal comprising administering these two components, a pharmaceutical composition comprising these two components for simultaneous, separate or sequential use, the use of the combination for the delay of progression or the treatment of a proliferative disease or for the manufacture of a pharmaceutical preparation for these purposes or a commercial product comprising such a combination of components (a) and (b), all as mentioned or defined above, will be referred to subsequently also as combination of the invention (so that this term refers to each of these embodiments which thus can replace this term where appropriate).

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of measurable blood levels of both compounds are present in an overlapping manner (at the same time).

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). Whether this is the case, can inter alia be determined by following the blood levels, showing that both compounds are present in the blood of the human to be treated at least during certain time intervals.

"Pharmaceutically effective" preferably relates to an amount that is therapeutically or in a broader sense also prophylactically effective against the progression of a proliferative disease.

The term "a commercial package" or "a product", as used herein defines especially a "kit of parts" in the sense that the components (a) and (b) as defined above can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal anti-tumor effect) or the like.

The COMBINATION OF THE INVENTION can also be applied in combination with other treatments, e.g., surgical intervention, hyperthermia and/or irradiation therapy.

The pharmaceutical compositions according to the present invention can be prepared by conventional means and are those suitable for enteral, such as oral or rectal, and parenteral administration to mammals including man, comprising a therapeutically effective amount of a VEGF inhibitor and at least one pharmaceutically active agent alone or in combination with one or more pharmaceutically acceptable carriers, especially those suitable for enteral or parenteral application.

The pharmaceutical compositions comprise from about 0.00002 to about 100%, especially, e.g., in the case of infusion dilutions that are ready for use, of 0.0001 to 0.02%, or, e.g., in case of injection or infusion concentrates or especially parenteral formulations, from about 0.1% to about 95%, preferably from about 1% to about 90%, more preferably from about 20% to about 60% active ingredient (weight by weight, in each case). Pharmaceutical compositions according to the invention may be, e.g., in unit dose form, such as in the form of ampoules, vials, dragées, tablets, infusion bags or capsules.

The effective dosage of each of the combination partners employed in a formulation of the present invention may vary depending on the particular compound or pharmaceutical compositions employed, the mode of administration, the condition being treated and the severity of the condition being treated. A physician, clinician or veterinarian of ordinary skill can readily determine the effective amount of each of the active ingredients necessary to prevent, treat or inhibit the progress of the condition.

Tyrphostins, especially Adaphostin, are preferably administered to a warm-blooded animal, especially a human in a dosage in the range of about 1-6000 mg/day, more preferably 25-5000 mg/day, most preferably 50-4000 mg/day. Unless stated otherwise herein, the compound is preferably administered from one to 5, especially from 1-4 times per day.

Pharmaceutical preparations for the combination therapy for enteral or parenteral administration are, e.g., those in unit dosage forms, such as sugar-coated tablets, capsules or suppositories, and furthermore ampoules. If not indicated otherwise, these formulations are prepared by conventional means, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units. One of skill in the art has the ability to determine appropriate pharmaceutically effective amounts of the combination components.

Preferably, the compounds or the pharmaceutically acceptable salts thereof, are administered as an oral pharmaceutical formulation in the form of a tablet, capsule or syrup; or as parenteral injections if appropriate.

In preparing compositions for oral administration, any pharmaceutically acceptable media may be employed such as water, glycols, oils, alcohols, flavoring agents, preservatives, coloring agents. Pharmaceutically acceptable carriers include starches, sugars, microcrystalline celluloses, diluents, granulating agents, lubricants, binders, disintegrating agents.

Solutions of the active ingredient, and also suspensions, and especially isotonic aqueous solutions or suspensions, are useful for parenteral administration of the active ingredient, it being possible, e.g., in the case of lyophilized compositions that comprise the active ingredient alone or together with a pharmaceutically acceptable carrier, e.g., mannitol, for such solutions or suspensions to be produced prior to use. The pharmaceutical compositions may be sterilized and/or may comprise excipients, e.g., preservatives, stabilizers, wetting and/or emulsifying agents, solubilizers, salts for regulating the osmotic pressure and/or buffers, and are prepared in a manner known per se, e.g., by means of conventional dissolving or lyophilizing processes. The solutions or suspensions may comprise viscosity-increasing substances, such as sodium carboxymethylcellulose, carboxymethylcellulose, dextran, polyvinylpyrrolidone or gelatin. Suspensions in oil comprise as the oil component the vegetable, synthetic or semi-synthetic oils customary for injection purposes.

The isotonic agent may be selected from any of those known in the art, e.g. mannitol, dextrose, glucose and sodium chloride. The infusion formulation may be diluted with the aqueous medium. The amount of aqueous medium employed as a diluent is chosen according to the desired concentration of active ingredient in the infusion solution. Infusion solutions may contain other excipients commonly employed in formulations to be administered intravenously such as antioxidants.

The present invention further relates to "a combined preparation", which, as used herein, defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single patient based on the severity of any side effects that the patient experiences.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein in intended to include human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with DKK1 expression. When antibodies to DKK1 are administered together with another agent, the two can be administered in either order or simultaneously.

In one embodiment, the antibodies (and immunoconjugates and bispecific molecules) of the invention can be used to detect levels of DKK1, or levels of cells that contain DKK1. This can be achieved, for example, by contacting a sample (such as an in vitro sample) and a control sample with the anti-DKK1 antibody under conditions that allow for the formation of a complex between the antibody and DKK1. Any complexes formed between the antibody and DKK1 are detected and compared in the sample and the control. By non-limiting example, standard detection methods that are well known in the art, such as e.g., ELISA, MALDI and flow cytometic assays, can be performed using the compositions of the invention.

Accordingly, in one aspect, the invention further provides methods for detecting the presence of DKK1 (e.g., human DKK1 antigen) in a sample, or measuring the amount of DKK1, comprising contacting the sample, and a control sample, with an antibody of the invention, or an antigen binding portion thereof, which specifically binds to DKK1, under conditions that allow for formation of a complex between the antibody or portion thereof and DKK1. The formation of a complex is then detected, wherein a difference in complex formation between the sample compared to the control sample is indicative of the presence of DKK1 in the sample.

Also within the scope of the invention are kits consisting of the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Example 1

Generation of Human DKK1-Specific Antibodies from the HuCAL GOLD® Library

Therapeutic antibodies against human DKK1 protein are generated by selection of clones having high binding affinities, using as the source of antibody variant proteins a commercially available phage display library, the MorphoSys HuCAL GOLD® library. HuCAL GOLD® is a Fab library (Knappik et al., 2000 J. Mol. Biol. 296:57-86; Krebs et al., 2001 J Immunol. Methods 254:67-84; Rauchenberger et al., 2003 J Biol Chem. 278(40):38194-38205), in which all six CDRs are diversified by appropriate mutation, and which employs the CysDisplay™ technology for linking Fab fragments to the phage surface (WO 01/05950 Löhning 2001).

General Procedures: Phagemid Rescue, Phage Amplification, and Purification

The HuCAL GOLD® library is amplified in standard rich bacterial medium (2×YT) containing 34 μg/ml chloramphenicol and 1% glucose (2×YT-CG). After infection of cells at an $OD_{600nm}$ of 0.5 with VCSM13 helper phages (incubating the mix of cells and phage for 30 min at 37° C. without shaking followed by 30 min at 37° C. shaking at 250 rpm), cells are centrifuged (4120 g; 5 min; 4° C.), are resuspended in 2×YT/34 μg/ml chloramphenicol/50 μg/ml kanamycin/0.25 mM IPTG, and are grown overnight at 22° C. At the end of this period cells are removed by centrifugation, and phages are PEG-precipitated twice from the supernatant, resuspended in PBS/20% glycerol and are stored at –a 80° C.

Phage amplification between two panning rounds is conducted as follows: mid-log phase *E. coli* strain TG1 cells are infected with phages are eluted following the selection with DKK1 protein, and are plated onto LB-agar supplemented with 1% of glucose and 34 μg/ml of chloramphenicol (LB-CG plates). After overnight incubation of the plates at 30° C., bacterial colonies are scraped off the agar surface, and used to inoculate 2×YT-CG broth to obtain an $OD_{600nm}$ of 0.5, then VCSM13 helper phages are added to obtain a productive infection as described above.

Pre-Experiments for Solution Panning Using Strep-Tactin Magnetic Beads

The Strep-tag II has been reported to have low affinity for the Strep-Tactin matrix ($K_D$~1 μM according to (Voss and Skerra, 1997 Protein Eng. 10:975-982), therefore, a pre-experiment is performed to assess the suitability of using Strep-Tactin-coated MagStrep beads for the capturing of the antigen during the antibody selections, and to avoid antigen loss during the pannings.

For that purpose, 8 mg of MagStrep beads is incubated with 46 μg of His-Strep-tagged DKK1 for 1 h at room temperature and the sample is divided into four pre-blocked Eppendorf tubes. One tube served as the positive control (no washing) and the other three samples are washed with different stringencies according to the HuCAL GOLD® manual panning section. Detection of binding of the His-Strep-tagged DKK1 to the MagStrep beads (Strep-Tactin coated Magnetic beads obtained from IBA, Göttingen, Germany) is performed in BioVeris using a goat anti-DKK1 antibody and a Rubidium-labeled anti-goat detection antibody.

As shown in FIG. 1 herein, no significant loss of His-Strep-tagged DKK1 from the Strep-Tactin-coated beads is detectable when the non-washed beads are compared with those beads washed with different HuCAL® stringencies. Thus, the His-Strep-tagged DKK1 seemed to be suitable for the use in the solution pannings with Strep-Tactin-coated magnetic beads (MagStrep beads).

Selection by Panning of DKK1-Specific Antibodies from the Library

For the selection of antibodies recognizing human DKK1, two panning strategies are applied.

In summary, HuCAL GOLD® phage-antibodies are divided into four pools comprising different combinations of $V_H$ master genes (pool 1 contained VH1/5λκ; pool 2 contained $V_H$3λκ; pool 3 contained $V_H$2/4/6λκ; and pool 4 contained $V_H$1-6λκ). These pools are individually subjected to two rounds of solution panning His-Strep-tagged DKK1 captured onto StrepTactin magnetic beads (Mega Strep beads; IBA), and for the third selection round only, either on His-Strep-tagged DKK1 captured onto StrepTactin magnetic beads or on APP-tagged human DKK1 protein captured by Streptavidin beads (Dynabeads® M-280 Streptavidin; Dynal) with a biotinylated anti-APP antibody.

In detail, for the solution panning using His-Strep-tagged DKK1 coupled to StrepTactin magnetic beads, the following protocol is applied: pre-blocked tubes are prepared (1.5 ml Eppendorf tubes) by treatment with 1.5 ml 2× ChemiBLOCKER diluted 1:1 with PBS over night at 4° C. Pre-blocked beads are prepared by treatment as follows: 580 μl (28 mg beads) StrepTactin magnetic beads are washed once with 580 μl PBS and resuspended in 580 μl 1× ChemiBLOCKER (diluted in one volume 1×PBS). Blocking of the beads is performed in the pre-blocked tubes over night at 4° C.

Phage particles diluted in PBS to a final volume of 500 μl for each panning condition are mixed with 500 μl 2× ChemiBLOCKER/0.1% Tween and kept for one hour at room temperature on a rotating wheel. Pre-adsorption of phage particles for removal of StrepTactin or beads-binding phages is performed twice: 160 μl of blocked StrepTactin magnetic beads (4 mg) is added to the blocked phage particles, and is incubated for 30 min at room temperature on a rotating wheel. After separation of the beads by a magnetic device (Dynal MPC-E), the phage supernatant (~1.1 ml) is transferred to a fresh, blocked reaction tube and pre-adsorption is repeated using 160 μl blocked beads for 30 min. Then, His-Strep-tagged DKK1, either 400 nM or 100 nM, is added to the blocked phage particles in a fresh, blocked 1.5 ml reaction tube and the mixture is incubated for 60 min at room temperature on a rotating wheel.

The phage-antigen complexes are captured using either 320 μl or 160 μl of blocked StrepTactin magnetic beads added to the 400 nM or the 100 nM phage panning pools, respectively, which is then incubated for 20 min at room temperature on a rotating wheel. Phage particles bound to the StrepTactin magnetic beads are again collected with the magnetic particle separator.

Beads are then washed seven times with PBS/0.05% Tween (PBST), followed by washing another three times with PBS only. Elution of phage particles from the StrepTactin magnetic beads is performed by addition of 200 μl 20 mM DTT in 10 mM Tris-HCl, pH 8.0 to each tube for 10 min. The eluate is collected, and the beads are washed once with 200 μl PBS and the PBS eluate is added to the DTT eluate. This eluate sample is used to infect 14 ml of an *E. coli* TG-1 culture that had been grown to an $OD_{600nm}$ of 0.6-0.8.

After infection and subsequent centrifugation for 10 min at 5000 rpm, each bacterial pellet is resuspended in 500 μl 2×YT medium, plated onto 2×YT-CG agar plates and incubated overnight at 30° C. The next morning, the resulting colonies are scraped off the plates and the phage is prepared by rescue and amplification as described above.

The second round of solution pannings on His-Strep-tagged DKK1 is performed according to the protocol of the first round, except that decreasing amounts of antigen are used (50 nM, and 10 nM) and the stringency of the washing procedure is altered appropriately.

Two different panning strategies are applied for the third selection round: the amplified phage output of the second panning round is split and subjected to two different panning conditions. The first half of the phage output is used for the standard panning strategy on human His-Strep-tagged DKK1 captured onto StrepTactin beads as described above (antigen amounts are 10 nM or 1 nM, respectively).

The second panning variation for the third selection round is performed on human APP-tagged DKK1. APP-tagged DKK1 protein at a final concentration of 50 nM or 10 nM is mixed with 1 ml of pre-cleared, second round phage particles, and the mixture is incubated at room temperature for 1 hour on a rotating wheel. In parallel, 8 mg pre-blocked Dynabeads M-280 Streptavidin (Dynal) is incubated with 40 μg biotinylated mouse anti-APP antibody for 30 min at room temperature on a rotating wheel followed by two washing steps with PB ST. The pre-formed complexes consisting of phage-antibodies bound to APP-tagged DKK1 are captured by the anti-APP coated M-280 Streptavidin magnetic beads for 30 min at room temperature. Phage elution and amplification are performed as described above.

Subcloning and Expression of Soluble Fab Fragments

The Fab-encoding inserts of the selected HuCAL GOLD® phagemids are subcloned into expression vector pMORPH®X9_Fab_FH, in order to facilitate rapid and efficient expression of soluble Fabs. For this purpose, the plasmid DNA of the selected clones is digested with restriction enzyme endonucleases XbaI and EcoRI, thereby excising the Fab-encoding insert (ompA-VLCL and phoA-Fd). This insert is then cloned into XbaI/EcoRI-digested expression vector pMORPH®X9_Fab_FH.

Fab proteins are expressed from this vector, and as a result carry two C-terminal tags (FLAG™ and 6×His, respectively) for both detection and purification.

Microexpression of HuCAL GOLD® Fab Antibodies in *E. coli*

To obtain sufficient amounts of protein encoded by each of the clones obtained above, chloramphenicol-resistant single bacterial colonies are selected after subcloning of the selected Fabs into the pMORPH®X9_Fab_FH expression vector. Each of these colonies is then used to inoculate the wells of a sterile 96-well microtiter plate, each well containing 100 μl 2×YT-CG medium per well, and bacteria are grown overnight at 37° C. A sample (5 μl) of each *E. coli* TG-1 culture is transferred to a fresh, sterile 96-well microtiter plate pre-filled with 100 μl 2×YT medium supplemented with 34 μg/ml chloramphenicol and 0.1% glucose per well. The microtiter plates are incubated at 30° C. with shaking at 400 rpm on a microplate shaker until the cultures are slightly turbid (~2-4 hrs) with an $OD_{600nm}$ of about 0.5.

For expression in the format of these plates, 20 μl 2×YT medium supplemented with 34 μg/ml chloramphenicol and 3 mM IPTG (isopropyl-β-D-thiogalactopyranoside) is added per well (final concentration 0.5 mM IPTG), the microtiter plates sealed with a gas-permeable tape, and incubated overnight at 30° C. shaking at 400 rpm.

Generation of Whole Cell Lysates (BEL Extracts)

To each well of the expression plates, 40 μl BEL buffer (2×BBS/EDTA: 24.7 g/l boric acid, 18.7 g NaCl/1, 1.49 g EDTA/1, pH 8.0) containing 2.5 mg/ml lysozyme is added, and plates are incubated for 1 h at 22° C. on a microtiter plate shaker (400 rpm). The BEL extracts are used for binding analysis by FMAT (see Example 2).

Expression of Microgram Amounts of HuCAL GOLD® Fab Antibodies in *E. coli* and Purification Expression of Fab fragments encoded by pMORPH®X9_Fab_FH in *E. coli* TG1 F-cells is carried out in 50 ml plastic tubes. For this purpose, pre-cultures inoculated with single clones are grown in 2×YT-CG medium overnight at 30° C. The next morning, 50 μl of each pre-culture are used to inoculate 25 ml 2×YT medium supplemented with 34 μg/ml Chloramphenicol, 1 mM IPTG, and 0.1% glucose in sterile 50 ml plastic tubes, and incubated over night at 30° C. *E. coli* cells are harvested, the cell pellets frozen and finally disrupted with Bug Buster (Novagen). The Fab fragments are isolated using Ni-NTA Agarose (Qiagen, Hilden, Germany).

Expression of Milligram Amounts of HuCAL GOLD Fab Antibodies in *E. coli* and Purification Expression of Fab fragments encoded by pMORPH®X9_Fab_FH in TG1 F-cells is carried out in shaker flask cultures using 750 ml of 2×YT medium supplemented with 34 μg/ml chloramphenicol. Cultures are shaken at 30° C. until the $OD_{600nm}$ reached 0.5. Expression is induced by addition of 0.75 mM IPTG followed by incubation for 20 h at 30° C. Cells are disrupted using lysozyme, and Fab fragments are isolated by Ni-NTA chromatography (Qiagen, Hilden, Germany). Protein concentrations are determined by UV-spectrophotometry (Krebs et al., 2001).

Example 2

Identification of DKK1-Specific HuCAL® Antibodies

BEL extracts of individual *E. coli* clones selected by the above mentioned panning strategies are analyzed by Fluorometric Microvolume Assay Technology (FMAT™, 8200 Cellular Detection System analyzer, Applied Biosystems, Foster City, Calif.), to identify clones encoding DKK1-specific Fabs. The FMAT™ 8100 HTS System is a fluorescence macro-confocal, high-throughput screening instrument that automates detection of mix-and-read, non-radioactive assays with live cells or beads (Miraglia, J. Biomol. Screening (1999), 4(4) 193-204).

Fluorometric Microvolume Assay Technology-Based Binding Analysis (FMAT) for Detection of DKK1-Binding Fabs from Bacterial Lysates For the detection of DKK1-binding Fab antibodies from *E. coli* lysates (BEL extracts), binding is analyzed with the FMAT 8200 cellular detection system (Applied Biosystems). To couple His-Strep-tagged DKK1 onto M-450 Epoxy beads (Dynal), a sample of 300 μl M-450 Epoxy beads ($1.2\times10^8$ beads) is transferred into a reaction tube and captured with a magnetic particle separator. The supernatant is removed and the beads are washed four times in 1 ml of 100 mM sodium phosphate buffer, pH 7.4. For antigen coating, 60 μg His-Strep-tagged DKK1 is added to the bead suspension in 150 μl 100 mM sodium phosphate buffer, pH 7.4. The antigen-bead suspension is incubated for 16 h at room temperature on a rotating wheel. The coated beads are then washed three times with PBS and resuspended in a final volume of 250 μl PBS.

For each 384-well plate, a mixture of 20 ml PBS containing 3% BSA, 0.005% Tween-20, 4 IA DKK1-coated beads ($1.9\times10^6$ beads) and 4 μl Cy5™ detection antibody is prepared. A sample of 45 μl of this solution is dispensed per well into a 384-well FMAT black/clear bottom plate (Applied Biosystems). Fab-containing BEL extract (5 μl) is added to each well. The FMAT plates are incubated at room temperature overnight. The next morning the plates are analyzed in the 8200 Cellular Detection System (Applied Biosystems).

Positive clones are obtained, and the heavy and light chain sequences of clones yielding positive, specific signals in FMAT are analyzed. It is observed that, 57 unique (non-redundant) anti-DKK1 clones are identified that showed sufficient strong binding to human DKK1. These clones are expressed, purified and tested for affinity and in functional assays.

Determination of Nanomolar Affinities Using Surface Plasmon Resonance

Using these clones, kinetic SPR analysis is performed on a CM5 chip (Biacore, Sweden) which had been coated with a density of ~400 RU of either recombinant human DKK1, mouse DKK1 (R&D system), or cynomolgus DKK1 in 10 mM Na-acetate pH 4.5 using standard EDC-NHS amine coupling chemistry. A comparable amount of human serum albumin (HSA) is immobilized on the reference flow cell. PBS (136 mM NaCl, 2.7 mM KCl, 10 mM Na2HPO4, 1.76 mM KH2PO4 pH 7.4) is used as the running buffer. The Fab preparations are applied in concentration series of 16-500 nM at a flow rate of 20 μl/min. Association phase is set to 60 s and dissociation phase to 120 s. A summary of the affinities in nM to each of human, mouse, and cynomolgus DKK1 determined by that method are shown in Table 1 herein.

TABLE 1

Affinities of selected Fabs to each of human, mouse, and cynomolgus

| Antibody | KD [nM] human DKK1 | KD [nM] mouse DKK1* | KD [nM] cyno DKK1* |
|---|---|---|---|
| MOR04470 | 3.2 ± 2.0 | 3.6 | 1.7 |
| MOR04516 | 2.6 ± 0.7 | 2.4 | 1.9 |
| MOR04454 | 3.2 ± 0.4 | 6 | 2.7 |
| MOR04456 | 7.9 ± 0.9 | 11.6 | 8.1 |
| MOR04461 | 7.6 ± 3.3 | 12.8 | 7.3 |
| MOR04455 | 1.6 ± 0.3 | n.d. | 1.5 |

*single measurement
n.d.: not determined

Example 3

Identification of Anti-Human DKK1 Fab Candidates Inhibiting the Wnt Antagonistic Activity of DKK1

Figure 2:
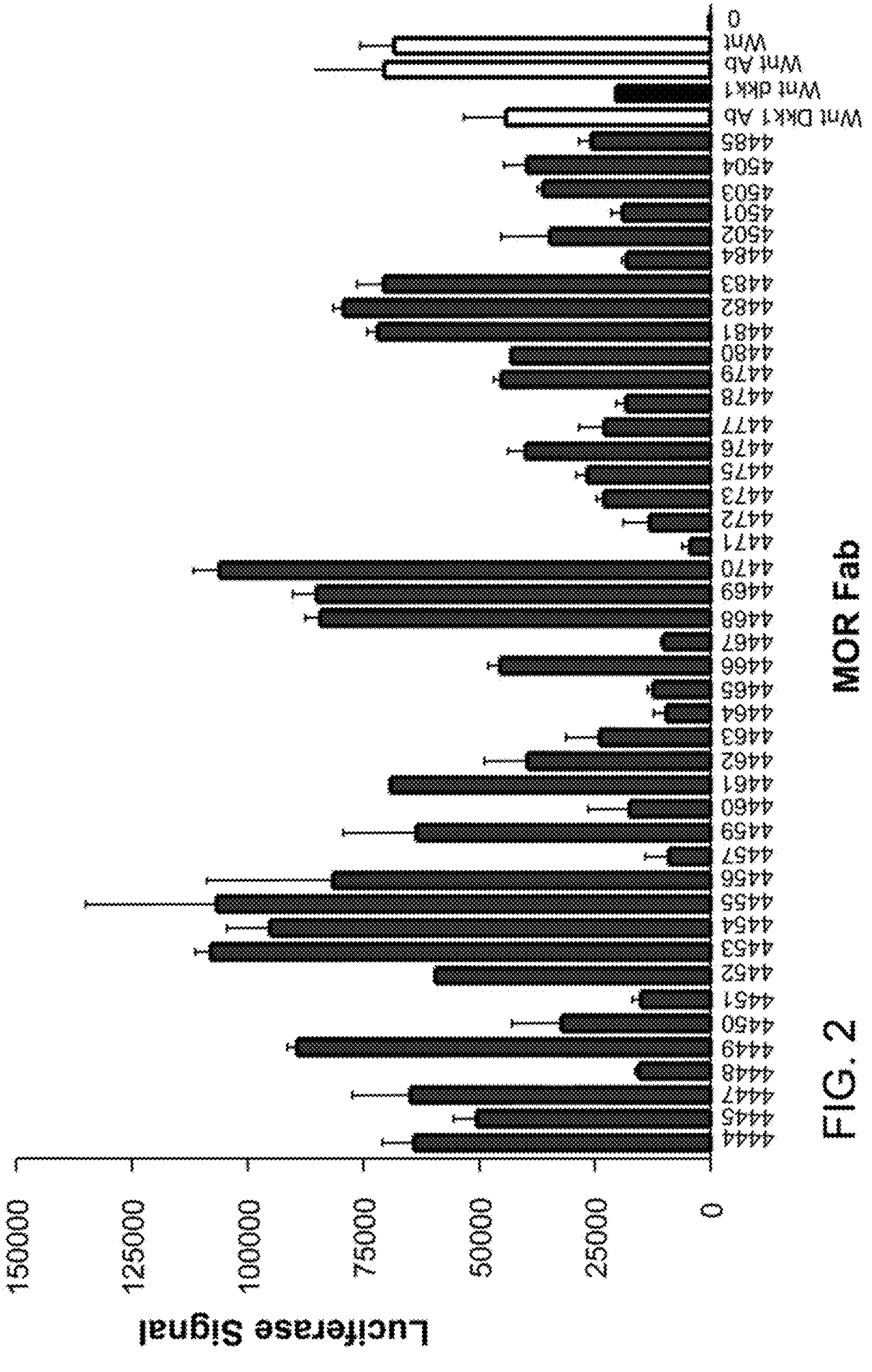
FIG. 2 is a bar graph illustrating the results of a Wnt activity Assay with 100 μl Bright-Glo luciferase reagent, as provided in Example 3.
Figure 4:
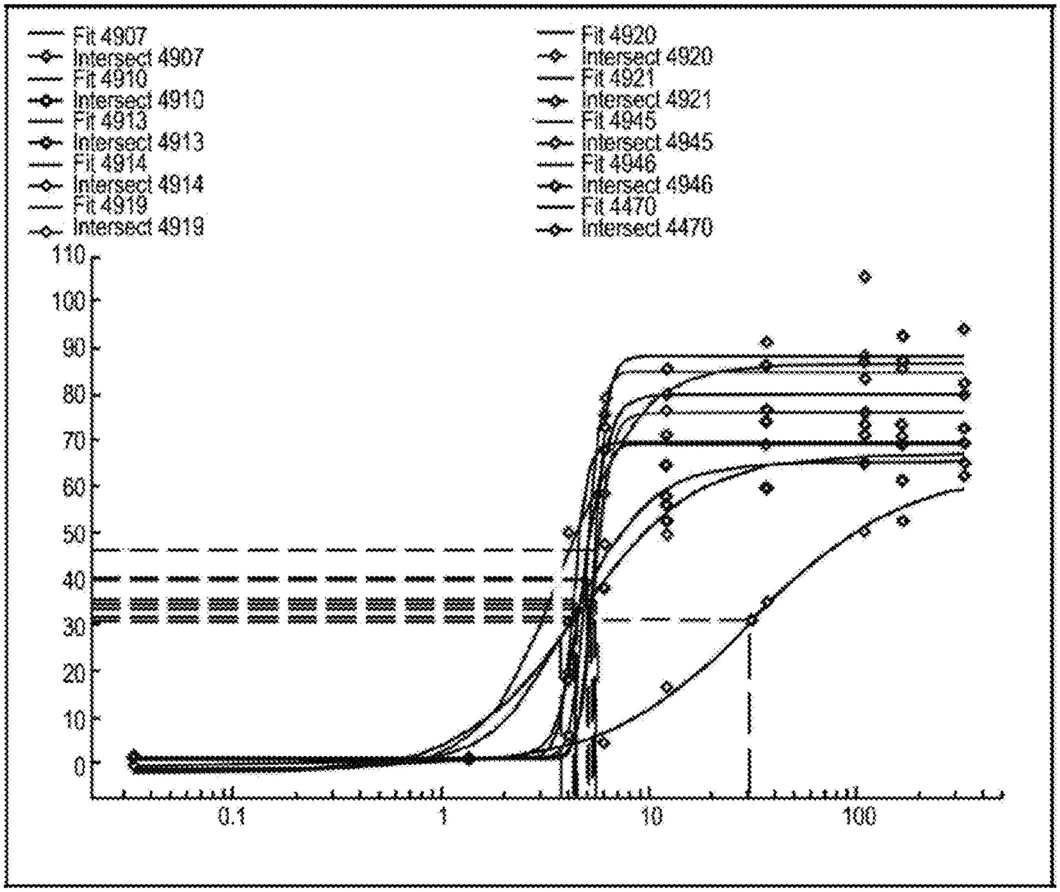
FIG. 4 is a graph illustrating the standard Wnt3a-dependent TCF/LEF luc reporter assay, as provided in Example 6.

The resulting 57 different DKK1-specific antibodies selected from the HuCAL GOLD® library are used to obtain purified antibody, which is then tested for potency to inhibit the Wnt antagonistic activity of human DKK1. Of these, 17 antibody candidates are functionally active, as shown in FIGS. 2 and 4.

The functional activity of each of the HuCAL® Fabs is checked using a luciferase reporter gene assay. Twelve TCF/Lef binding sites are cloned upstream of the luciferase reporter gene rendering the luciferase gene TCF/Lef-responsive. The canonical Wnt proteins lead to a stabilization of beta-catenin, thereby activating transcription of TCF/Lef and producing the luciferase protein. Addition of DKK1 protein blocks Wnt activity and therefore also the transcription of the luciferase gene. In consequence, the luciferase levels produced by the respective cells are expected to correlate with the potency of the selected Fabs to block DKK1 action.

Stable TCF/Lef-Responsive Reporter Cell Line HEK293T/17-12xSTF

Bioassays are performed using the stable human embryonic kidney cell reporter cell line HEK293T/17-12xSTF. The cells are cultivated in DMEM high glucose medium (Invitrogen), containing 10% FCS (PAN or BioWhittaker) and 1 μg/ml puromycin (BD Biosciences), until 90% confluency is reached. The cells are then trypsinized, counted, and diluted in culture medium without puromycin to a concentration of $4\times10^5$ cells per ml. Subsequently, the cells are seeded into a white, flat-bottom 96-well plate (Corning; 100 μl cell suspension per well) and incubated at 37° C. and 5% $CO_2$ over night. On the next day, the assay medium is prepared: 500 ng/ml DKK1-APP is added to Wnt3a Conditioned Medium (CM). The anti-DKK1 HuCAL® Fabs (final concentration 20 μg/ml) and the goat anti-human DKK1 antibody (R&D Systems) used as a positive control (final concentration 1.5 μg/ml) are diluted in CM.

A volume of 60 μl medium is removed from each well of the assay plate without disturbing the adhering cells, and substituted by 60 μl of the test antibody or control, diluted in CM. The cells are incubated for another 24 h and 100 μl Bright-Glo luciferase reagent is added to each well. After 5 min incubation time, the luminescence is read in a luminometer (GenioPro, Tecan). The results obtained with 20 of the 57 Fabs are shown in FIG. 2 herein. The extent of luciferase expressed is a measure of the extent of antibody present.

Example 4

Quantitative Analysis of Binding Affinities: Determination of Anti-Human DKK1 Fab Candidates that Inhibit the Wnt-Antagonistic Activity of DKK1

Affinity Determination

In order to further characterize the anti-DKK1 antibodies, the affinity to human, cynomolgus, and mouse DKK1 is determined. The recombinant DKK1 protein is immobilized on a CM5 Biacore chip and the Fabs are applied in the mobile phase in different concentrations. For a reliable determination of monovalent affinities only such Fab batches are used for Biacore measurements which showed ≥90% monomeric fraction in a size exclusion chromatography.

The summarized affinity data on human, mouse, and cynomolgus DKK1 is shown in Table 2. All 17 tested Fabs are found to have affinity to human DKK1 below 100 nM. Further, nine of the clones produced antibodies with affinities less than 10 nM. In all tested cases, the affinities for cynomolgus and mouse DKK1 are almost identical to those for human DKK1.

TABLE 2

Affinity data of selected Fabs on human, mouse, and cynomolgus

| Antibody | KD [nM] human DKK1 | KD [nM] mouse DKK1* | KD [nM] cyno DKK1* |
|---|---|---|---|
| MOR04480 | 1.0 ± 0.0 | 2 | n.d. |
| MOR04455 | 1.6 ± 0.3 | n.d. | 1.5 |
| MOR04516 | 2.6 ± 0.7 | 2.4 | 1.9 |
| MOR04470 | 3.2 ± 2.0 | 3.6 | 1.7 |
| MOR04454 | 3.2 ± 0.4 | 6 | 2.7 |
| MOR04483 | 5.5 ± 0.7 | n.d. | n.d. |
| MOR04466 | 6.5 ± 2.1 | n.d. | n.d. |
| MOR04461 | 7.6 ± 3.3 | 12.8 | 7.3 |
| MOR04456 | 7.9 ± 0.9 | 11.6 | 8.1 |
| MOR04462 | 16.5 ± 2.1 | n.d. | n.d. |
| MOR04447 | 22* | n.d. | n.d. |
| MOR04469 | 36 ± 0.0 | n.d. | n.d. |
| MOR04482 | 36 ± 5.7 | n.d. | n.d. |
| MOR04468 | 41.5 ± 21.9 | n.d. | n.d. |
| MOR04476 | 44* | n.d. | n.d. |
| MOR04481 | 65* | n.d. | n.d. |
| MOR04503 | 93* | n.d. | n.d. |

*single measurement
n.d.: not determined $EC_{50}$ Determination

The data showing the effective concentration for 50% inhibition for the clones of antibodies having the greatest affinity for DKK1 is shown in Table 3 herein. The data show that effective concentrations $EC_{50}$ range from 39-95 nM, with a median value between 58 and 83 nM.

TABLE 3

Effective concentration for 50% inhibition of selected Fabs

| Antibody | Luciferase reporter assay; $EC_{50}$ [nM] |
|---|---|
| MOR04470 | 58 |
| MOR04516 | 42 |
| MOR04454 | 83 |
| MOR04456 | 95 |
| MOR04461 | 57 |
| MOR04455 | 39 |

Example 5

Affinity Maturation of Selected Anti-DKK1 Fabs by Parallel Exchange of LCDR3 and HCDR2 Cassettes For optimizing the affinities of the antibodies described herein for DKK1 for a pool of parental Fab fragments, the LCDR3, framework 4 and the constant region of the light chains (405 bp) of each parental Fab is removed using BpiI and SphI, and is replaced by a repertoire of diversified LCDR3s together with framework 4 and the constant domain. A sample of 0.5 μg of the binder pool vector is ligated with a 3-fold molar excess of the insert fragment carrying the diversified LCDR3s.

In a similar approach, the HCDR2 is diversified using the XhoI and BssHII sites, and the connecting framework regions are kept constant. In order to increase the cloning efficiency, the parental HCDR2 is replaced by a 590 bp stiffer sequence prior to the insertion of the diversified HCDR2 cassette.

Ligation mixtures of 11 different libraries are electroporated into 4 ml *E. coli* TOP10 F' cells (Invitrogen, Carlsbad, Calif., USA), yielding from $2\times10^7$ to $2\times10^8$ independent colonies. Amplification of the libraries is performed as previously described (Rauchenberger et al., 2003 J Biol Chem. 278(40):38194-38205). For quality control, several clones per library are randomly picked and sequenced (SequiServe, Vaterstetten, Germany) using primers CFR84 (VL) and OCAL_Seq_Hp (VH).

Selection of Candidates for Affinity Maturation

Six selected maturation candidates ("parental Fabs") are selected by having been characterized as having the following properties: affinities to human DKK1 less than 10 nM, with significant cross-reactivity to cynomolgus and mouse DKK1, $EC_{50}$ less than 100 nM, and good to moderate Fab expression levels in *E. coli* and lack of aggregation after Fab purification.

During the course of the affinity measurements, it became evident that MOR04480 is highly unstable at high dilutions. For this reason, MOR04480 is omitted from the list of maturation candidates albeit having the highest affinity (1 nM) and the best $EC_{50}$ (7 nM) of all tested Fabs. MOR04483 had a high affinity of 5.5 nM to human DKK1 but is shown to be cross-reactive to mouse DKK1, and MOR04453 contained a high proportion of Fab aggregates after purification. Therefore, these two antibodies are also excluded from the maturation.

After careful evaluation of all available data, six maturation candidates (MOR04454, MOR04455, MOR04456, MOR04461, MOR04470, and MOR04516) are selected. The properties of these candidates are listed in Table 4 herein.

TABLE 4

| Properties of selected Fabs | | | | | | | |
|---|---|---|---|---|---|---|---|
| Antibody | KD [nM] human DKK1 | KD [nM] mouse DKK1* | KD [nM] cyno DKK1* | EC50 [nM] | Cross-reactivity mouse | Fab expression [mg/l] | Size exclusion chromatography |
| MOR04470 | 3.2 ± 2.0 | 3.6 | 1.7 | 58 | ++ | 32.8 | # |
| MOR04516 | 2.6 ± 0.7 | 2.4 | 1.9 | 42 | ++ | 1.5 | # |
| MOR04454 | 3.2 ± 0.4 | 6 | 2.7 | 83 | ++ | 17.8 | # |
| MOR04456 | 7.9 ± 0.9 | 11.6 | 8.1 | 95 | ++ | 10.7 | # |
| MOR04461 | 7.6 ± 3.3 | 12.8 | 7.3 | 57 | ++ | 12 | # |
| MOR04455 | 1.6 ± 0.3 | n.d. | 1.5 | 39 | ++ | 9 | # |

*single measurement
n.d.: not determined
monomeric portion > 90%

Generation of Selected Fab Libraries for Affinity Maturation

In order to obtain clones having increased affinity and inhibitory activity of the anti-DKK1 antibodies, the selected Fab clones MOR04454, MOR04455, MOR04456, MOR04461, MOR04470, and MOR4516 shown in the previous example are subjected to further rounds of diversification and selection, a process known as affinity maturation.

For this purpose, CDR regions are diversified using corresponding LCDR3 and HCDR2 maturation cassettes pre-built by trinucleotide mutagenesis (Virnekäs et al., 1994 Nucleic Acids Res. 22:5600-5607; Nagy et al., 2002 Nature Medicine 8:801-807). Table 5 herein shows the LCDR3 sequences for the parental clones MOR04454, MOR04455, MOR04456, MOR061, MOR04470 and MOR4516.

TABLE 5

| LCDR3 sequences for selected Fabs | | | |
|---|---|---|---|
| Antibody | VL | LCDR3 Sequence | SEQ ID NO: |
| MOR04454 | K1 | LQYYGMPP | 21 |
| MOR04455 | K1 | QQYDSIPM | 22 |
| MOR04456 | K3 | QQYGDEPI | 23 |
| MOR04470 | L2 | QSYASGNTKV | 25 |
| MOR04461 | L2 | STWDMTVDF | 24 |
| MOR04516 | L1 | ASFDMGSPNV | 26 |

Table 6 herein shows the HCDR2 sequences for the parental clones MOR04454, MOR04455, MOR04456, MOR061, MOR04470 and MOR4516.

TABLE 6

| HCDR2 sequences for selected Fabs | | | |
|---|---|---|---|
| Antibody | VH | HCDR2 Sequence | SEQ ID NO: |
| MOR04454 | H3 | DGSHMDKPPGYVFAF | 2 |
| MOR04455 | H3 | HYMDH | 3 |
| MOR04456 | H3 | TIYMDY | 4 |
| MOR04461 | H3 | MGIDLDY | 5 |
| MOR04470 | H3 | HGIDFDH | 6 |
| MOR04516 | H5 | GIPFRMRGFDY | 7 |

Fab fragments from expression vector pMORPH®X9_Fab_FH are subcloned into the phagemid vector pMORPH®25 (see U.S. Pat. No. 6,753,136). This vector provides the phage protein pIII fused N-terminally to a cysteine residue as well as a C-terminal cysteine to the Fd antibody chain and thus allows disulfide-linked display of the respective Fab fragments on the phage surface. Two different strategies are applied in parallel to optimize both the affinity and the efficacy of the parental Fabs.

Five phage antibody Fab libraries are generated in which the LCDR3 of five of the six parental clones is replaced by a repertoire of individual light chain CDR3 sequences. The LCDR3 maturation of MOR04454 is not performed, as this clone has an additional BpiI restriction site in one of the CDR regions and the BpiI restriction enzyme is used for the library cloning procedure.)

In parallel, the HCDR2 region of each parental clone is replaced by a repertoire of individual heavy chain CDR2 sequences. Each parental Fab is excised and replaced for a 590 bp stuffer. This DNA stuffer facilitates the separation of single digested from double digested vector bands and reduces the background of the high-affinity parental Fabs during the maturation pannings. In a subsequent step, the stiffer is excised from the Fab-encoding plasmids of each parental clone and replaced for the highly diversified HCDR2 maturation cassette.

Large affinity maturation libraries of more than $2\times10^7$ members are generated by standard cloning procedures, and the diversified clones are transformed into electro-competent *E. coli* TOP10F' cells (Invitrogen). Fab-presenting phages are prepared as described in Example 1 above.

Four maturation pools are built in order to facilitate the subsequent selection process: pool 1a consisted of the MOR04470, and MOR04516 LCDR3 libraries; pool 1b consisted of the MOR04470, and MOR04516 HCDR2 libraries; pool 2a consisted of the MOR04454, MOR04455, MOR04456, and MOR04461 LCDR3 libraries; and pool 2b consisted of the MOR04454, MOR04455, MOR04456, and MOR04461 HCDR2 libraries.

For each pool the panning is performed in solution using decreasing amounts of His-Strep-tagged DKK1 and phage-antigen capturing by Strep-Tactin beads. In parallel, each pool is applied in pannings using decreasing amounts of biotinylated DKK1, which is captured onto Neutravidin-coated plates. In order to increase the panning stringency and to select for improved off rates, competition with purified parental Fabs as well as unlabeled antigen is performed during prolonged incubation periods.

Immediately after the pannings the enriched phagemid pools are subcloned into the pMORPH®X9_FH expression vector. About 2300 single clones are picked, and the Fabs are induced with IPTG.

Maturation Panning Strategies

Panning procedures using the four antibody pools are performed with His-Strep-tagged DKK1 and with biotinylated His-Strep-tagged DKK1 in solution for two or three rounds, respectively. For each of the panning strategies, competition with the purified parental Fab proteins or with unlabeled APP-tagged DKK1, as well as low antigen concentrations and extensive washing, are used to increase stringency.

The solution panning on unlabeled His-Strep-tagged DKK1 is performed over two selection rounds mainly according to the standard protocol described in Example 1. Exceptions to these procedures are the application of reduced amounts of antigen (decreasing from 5 nM down to 1 nM), the high stringency of the washing procedure either with competitor or without, and prolonged incubation periods of antibody-phages together with the antigen.

For the first selection round using biotinylated DKK1, the wells of a Neutravidin plate are washed two times with 300 μl PBS. The wells are blocked with 2×ChemiBLOCKER (Chemicon, Temecula, Calif.) diluted 1:1 in PBS (Blocking Buffer). Prior to the selections, the HuCAL GOLD® phages are also blocked with one volume Blocking Buffer containing 0.1% Tween-20 for 30 min at room temperature. The blocked phage preparations are transferred in 100 μl aliquots to the wells of a Neutravidin-coated plate for 30 min at room temperature. This pre-adsorption step is repeated once. Blocked and pre-cleared phage preparations are incubated with 5 nM biotinylated DKK1 for 2 h at 22° C. on a rotating wheel. Parental Fab, APP-DKK1 or no competitor is added and the samples are incubated overnight at 4° C. on a rotating wheel.

Antigen-phage complexes are captured in the wells of a Neutravidin plate for 20 min at room temperature. After extensive washing steps, bound phage particles are eluted by addition of 200 μl of 20 mM DTT in 10 mM Tris pH 8.0 per well for 10 min at room temperature. The eluate is removed and added to 14 ml *E. coli* TG1 cells grown to an $OD_{600nm}$ of 0.6-0.8. The wells are rinsed once with 200 μl PBS and this solution is also added to the *E. coli* TG1 cells. Phage infection of *E. coli* is allowed for 45 min at 37° C. without shaking. After centrifugation for 10 min at 5000 rpm, the bacterial pellets are each resuspended in 500 μl 2×YT medium, plated onto 2×YT-CG agar plates and incubated overnight at 30° C. The colonies are harvested by scraping from the surface of the plates and the phage particles are rescued and amplified as described above.

The second and third round of the selection are performed as described above for the first round of selection, excepted that washing conditions are more stringent and antigen concentrations are 1 and 0.1 nM, respectively.

Electrochemiluminescence (BioVeris)-Based Binding Analysis of DKK1 Binding Fabs

For the detection of affinity-improved, DKK1-specific antibody fragments in *E. coli* lysates (BEL extracts), a BioVeris M-384 SERIES® Workstation (BioVeris Europe, Witney, Oxfordshire, UK), is used. The assay is carried out in 96-well polypropylene microtiter plates and PBS supplemented with 0.5% BSA and 0.02% Tween-20 as the assay buffer. Biotinylated human DKK1 is immobilized on M-280 Streptavidin paramagnetic beads (Dynal) according to the instructions of the supplier. A 1:25 dilution of the bead stock solution is added per well. Samples of 100 μl diluted BEL extract and beads are incubated overnight at room temperature on a shaker. For detection, anti-human (Fab)'2 (Dianova) labelled with BV-tag™ according to instructions of the supplier (BioVeris Europe, Witney, Oxfordshire, UK) is used.

A set of about 2300 randomly picked clones are analyzed by the method described above. A subset of 160 clones giving the highest values is chosen for further analysis in solution equilibrium titration.

Determination of Picomolar Affinities Using Solution Equilibrium Titration (SET)

For $K_D$ determination, monomer fractions (at least 90% monomer content, analyzed by analytical SEC; Superdex75, Amersham Pharmacia) of Fab are used. Electrochemiluminescence (ECL) based affinity determination in solution and data evaluation are basically performed as described by Haenel et al., 2005. A constant amount of Fab is equilibrated with different concentrations (serial $3^n$ dilutions) of human DKK1 (4 nM starting concentration) in solution. Biotinylated human DKK1 coupled to paramagnetic beads (M-280 Streptavidin, Dynal), and BV-tag™ (BioVeris Europe, Witney, Oxfordshire, UK) labelled anti-human $(Fab)'_2$ (Dianova) is added and the mixture incubated for 30 min. Subsequently, the concentration of unbound Fab is quantified by ECL detection using the M-SERIES® 384 analyzer (BioVeris Europe).

For this purpose, 160 single clones are selected and purified by Ni-NTA Agarose in the μg scale. Preliminary affinities are determined by 4-point solution equilibrium titration (SET) in BioVeris. From these data, 20 clones showing affinities are selected. These Fabs are purified in the mg scale. MOR04950 is excluded from affinity determination and further evaluation due to partial aggregation of the Fab which is detected in size exclusion chromatography. Final affinities are determined from two independent batches of each Fab clone using an 8-point SET measurement and human, mouse, and cynomolgus DKK1.

Affinity determination to mouse and cynomolgus DKK1 is done essentially as described above using mouse DKK1 (R&D Systems) and cynomolgus DKK1 as analyte in solution instead of human DKK1. For detection of free Fab, biotinylated human DKK1 coupled to paramagnetic beads is used. Affinities are calculated according to Haenel et al., 2005 Anal Biochem 339.1:182-184.

Using the assay conditions described above, the affinities for the affinity-optimized anti-DKK1 Fabs are determined in solution. Affinities are determined for MOR04910 and MOR04946, with $K_D$s below 30 pM to human DKK1 and between 36 and 42 pM to mouse and cynomolgus DKK1. Further seven antibodies showed affinities below 100 pM to all three antigens. Clone MOR04950 did not show binding to the biotinylated DKK1. The affinities are summarized in Table 7 herein.

TABLE 7

Affinities of Fabs

| Antibody | Affinity [pM]: solution equilibrium titration* Human DKK1 | Cyno DKK1 | Mouse DKK1 |
|---|---|---|---|
| MOR04913 | 38 ± 8 | 51 ± 10 | 44 ± 48 |
| MOR04946 | 25 ± 9 | 36 ± 9 | 41 ± 15 |
| MOR04907 | 114 ± 7 | 170 ± 35 | 167 ± 68 |
| MOR04945 | 69 ± 18 | 80 ± 31 | 74 ± 21 |
| MOR04914 | 94 ± 5 | 140 ± 3 | 200 ± 261 |
| MOR04920 | 53 ± 37 | 50 ± 20 | 40 ± 30 |
| MOR04954 | 110 ± 54 | 112 ± 25 | 36 ± 4 |
| MOR04952 | 100 ± 12 | 58 ± 17 | 71 ± 34 |
| MOR04948 | 57 ± 8 | 67 ± 17 | 65 ± 25 |
| MOR04910 | 24 ± 3 | 37 ± 11 | 42 ± 38 |
| MOR04921 | high batch-to batch variation | | |
| MOR04947 | 32 ± 19 | 58 ± 35 | 30 ± 17 |
| MOR04951 | 136 ± 120 | 62 ± 2 | 132 ± 90 |
| MOR04918 | 110-690 | 236 ± 23 | 550-3144 |

TABLE 7-continued

| Affinities of Fabs | | | |
|---|---|---|---|
| Antibody | Affinity [pM]: solution equilibrium titration* Human DKK1 | Cyno DKK1 | Mouse DKK1 |
| MOR04919 | 64 # | 132 # | 111 # |
| MOR04949 | 30 ± 23 | 55 ± 35 | 65 ± 36 |
| MOR04922 | 90 # | 70 # | 50 # |
| MOR04911 | 140 # | 190 # | 650 # |
| MOR04950 | no binding | | |

*at least two independent measurements performed from two different Fab baches
single measurement only

Example 6

Characterization of Affinity-Optimized Anti-Human DKK1 Fabs

Enzyme Linked Immuno Sorbent Assay (ELISA) Techniques

Binding specificity of the matured Fabs in the presence of 50% human serum (HS) is determined. Serial dilutions of human recombinant, biotinylated DKK1 in TBS are coated onto Neutravidin microtiter plates for 2 h at room temperature, from 8 ng DKK1 per well to a concentration of 125 ng DKK1 per well. After coating of the antigen, wells are blocked with TBS/0.05% Tween (TBS-T) supplemented with 1% BSA for 1 h at room temperature. Purified Fabs described above are diluted either in TBS/4% BSA or TBS/50% HS at a final concentration of 1 μg/ml, added to the coated and blocked wells and the plates are incubated for 1 h at room temperature. For detection, an anti-FLAG alkaline phosphatase (AP)-conjugated antibody (1:5000 dilution in TBST) and the fluorogenic substrate AttoPhos (Roche) are used. After each incubation, the wells of the microtiter plates are washed with TBST five times, except after the final incubation step with the labeled secondary antibody when wells are washed three times.

Figure 3:
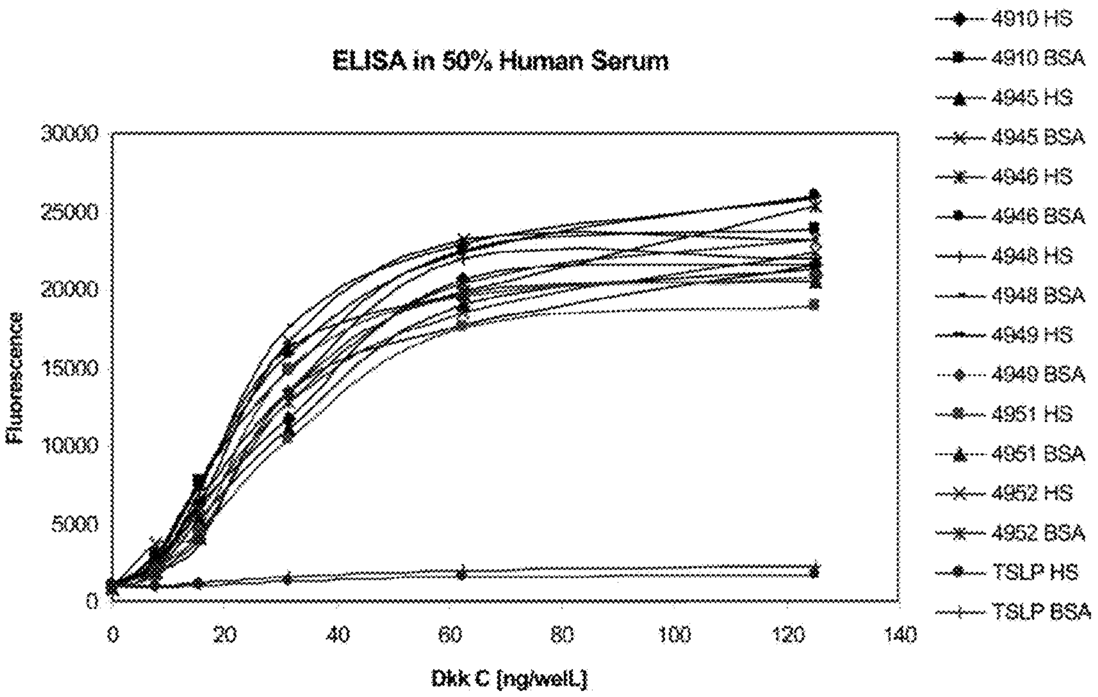
FIG. 3 is a graph of an Enzyme Linked Immuno Sorbent Assay (ELISA). The fluorescence is measured in a TECAN Spectrafluor plate reader and the binding curves are shown.

The fluorescence is measured in a TECAN Spectrafluor plate reader. Exemplary binding curves are shown in FIG. 3 herein. Table 8 summarizes the binding activity of the optimized anti-DKK1 Fabs in presence of 50% human serum compared to binding activity in 4% BSA, which ranges from 83% to 100%. The median value is found to be 93%, thus the anti-DKK1 Fabs are found to fully bind to target in the presence of human serum.

TABLE 8

| Binding activity of Fabs | |
|---|---|
| Antibody | Binding activity w/50% Human serum vs 4% BSA (%) |
| MOR04945 | 89 ± 6 |
| MOR04910 | 84 ± 4 |
| MOR04946 | 93 ± 2 |
| MOR04913 | 89 ± 9 |
| MOR04920 | 90 ± 7 |
| MOR04948 | 100 ± 15 |
| MOR04952 | 100 ± 5 |
| MOR04921 | 93* |
| MOR04914 | 83* |
| MOR04907 | >83* |
| MOR04954 | >83* |
| MOR04937 | 95* |

*single measurement

Luciferase Reporter Cell Assay in Presence of Human Serum Using the U2OS Cell Line For a further determination of binding specificity of the optimized anti-DKK1 Fabs, the luciferase reporter cell assay is repeated in presence of 15% human serum using the osteosarcoma cell line U2OS. The U2OS cells (ATCC No. HTB-96) are grown according to the provider's protocol (ATCC, Manassas, Va., USA). The cells are trypsinized, counted, and diluted in culture medium (McCoy's 5a/10% FCS) to a concentration of $2\times10^5$ cells/ml. For each $2\times10^4$ cells, a solution is prepared that is a mixture of 0.075 μg pTA-LUC-12xSuperTopFlash and 0.004 μg phRL-SV40. These are mixed in a final volume of 9.8 μl OPTI-MEM. Then 0.2 μl FuGENE 6 Transfection Reagent (Roche, Mannheim, Germany) is added. This transfection mix is briefly incubated and then mixed with the previously prepared cells. Subsequently, the cells are seeded in 100 μl per well of a white flat-bottomed 96-well cell culture dish and incubated at 37° C. and 5% $CO_2$ over night. The next day, 75 μl medium are removed from each well of the assay plate and substituted by 10 μl of HuCAL® Fab antibodies dilutions from (10 to 0.01 μg/ml diluted in serum-free culture medium), 15 μl of either 70% FCS or Human Serum, and 50 μl of the Wnt3a Conditioned Medium, containing 600 ng/ml DKK1-APP is added to each well.

For a negative control, serum-free medium is added instead of antibody dilutions. In order to obtain a maximum luciferase signal, controls containing 10 μl serum-free medium instead of antibody dilutions and 50 μl Wnt3a CM without DKK1-APP are added. After 24 h incubation at 37° C., 5% $CO_2$, the luminescence is measured with the Dual-Glo Luciferase Assay System (Promega, Madison, Wis., USA) according to the manufacturer's instructions.

Table 9 shows the inhibitory activity of the optimized anti-DKK1 Fabs in presence of 15% human serum (compared to the inhibitory activity in 15% FCS). The data shows that the activity obtained in the presence of serum ranged from 26% to 90%, with a median value of 70-74%. These data show that clones of the anti-DKK1 Fabs are obtained that function in the presence of human serum.

TABLE 9

| Inhibitory activity of Fabs | |
|---|---|
| Antibody | Luciferase reporter assay w/o Kremen; Activity in 15% Human serum (%) |
| MOR04945 | 74% |
| MOR04910 | 90% |
| MOR04946 | 60% |
| MOR04913 | 88% |
| MOR04920 | 75% |
| MOR04948 | 70% |
| MOR04952 | 60% |
| MOR04921 | 26% |
| MOR04914 | 80% |
| MOR04907 | 54% |
| MOR04954 | 55% |
| MOR04937 | 84% |

$EC_{50}$ Determination of Affinity-Optimized Anti-DKK1 Fabs by Luciferase Reporter Cell Assay The test of the affinity-improved Fabs in the standard Wnt3a-dependent TCF/LEF luc reporter assay used 10 nM DKK1 in order to obtain inhibition of the luciferase expression. It is seen that $EC_{50}$ values could not be generated by this method as the sensitivity of the assay is too low. This is indicated by very steep inhibition curves and similar $EC_{50}$ values for all Fabs tested as seen in FIG. 4 herein.

Figure 5:
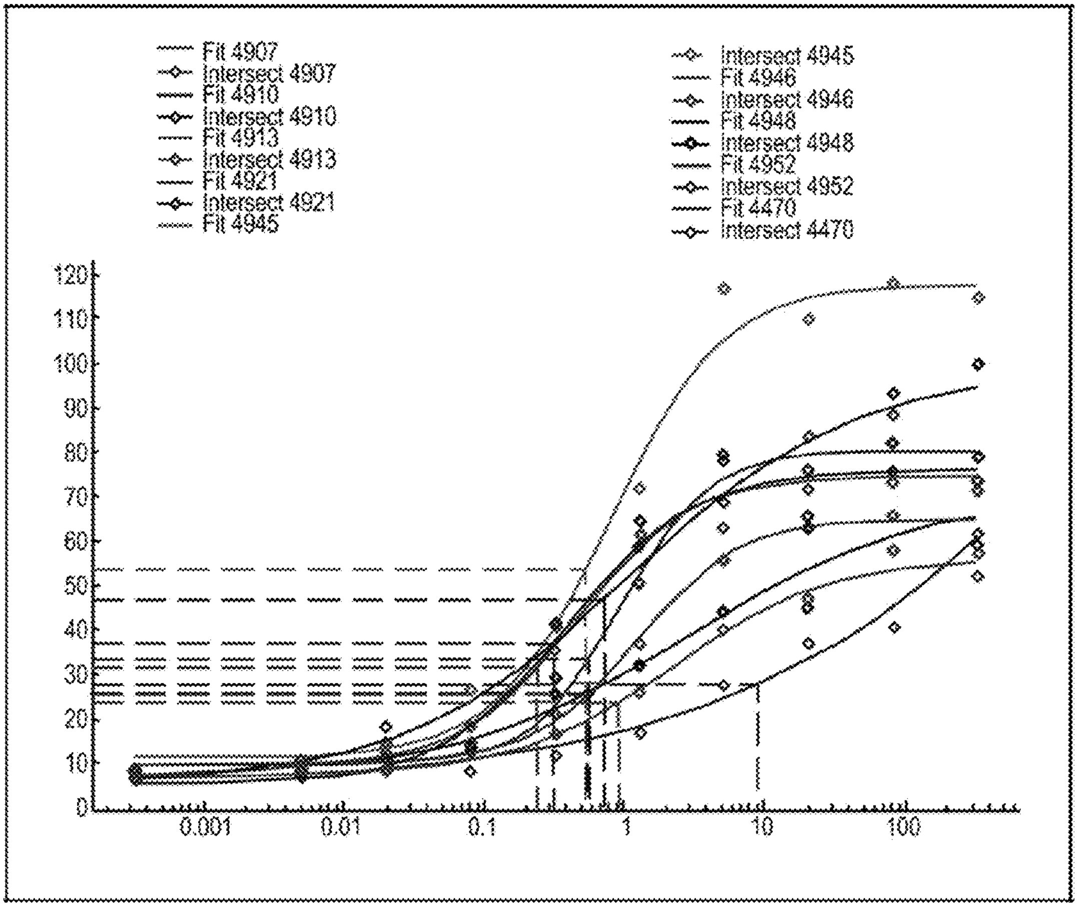
FIG. 5 is a graph illustrating an improved version of the TCF/LEF luc reporter assay showing highly improved sensitivity to DKK1 mediated by the co-expression of the Kremen co-receptor protein.

An improved version of the TCF/LEF luc reporter assay is developed. DKK1 binds to the Kremen-1 and -2 transmembrane proteins and this interaction leads to a strong synergistic inhibition of Wnt signaling (Mao et al. 2002 Nature: 417: 664-67). Therefore, Kremen cDNA is co-transfected with the TCF/LEF luc reporter assay. The resulting Wnt3a-dependent reporter assay showed highly improved sensitivity to DKK1, mediated by co-expression of the Kremen co-receptor protein. In this assay, 0.33 nM DKK1 is sufficient to induce full inhibition of Wnt signaling. The Fab titrations (at ten concentrations) are repeated using 0.33 nM DKK1, and yielded sigmoid inhibition curves (FIG. 5 herein) from which $EC_{50}$ values could be calculated.

The affinity-optimized anti-DKK1 Fabs are thereby analyzed with respect to $EC_{50}$ as described above. As shown in Table 10 herein, the $EC_{50}$ values obtained by this method ranged from 0.2 nM to 5.6 nM.

TABLE 10

| $EC_{50}$ of Fabs | |
|---|---|
| Antibody | TCF/LEF luc assay w/Kremen: EC50 [nM] |
| MOR04913 | 0.5 |
| MOR04946 | 0.2 |
| MOR04907 | 0.9 |
| MOR04945 | 0.5 |
| MOR04914 | 1.1 |
| MOR04920 | 1.8 |
| MOR04954 | 1.3 |
| MOR04952 | 0.6 |
| MOR04948 | 0.5 |
| MOR04910 | 0.3 |
| MOR04921 | 0.7 |
| MOR04947 | 1.7 |
| MOR04951 | 2.2 |
| MOR04919 | 2.7 |
| MOR04949 | 5.3 |
| MOR04922 | 2 |
| MOR04911 | 5.6 |

Sequence Analysis of the Affinity-Optimized Fabs

The nucleotide sequences of the heavy and $V_L$ regions ($V_H$ and $V_L$) of all twenty Fabs are determined Amino acid sequences of the complementarity determining regions (CDRs) are listed in Table 11A and Table 11B herein

TABLE 11A

| Amino acid sequences of Heavy Chain CDR's | | | | | | | | |
|---|---|---|---|---|---|---|---|---|
| | Antibody | VH | HCDR1 | SEQ ID No. HCDR 1 | HCDR2 | SEQ ID No. HCDR 2 | HCDR3 | SEQ ID No. HCDR 3 |
| P | MOR04455 | VH3 | GFTFSSYGMS | 3 | WVSGISGSGSYTYYADSVKG | 3 | HYMDH | 3 |
| 1 | MOR04918 | VH3 | GFTFSSYGMS | 49 | WVSGISERGVYIFYADSVKG | 57 | HYMDH | 65 |
| P | MOR04456 | VH3 | GFTFNNYGMT | 4 | WVSGISGSGSYTYYADSVKG | 4 | TIYMDY | 4 |
| 2 | MOR04907 | VH3 | GFTFNNYGMT | 8 | WVSGISGSGSYTYYADSVKG | 8 | TIYMDY | 8 |
| 3 | MOR04946 | VH3 | GFTFNNYGMT | 10 | WVSGISGSGSYTYYADSVKG | 10 | TIYMDY | 10 |
| 4 | MOR04949 | VH3 | GFTFNNYGMT | 50 | WVSGISGSGSYTYYADSVKG | 58 | TIYMDY | 66 |
| 5 | MOR04913 | VH3 | GFTFNNYGMT | 9 | WVSGISGSGSYTYYADSVKG | 9 | TIYMDY | 9 |
| P | MOR04461 | VH3 | GFTFSSYWMS | 5 | WVSGISYSGSNTHYADSVKG | 5 | MGIDLDY | 5 |
| 6 | MOR04911 | VH3 | GFTFSSYWMS | 51 | WVSDIEHKRRAGGATSYAASVKG | 59 | MGIDLDY | 67 |
| 7 | MOR04922 | VH3 | GFTFSSYWMS | 52 | WVSMIEHKTRGGTTDYAAPVKG | 60 | MGIDLDY | 68 |
| 8 | MOR04910 | VH3 | GFTFSSYWMS | 11 | WVSGISYSGSNTHYADSVKG | 11 | MGIDLDY | 11 |
| 9 | MOR04948 | VH3 | GFTFSSYWMS | 13 | WVSGISYSGSNTHYADSVKG | 13 | MGIDLDY | 13 |
| 10 | MOR04919 | VH3 | GFTFSSYWMS | 53 | WVSGISYSGSNTHYADSVKG | 61 | MGIDLDY | 69 |
| 11 | MOR04921 | VH3 | GFTFSSYWMS | 12 | WVSGISYSGSNTHYADSVKG | 12 | MGIDLDY | 12 |
| P | MOR04470 | VH3 | GFTFSSYWMS | 6 | WVSVISSDSSSTYYADSVKG | 6 | HGIDFDH | 6 |
| 12 | MOR04914 | VH3 | GFTFSSYWMS | 14 | WVSVISSDSSSTYYADSVKG | 14 | HGIDFDH | 14 |
| 13 | MOR04945 | VH3 | GFTFSSYWMS | 16 | WVSVISSDSSSTYYADSVKG | 16 | HGIDFDH | 16 |
| 14 | MOR04951 | VH3 | GFTFSSYWMS | 54 | WVSVISSDSSSTYYADSVKG | 62 | HGIDFDH | 70 |
| 15 | MOR04952 | VH3 | GFTFSSYWMS | 55 | WVSVISSDSSSTYYADSVKG | 63 | HGIDFDH | 71 |

TABLE 11A-continued

| Amino acid sequences of Heavy Chain CDR's | | | | | | | | |
|---|---|---|---|---|---|---|---|---|
| | Antibody | VH | HCDR1 | SEQ ID No. HCDR 1 | HCDR2 | SEQ ID No. HCDR 2 | HCDR3 | SEQ ID No. HCDR 3 |
| 16 | MOR04950 | VH3 | GFTFSSYWMS | 56 | WVSVIEHKSFGSATFYAASVKG | 64 | HGIDFDH | 72 |
| 17 | MOR04954 | VH3 | GFTFSSYWMS | 18 | WVSVIEHKDKGGTTYYAASVKG | 18 | HGIDFDH | 18 |
| 18 | MOR04920 | VH3 | GFTFSSYWMS | 15 | WVSSIEHKDAGYTTWYAAGVKG | 15 | HGIDFDH | 15 |
| P | MOR04516 | VH5 | GYSFTNYYIG | 7 | WMGIIYPTDSYTNYSPSFQG | 7 | GIPFRMRGFDY | 7 |
| 19 | MOR04947 | VH | GYSFTNYYIG | 19 | WMGIIYPGTSYTIYSPSFGQ | 19 | GIPFRMRGFDY | 19 |

TABLE 11B

| Amino acid sequences of Light Chain CDR's | | | | | | | | | |
|---|---|---|---|---|---|---|---|---|---|
| | MOR Antibody No. | $V_L$ | HCDR1 | SEQ ID No. | HCDR2 | SEQ ID No. | hCDR3 | SEQ ID No. | Comment |
| P | 04455 | K1 | RASQDISNYLH | 22 | LLIYGASNLQS | 22 | QQYDSIPM | 22 | |
| 1 | 04918 | K1 | RASQDISNYLH | 73 | LLIYGASNLQS | 81 | QQYDSIPM | 89 | |
| P | 04456 | K3 | RASQNLFSPYLA | 23 | LLIYGASNRAT | 23 | QQYGDEPI | 23 | |
| 2 | 04907 | K3 | RASQNLFSPYLA | 27 | LLIYGASNRAT | 27 | QQYLSLPT | 27 | |
| 3 | 04946 | K3 | RASQNLFSPYLA | 29 | LLIYGASNRAT | 29 | QQYLTLPL | 29 | |
| 4 | 04949 | K3 | RASQNLFSPYLA | 74 | LLIYGASNRAT | 82 | QQYLFPL | 90 | |
| 5 | 04913 | K3 | RASQNLFSPYLA | 28 | LLIYGASNRAT | 28 | QQYMTLPL | 28 | FW4 mutation |
| P | 04461 | L2 | TGTSSDVGGFNYVS | 24 | LMIHDGSNRPS | 24 | STWDMTVDF | 24 | |
| 6 | 04911 | L2 | TGTSSDVGGFNYVS | 75 | LMIHDGSNRPS | 83 | STWDMTVDF | 91 | |
| 7 | 04922 | L2 | TGTSSDVGGFNYVS | 76 | LMIHDGSNRPS | 84 | STWDMTVDF | 92 | |
| 8 | 04910 | L2 | TGTSSDVGGFNYVS | 30 | LMIHDGSNRPS | 30 | QSWDVSPITA | 30 | |
| 9 | 04948 | L2 | TGTSSDVGGFNYVS | 32 | LMIHDGSNRPS | 32 | QTWDSLSFF | 32 | |
| 10 | 04919 | L2 | TGTSSDVGGFNYVS | 77 | LMIHDGSNRPS | 85 | QSWGVGPGGF | 93 | |
| 11 | 04921 | L2 | TGTSSDVGGFNYVS | 31 | LMIHDGSNRPS | 31 | QTWATSPLSS | 31 | |
| P | 04470 | L2 | TGTSSDLGGYNYVS | 25 | LMIYDVNNRPS | 25 | QSYASGNTKV | 25 | |
| 12 | 04914 | L2 | TGTSSDLGGYNYVS | 33 | LMIYDVNNRPS | 33 | QSYTYTPISP | 33 | |
| 13 | 04945 | L2 | TGTSSDLGGYNYVS | 35 | LMIYDVNNRPS | 35 | QTYDQIKLSA | 35 | |
| 14 | 04951 | L2 | TGTSSDLGGYNYVS | 78 | LMIYDVNNRPS | 86 | QSYDPFLDVV | 94 | |
| 15 | 04952 | L2 | TGTSSDLGGYNYVS | 79 | LMIYDVNNRPS | 87 | QSYDSPTDSV | 95 | |
| 16 | 04950 | L2 | TGTSSDLGGYNYVS | 80 | LMIYDVNNRPS | 88 | QSYASGNTKV | 96 | |
| 17 | 04954 | L2 | TGTSSDLGGYNYVS | 37 | LMIYDVNNRPS | 37 | QSYASGNTKV | 37 | |
| 18 | 04920 | L2 | TGTSSDLGGYNYVS | 34 | LMIYDVNNRPS | 34 | QSYASGNTKV | 34 | HCDR2 point mutation |
| P | 04516 | L1 | SGSSSNIGSSFVN | 26 | LLIGNNSNRPS | 26 | ASFDMGSPNV | 26 | Potential N-glycosyl sites |

TABLE 11B-continued

Amino acid sequences of Light Chain CDR's

| | MOR Antibody No. | $V_L$ | HCDR1 | SEQ ID No. | HCDR2 | SEQ ID No. | hCDR3 | SEQ ID No. | Comment |
|---|---|---|---|---|---|---|---|---|---|
| 19 | 04947 | L1 | SGSSSNIGSSFVN | 38 | LLIGNNSNRPS | 38 | ASFDMGSPNV | 38 | Potential N-glycosyl site |
| | consensus1 | | RASQxxxxxYx | 131 | LLIYGASNxxx | 132 | QQYxxxPx | 133 | |
| | consensus2 | | TGTSSDVGGFNYVS | 134 | LMIxDxxNRPS | 135 | xxWDxxxxx | 136 | |

The sequence analysis showed that five of the six parental (P) Fabs yielded affinity-improved successors. MOR04461 and MOR04470 could be optimized in HCDR2 as well as in LCDR3. No optimized successors of MOR04454 are obtained. In addition, high homology appears between disparate parent antibodies, as shown in consensus1 and consensus2 sequences for the various CDRs in Table 11B Similar consensus sequences may be provided for parent sequences shown in Table 10A using methods well known to one skilled in the art.

In addition, it is determined that MOR04920 has a mutation in the HCDR2 region (a Ser residue to a Gly at pos. 73 according to the numbering scheme published by Honegger and Pluckthun, 2001 J Mol Biol 309.3:657-670 thus deviating from the HuCAL® design.

MOR04913 is shown to have a point mutation in framework 4 of the kappa light chain (Lys to Asn exchange at position 148). As this position is not expected to have an effect on the binding properties of the antibody the mutation is reverted back to the germline/HuCAL® composition during IgG conversion, yielding antibody MOR05145.

MOR04947 has a potential glycosylation site in LCDR2. This site is not removed as MOR04947 is selected only as one of the back-up candidates.

Example 7

Production of HuCAL Immunoglobulins

Conversion into the IgG Format

In order to express full length immunoglobulin (Ig), variable domain fragments of heavy ($V_H$) and light chains ($V_L$) are subcloned from the pMORPH®X9_FH Fab expression vectors either into the pMORPH®_h_Ig or the pMORPH®2_h_Ig vector series for human IgG1 and human IgG4. Alternative vectors may be used for human IgG2. Restriction enzymes EcoRI, MfeI, and BlpI are used for subcloning of the $V_H$ domain fragment into pMORPH®_h_IgG1 and pMORPH®_h_IgG4. Restriction enzymes MfeI and BlpI are used for subcloning of the $V_H$ domain fragment into pMORPH®2_h_IgG1f and pMORPH®2_h_IgG4. Subcloning of the $V_L$ domain fragment into pMORPH®_h_Igκ and pMORPH®2_h_Igκ is performed using the EcoRV and BsiWI sites, whereas subcloning into pMORPH®_h_Igλ and pMORPH®2_h_Igλ2 is done using EcoRV and HpaI.

Transient Expression and Purification of Human IgG

HEK293 cells are transfected with an equimolar amount of IgG heavy and light chain expression vectors. On days 4 or 5 after transfection, the cell culture supernatant is harvested. After adjusting the pH of the supernatant to 8.0 and sterile filtration, the solution is subjected to standard protein A column chromatography (Poros 20A, PE Biosystems).

Conversion of Parental Fabs into the IgG Formats

In parallel to the start of the affinity maturation, MOR04454, MOR04456, and MOR04470 are cloned into the pMORPH®_h_IgG1 and pMORPH®_h_IgG4 expression vectors. Alternative constructs may be used for creation of IgG2 expression vectors. Small scale expression is performed by transient transfection of HEK293 cells and the full length immunoglobulins are purified from the cell culture supernatant.

The data show by size exclusion chromatography that the antibodies are in monomeric form. Testing in the Wnt3a-dependent reporter assay proved that the proteins are functional.

Example 8

Amino Acid Sequences and Nucleotide Sequences of Genes Optimized for Expression To increase mammalian expression, changes are introduced into the heavy and the light chains of Fabs herein for optimization of codon usage for expression in a cell. It is known that several negatively cis-acting motifs decrease expression in mammals. The optimization process herein removes negative cis-acting sites (such as splice sites or poly (A) signals) which negatively influence expression. The optimization process herein further enriches GC content, to prolong mRNA half-life.

Variable light and heavy chain regions are optimized using a clone of a Fab, MOR04945 (full length light chain parental nucleotide sequence is SEQ ID NO: 98 and full length heavy chain parental nucleotide sequence is SEQ ID NO: 102), isolated herein by selection with phage display. Then the nucleotide sequences encoding each of the entire light and heavy chains of this and other clones are each optimized using these procedures.

Optimization Process for $V_H$ and $V_L$ Chains of MOR04945

For optimizing the nucleotide sequence and amino acid sequence of each of the $V_L$ and $V_H$ chains for expression in mammalian cells, the codon usage is adapted to the codon bias of mammalian genes. In addition, regions of very high (>80%) or very low (<30%) GC content are reduced or eliminated where possible. Alternatively, optimization for expression in bacteria, yeast or baculovirus would entail adapting codon usage biased for their respective genes.

During the optimization process for mammalian expression, the following cis-acting sequence motifs are avoided: internal TATA-boxes, chi-sites and ribosomal entry sites, AT-rich or GC-rich sequence stretches, RNA instability motif (ARE) sequence elements, inhibitory RNA sequence elements (INS), cAMP responsive (CRS) sequence elements, repeat sequences and RNA secondary structures, splice donor and acceptor sites including cryptic sites, and branch points. Except as indicated, introduction of MluI and HindIII sites is avoided in the process of optimizing the nucleotide sequence of the $V_L$ chain. Except as indicated, introduction of MlyI and BstEII sites is avoided in the process of optimizing the nucleotide sequence of the $V_H$ chain.

Amino Acid Sequences of $V_H$ and $V_L$ Chains of MOR04945 Optimized for Expression Codon usage is adapted to that of mammals to enable higher and more stable expression rates in a mammalian cell for the resulting optimized amino acid sequences for the $V_H$ and $V_L$ chains of the clone MOR04945 described above. See Example 5.

Table 12A below shows the sense and anti-sense (AS) nucleotide sequences of the variable light chain (SEQ ID NO: 120) and the resulting variable light chain amino acid (designated AA) sequence (SEQ ID NO: 118) as optimized for expression.

TABLE 12A

Nucleotide sense and antisense sequences, and amino acid sequences chain of $V_H$ optimized for expression

```
       MluI     EcoRV                                     BstNI
       ACGCGTTGCGATATCGCCCTGACCCAGCCCGCCAGCGTGTCCGGCAGCCCTGGCCAGAGC  (Sense)
1      ---------+---------+---------+---------+---------+---------+
       TGCGCAACGCTATAGCGGGACTGGGTCGGGCGGTCGCACAGGCCGTCGGGACCGGTCTCG  (AS)
       T__R__C__D__I__A__L__T__Q__P__A__S__V__S__G__S__P__G__Q__S__  (AA)

               PvuII                 BstNI                  BstNI
       ATCACCATCAGCTGTACCGGCACCAGCAGCGACCTGGGCGGCTACAACTACGTGTCCTGG  (Sense)
61     ---------+---------+---------+---------+---------+---------+
       TAGTGGTAGTCGACATGGCCGTGGTCGTCGCTGGACCCGCCGATGTTGATGCACAGGACC  (AS)
       I__T__I__S__C__T__G__T__S__S__D__L__G__G__Y__N__Y__V__S__W__  (AA)

       TATCAGCAGCACCCCGGCAAGGCCCCCAAGCTGATGATCTACGACGTGAACAACAGACCT  (Sense)
121    ---------+---------+---------+---------+---------+---------+
       ATAGTCGTCGTGGGGCCGTTCCGGGGGTTCGACTACTAGATGCTGCACTTGTTGTCTGGA  (AS)
       Y__Q__Q__H__P__G__K__A__P__K__L__M__I__Y__D__V__N__N__R__P__  (AA)

                      HinfI
       AGCGGCGTGTCCAACAGATTCAGCGGCAGCAAGAGCGGCAACACCGCCAGCCTGACCATC  (Sense)
181    ---------+---------+---------+---------+---------+---------+
       TCGCCGCACAGGTTGTCTAAGTCGCCGTCGTTCTCGCCGTTGTGGCGGTCGGACTGGTAG  (AS)
       S__G__V__S__N__R__F__S__G__S__K__S__G__N__T__A__S__L__T__I__  (AA)

             PstI
       TCTGGCCTGCAGGCTGAGGACGAGGCCGACTACTACTGCCAGACCTACGACCAGATCAAG  (Sense)
241    ---------+---------+---------+---------+---------+---------+
       AGACCGGACGTCCGACTCCTGCTCCGGCTGATGATGACGGTCTGGATGCTGGTCTAGTTC  (AS)
       S__G__L__Q__A__E__D__E__A__D__Y__Y__C__Q__R__Y__D__Q__I__K__  (AA)

                                   HindIII
       CTGTCCGCCGTGTTTGGCGGCGGAACAAAGCTT  (Sense) (SEQ ID NO: 120)
301    ---------+---------+---------+---
       GACAGGCGGCACAAACCGCCGCCTTGTTTCGAA  (AS)
       L__S__A__V__F__G__G__G__T__K__L__  (AA)    (SEQ ID NO: 118)
```

Table 12B below shows sense and anti-sense variable heavy chain nucleotide sequences (SEQ ID NO: 121) and the resulting variable heavy chain amino acid (designated AA) sequence (SEQ ID NO: 119) as optimized for expression.

TABLE 12B

Nucleotide sense and antisense sequences, and amino acid sequences of $V_H$ chain optimized for expression

```
       MlyI
       HinfI                   BstNI  PvuII
       GAGTCCATTGGGAGTGCAGGCCCAGGTGCAGCTGGTGGAGAGCGGCGGAGGACTGGTGCA (Sense)
1      ---------+---------+---------+---------+---------+---------+
       CTCAGGTAACCCTCACGTCCGGGTCCACGTCGACCACCTCTCGCCGCCTCCTGACCACGT (AS)
                 G__V__Q__A__Q__V__Q__L__V__E__S__G__G__G__L__V__Q_ (AA)

        BstNI
       GCCTGGCGGCAGCCTGAGACTGAGCTGTGCCGCCAGCGGCTTCACCTTCAGCAGCTACTG (Sense)
61     ---------+---------+---------+---------+---------+---------+
       CGGACCGCCGTCGGACTCTGACTCGACACGGCGGTCGCCGAAGTGGAAGTCGTCGATGAC (AS)
       _P__G__G__S__L__R__L__S__C__A__A__S__G__F__T__F__S__S__Y__W_ (AA)
```

TABLE 12B-continued

Nucleotide sense and antisense sequences, and amino acid sequences of $V_H$ chain optimized for expression

```
                          BstNI      BstNI            BclI
    GATGAGCTGGGTGAGGCAGGCCCCTGGCAAGGGCCTGGAGTGGGTGTCCGTGATCAGCAG (Sense)
121 ---------+---------+---------+---------+---------+---------+
    CTACTCGACCCACTCCGTCCGGGGACCGTTCCCGGACCTCACCCACAGGCACTAGTCGTC (AS)
    _M__S__W__V__R__Q__A__P__G__K__G__L__E__W__V__S__V__I__S__S_ (AA)

    CGATAGCAGCAGCACCTACTACGCCGATAGCGTGAAGGGCCGGTTCACCATCAGCCGGGA (Sense)
181 ---------+---------+---------+---------+---------+---------+
    GCTATCGTCGTCGTGGATGATGCGGCTATCGCACTTCCCGGCCAAGTGGTAGTCGGCCCT (AS)
    _D__S__S__S__T__Y__Y__A__D__S__V__K__G__R__F__T__I__S__R__D_ (AA)

                          PstI
                        BspMI
    CAACAGCAAGAACACCCTGTACCTGCAGATGAACAGCCTGAGAGCCGAGGACACCGCCGT (Sense)
241 ---------+---------+---------+---------+---------+---------+
    GTTGTCGTTCTTGTGGGACATGGACGTCTACTTGTCGGACTCTCGGCTCCTGTGGCGGCA (AS)
    _N__S__K__N__T__L__Y__L__Q__M__N__S__L__R__A__E__D__T__A__V_ (AA)

                          PstI                        BstNI
               BstNI                         BstNI       BstEII
    GTACTACTGTGCCAGGCACGGCATCGACTTCGACCACTGGGGCCAGGGCACCCTGGTCAC (Sense)
301 ---------+---------+---------+---------+---------+---------+
    CATGATGACACGGTCCGTGCCGTAGCTGAAGCTGGTGACCCCGGTCCCGTGGGACCAGTG (AS)
    _Y__Y__C__A__R__H__G__I__D__F__D__H__W__G__Q__G__T__L__V__T_

    C (Sense) (SEQ ID NO: 121)
361 -
    G (AS)
    _ (AA)    (SEQ ID NO: 119)
```

Pre- and post-optimization charts may provide the percentages of sequence codons for each of the parental sequences and optimized genes respectively, and analyses the quality class of the respecting nucleotide sequences encoding the $V_H$ and $V_L$ chains. Quality value as used herein means that the most frequent codon used for a given amino acid in the desired expression system is set as 100, and the remaining codons are scaled accordingly to frequency of usage. (Sharp, P.M., Li, W. H., *Nucleic Acids Res.* 15 (3), 1987).

Figure 9:
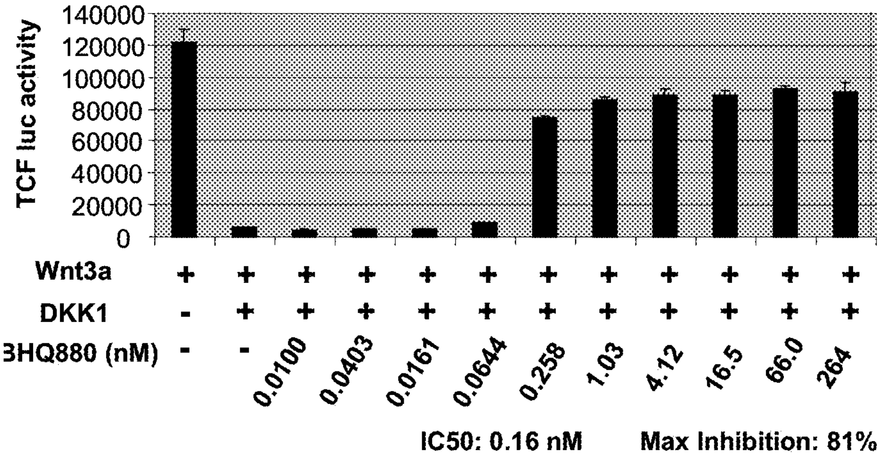
FIG. 9 is a graphic illustration of DKK1/4 antibody-associated reactivation of Wnt-regulated gene transcription downstream.

Further, the codon adaptation index (CAI) is a number that describes how well the codons of the nucleotide sequence match the codon usage preference of the target organism. The maximum value of CAI is set to 1.0, thus a CAI of >0.9 is considered as enabling high expression. The CAI for the $V_L$ chain prior to optimization is found to be 0.73, and after optimization, the CAI is determined to be 0.95. Similarly, the CAI for the $V_H$ chain prior to optimization is found to be 0.74, and after optimization, is determined to be 0.98 in optimized constructs, the GC content in the $V_L$ chain is increased from 51% for the parent sequence of MOR04945 to 62% for the optimized sequence derived from MOR04945. As shown in FIGS. 9A and 9B, the GC content in the $V_H$ chain is increased from 54% for the parent sequence of MOR04945 to 64% for the optimized derivative of MOR04945.

Optimization for Expression of Full Length Light Chains and Heavy Chains of MOR04910, MOR04945, MOR04946, and MOR05145

The optimization process is applied to each of the parent full length nucleotide sequences of the light chains of MOR04910 (SEQ ID NO: 97), MOR04945 (SEQ ID NO: 98), MOR04946 (SEQ ID NO: 99), and MOR05145 (SEQ ID NO: 100) and the parent full length nucleotide sequences of the heavy chains of MOR04910 (SEQ ID NO: 101), MOR04945 (SEQ ID NO: 102), MOR04946 (SEQ ID NO: 103), and MOR05145 (SEQ ID NO: 103).

The optimization process is used to construct each of the following light chain nucleotide sequences associated with the parent clone numbers: for clone MOR04910 the optimized nucleotide sequence is SEQ ID NO: 104; for clone MOR04945 the optimized nucleotide sequence is SEQ ID NO: 105; for clone MOR04946 the optimized nucleotide sequence is SEQ ID NO: 106, and for clone MOR05145 the optimized nucleotide sequence is SEQ ID NO: 107. Further, the optimization process is used to construct each of the following heavy chain nucleotide sequences associated with the parent clone numbers: for clone MOR04910 the optimized nucleotide sequence is SEQ ID NO: 108; for clone MOR04945 the optimized nucleotide sequence is SEQ ID NO: 109; for clone MOR04946 the optimized nucleotide sequence is SEQ ID NO: 110; and for clone MOR05145 the optimized nucleotide sequence is SEQ ID NO: 110.

The optimized light chain nucleotide sequences are associated with the following optimized light chain amino acid sequences: for clone MOR04910 the optimized amino acid sequence is SEQ ID NO: 111; for clone MOR04945 the optimized amino acid sequence is SEQ ID NO: 112; for clone MOR04946 the optimized amino acid sequence is SEQ ID NO: 113; and for clone MOR05145 the optimized amino acid sequence is SEQ ID NO: 114. The optimized heavy chain nucleotide sequences are associated with the following optimized heavy chain amino acid sequences: for clone MOR04910 the optimized amino acid sequence is SEQ ID NO: 115; for clone MOR04945 the optimized amino acid sequence is SEQ ID NO: 116; for clone MOR04946 the optimized amino acid sequence is SEQ ID NO: 117; and for clone MOR05145 the optimized amino acid sequence is SEQ ID NO: 117.

A listing of nucleotide and polypeptide sequences of contemplated full length light and heavy chain sequences are provided in Table 13A and Table 13B. Table 13A provides optimized nucleotide sequences and the polypeptides encoded by them. These nucleotide sequences are optimized to remove latent splice sites that are recognized in mammalian expression systems. Table 13B provides the parental nucleotide sequences for the clones listed in Table 13A.

TABLE 13A

| Light Chain (LC) and Heavy Chain (HC) Sequences - optimized | |
|---|---|
| LC (opt) 4910 nucleotide | SEQ ID NO: 97 |

GATATCGCACTGACCCAGCCAGCTTCAGTGAGCGGCTCACCAGGTCAGAGCATTACCATCTCGTGTACGGGTACTAGCAGCGA
TGTTGGTGGTTTTAATTATGTGTCTTGGTACCAGCAGCATCCCGGGAAGGCGCCGAAACTTATGATTCATGATGGTTCTAATC
GTCCCTCAGGCGTGAGCAACCGTTTTAGCGGATCCAAAAGCGGCAACACCGCGAGCCTGACCATTAGCGGCCTGCAAGCGGAA
GACGAAGCGGATTATTATTGCCAGTCTTGGGATGTTTCTCCTATTACTGCTGTGTTTGGCGGCGGCACGAAGCTTACCGTCCT
AGGTCAGCCCAAGGCTGCCCCCTCGGTCACTCTGTTCCCGCCCTCCTCTGAGGAGCTTCAAGCCAACAAGGCCACACTGGTGT
GTCTCATAAGTGACTTCTACCCGGGAGCCGTGACAGTGGCCTGGAAGGCAGATAGCAGCCCCGTCAAGGCGGGAGTGGAGACA
ACCACACCCTCCAAACAAAGCAACAACAAGTACGCGGCCAGCAGCTATCTGAGCCTGACGCCTGAGCAGTGGAAGTCCCACAG
AAGCTACAGCTGCCAGGTCACGCATGAAGGGAGCACCGTGGAAAAGACAGTGGCCCCTACAGAATGTTCATAG

| LC4910 (BHQ880) polypeptide | SEQ ID NO: 111 |
|---|---|

DIALTQPASVSGSPGQSITISCTGTSSDVGGFNYVSWYQQHPGKAPKLMIHDGSNRPSGVSNRFSGSKSGNTASLTISGLQAE
DEADYYCQSWDVSPITAVFGGGTKLTVLGQPKAAPSVTLFPPSSEELQANKATLVCLISDFYPGAVTVAWKADSSPVKAGVET
TTPSKQSNNKYAASSYLSLTPEQWKSHRSYSCQVTHEGSTVEKTVAPTECS

| LC (opt) 4945 nucleotide | SEQ ID NO: 98 |
|---|---|

GATATCGCACTGACCCAGCCAGCTTCAGTGAGCGGCTCACCAGGTCAGAGCATTACCATCTCGTGTACGGGTACTAGCAGCGA
TCTTGGTGGTTATAATTATGTGTCTTGGTACCAGCAGCATCCCGGGAAGGCGCCGAAACTTATGATTTATGATGTTAATAATC
GTCCCTCAGGCGTGAGCAACCGTTTTAGCGGATCCAAAAGCGGCAACACCGCGAGCCTGACCATTAGCGGCCTGCAAGCGGAA
GACGAAGCGGATTATTATTGCCAGACTTATGATCAGATTAAGTTGTCTGCTGTGTTTGGCGGCGGCACGAAGCTTACCGTCCT
AGGTCAGCCCAAGGCTGCCCCCTCGGTCACTCTGTTCCCGCCCTCCTCTGAGGAGCTTCAAGCCAACAAGGCCACACTGGTGT
GTCTCATAAGTGACTTCTACCCGGGAGCCGTGACAGTGGCCTGGAAGGCAGATAGCAGCCCCGTCAAGGCGGGAGTGGAGACA
ACCACACCCTCCAAACAAAGCAACAACAAGTACGCGGCCAGCAGCTATCTGAGCCTGACGCCTGAGCAGTGGAAGTCCCACAG
AAGCTACAGCTGCCAGGTCACGCATGAAGGGAGCACCGTGGAAAAGACAGTGGCCCCTACAGAATGTTCATAG

| LC4945 (BHQ892) polypeptide | SEQ ID NO: 112 |
|---|---|

DIALTQPASVSGSPGQSITISCTGTSSDLGGYNYVSWYQQHPGKAPKLMIYDVNNRPSGVSNRFSGSKSGNTASLTISGLQAE
DEADYYCQTYDQIKLSAVFGGGTKLTVLGQPKAAPSVTLFPPSSEELQANKATLVCLISDFYPGAVTVAWKADSSPVKAGVET
TTPSKQSNNKYAASSYLSLIPEQWKSHRSYSCQVTHEGSTVEKTVAPTECS

| LC (opt) 4946 nucleotide | SEQ ID NO: 99 |
|---|---|

GATATCGTGCTGACCCAGAGCCCGGCGACCCTGAGCCTGTCTCCGGGCGAACGTGCGACCCTGAGCTGCAGAGCGAGCCAGAA
TCTTTTTTCTCCTTATCTGGCTTGGTACCAGCAGAAACCAGGTCAAGCACCGCGTCTATTAATTTATGGTGCTTCTAATCGTG
CAACTGGGGTCCCGGCGCGTTTTAGCGGCTCTGGATCCGGCACGGATTTTACCCTGACCATTAGCAGCCTGGAACCTGAAGAC
TTTGCGGTGTATTATTGCCAGCAGTATCTTACTCTTCCTCTTACCTTTGGCCAGGGTACGAAAGTCGAGATCAAACGAACTGT
GGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAG
CAGGACACCAAGGACAGCACCTACAGCCTCAGCAGCACCCTGACGCTGAGCAAAGCAGACTACGAGAAACACAAAGTCTACGC
CTGCGAAGTCACCCATCAGGGCCTGAGCTCGCCCGTCACAAAGAGCTTCAACAGGGGAGAGTGTTAG

| LC4946 (BHQ898) polypeptide | SEQ ID NO: 113 |
|---|---|

DIVLTQSPATLSLSPGERATLSCRASQNLFSPYLAWYQQKPGQAPRLLIYGASNRATGVPARFSGSGSGTDFTLTISSLEPED
FAVYYCQQYLTLPLTFGQGTKVEIKRTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

| LC (opt) 5145 nucleotide | SEQ ID NO: 100 |
|---|---|

GATATCGTGCTGACCCAGAGCCCGGCGACCCTGAGCCTGTCTCCGGGCGAACGTGCGACCCTGAGCTGCAGAGCGAGCCAGAA
TCTTTTTTCTCCTTATCTGGCTTGGTACCACCAGAAACCAGGTCAAGCACCGCGTCTATTAATTTATGGTGCTTCTAATCGTG
CAACTGGGGTCCCGGCGCGTTTTAGCGGCTCTGGATCCGGCACGGATTTTACCCTGACCATTAGCAGCCTGGAACCTGAAGAC
TTTGCGGTGTATTATTGCCAGCAGTATATGACTCTTCCTCTTACCTTTGGCCAGGGTACGAAAGTCGAGATCAAACGAACTGT
GGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGCAGACTACGAGAAACACAAAGTCTACGC
CTGCGAAGTCACCCATCAGGGCCTGAGCTCGCCCGTCACAAAGAGCTTCAACAGGGGAGAGTGTTAG

| LC5145 (BHQ901) polypeptide | SEQ ID NO: 114 |
|---|---|

DIVLTQSPATLSLSPGERATLSCRASQNLFSPYLAWYQQKPGQAPRLLIYGASNRATGVPARFSGSGSGTDFTLTISSLEPED
FAVYYCQQYMTLPLTFGQGTKVEIKRTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

| HC (opt) 4910 nucleotide | SEQ ID NO: 101 |
|---|---|

CAGGCACAGGTCCAATTGGTGGAAACCGGCGGCGGCCTGGTGCAACCGGGCGGCAGCCTGCGTCTGAGCTGCGCGGCCTCCGG
ATTTACCTTTTCTTCTTATTGGATGTCTTGGGTGCGCCAAGCCCCTGGGAAGGGTCTCGAGTGGGTGAGCGGTATCTCTTATT
CTGGTAGCAATACCCATTATGCGGATAGCGTGAAAGGCCGTTTTACCATTTCACGTGATAATTCGAAAAACACCCTGTATCTG
CAAATGAACAGCCTGCGTGCCGAAGATACGGCCGTGTATTATTGCGCGCGTATGGGTATTGATCTTGATTATTGGGGCCAAGG
CACCCTGGTCACCGTCTCCTCAGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTCGTGACCGTGCCCTCCAGCAGCTT
GGGCACCCAGACCTACATCTGCAACGTGAATCACAAGCCCAGCAACACCAAGGTGGACAAGAGAGTTGAGCCCAAATCTTGTG

TABLE 13A-continued

Light Chain (LC) and Heavy Chain (HC) Sequences - optimized

ACAAAACTCACACATGCCCACCGTGCCCAGCACCTGAACTCCTGGGGGGACCGTCAGTCTTCCTCTTCCCCCCAAAACCCAAG
GACACCCTCATGATCTCCCGGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATCCCGGGAGGAGATGAC
CAAGAACCAGGTCAGCCTGACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTATAGCAAGCTCACCGTGGACAAG
AGCAGGTGGCAGCAGGGGAACGTCTTCTCATGCTCCGTGATGCATGAGGCTCTGCACAACCACTACACGCAGAAGAGCCTCTC
CCTGTCCCCGGGTAAATGA

HC4910 (BHQ880) polypeptide SEQ ID NO: 115

QVQLVESGGGLVQPGGSLRLSCAASGFTFSSYWMSWVRQAPGKGLEWVSGISYSGSNTHYADSVKGRFTISRDNSKNTLYLQM
NSLRAEDTAVYYCARMGIDLDYWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTTPPVLDSDGSFFLYSKLTVDKSR
WQQGNVFSCSVMHEALHNHYTQKSLSLSPCK

HC (opt) 4945 nucleotide SEQ ID NO: 102

CAGGCACAGGTGCAATTGGTGGAAAGCGGCGGCGGCCTGGTGCAACCGGGCGGCAGCCTGCGTCTGAGCTGCGCGGCCTCCGG
ATTTACCTTTTCTTCTTATTGGATGTCTTGGGTGCGCCAAGCCCCTGGGAAGGGTCTCGAGTGGGTGAGCGTTATCTCTTCTG
ATTCTAGCTCTACCTATTATGCGGATAGCGTGAAAGGCCGTTTTACCATTTCACGTGATAATTCGAAAAACACCCTGTATCTG
CAAATGAACAGCCTGCGTGCGGAAGATACGGCCGTGTATTATTGCGCGCGTCATGGTATTGATTTTGATCATTGGGGCCAAGG
CACCCTGGTCACCGTCTCCTCAGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTCGTGACCGTGCCCTCCAGCAGCTT
GGGCACCCAGACCTACATCTGCAACGTGAATCACAAGCCCAGCAACACCAAGGTGGACAAGAGAGTTGAGCCCAAATCTTGTG
ACAAAACTCACACATGCCCACCGTGCCCAGCACCTGAACTCCTGGGGGGACCGTCAGTCTTCCTCTTCCCCCCAAAACCCAAG
GACACCCTCATGATCTCCCGGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATCCCGGGAGGAGATGAC
CAAGAACCAGGTCAGCCTGACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTATAGCAAGCTCACCGTGGACAAG
AGCAGGTGGCAGCAGGGGAACGTCTTCTCATGCTCCGTGATGCATGAGGCTCTGCACAACCACTACACGCAGAAGAGCCTCTC
CCTGTCCCCGGGTAAATGA

HC4945 (BHQ892) polypeptide SEQ ID NO: 116

QVQLVESGGGLVQPGGSLRLSCAASGFTFSSYWMSWVRQAPGKGLEWVSVISSDSSSTYYADSVKGRFTISRDNSKNTLYLQM
NSLRAEDTAVYYCARHGIDFDHWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDT
LMISRTPEVTCVVVDVSKEDPEVKFNWYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGK

HC (opt) 4946 = 5145 nucleotide SEQ ID NO: 103

CAGGTGCAGCTGGTGGAGAGCGGCGGAGGACTGGTGCAGCCTGGCGGCAGCCTGAGACTGAGCTGTGCCGCCAGCGGCTTCAC
CTTCAACAACTACGGCATGACCTGGGTGAGGCAGGCCCCTGGCAAGGGCCTGGAGTGGGTGTCCGGCATCAGCGGCAGCGGCA
GCTACACCTACTACGCCGACAGCGTGAAGGGCAGGTTCACCATCAGCCGGGACAACAGCAAGAACACCCTGTACCTGCAGATG
AACAGCCTGAGAGCCGAGGACACCGCCGTGTACTACTGTGCCCGGACCATCTACATGGACTACTGGGGCCAGGGCACCCTGGT
CACCGTCTCCTCAGCCTCCACCAAGGGCCCATCGGTCTTCCCCCTGGCACCCTCCTCCAAGAGCACCTCTGGGGGCACAGCGG
CCCTGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTCGTGACCGTGCCCTCCAGCAGCTTGGGCACCCA
GACCTACATCTGCAACGTGAATCACAAGCCCAGCAACACCAAGGTGGACAAGAGAGTTGAGCCCAAATCTTGTGACAAAACTC
ACACATGCCCACCGTGCCCAGCACCTGAACTCCTGGGGGGACCGTCAGTCTTCCTCTTCCCCCCAAAACCCAAGGACACCCTC
ATGATCTCCCGGACCCCTGAGGTCACATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACAACAGCACGTACCGTGTGGTCAGCGTCCTCA
CCGTCCTGCACCAGGACTGGCTGAATGGCAAGGAGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCTGCCCCCATCCCGGGAGGAGATGACCAAGAACCA
GGTCAGCCTGACCTGCCTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTATAGCAAGCTCACCGTGGACAAGAGCAGGTGG
CAGCAGGGGAACGTCTTCTCATGCTCCGTGATGCATGAGGCTCTGCACAACCACTACACGCAGAAGAGCCTCTCCCTGTCCCC
GGGTAAATGA

HC4946 = 5145 (BHQ898/901) polypeptide SEQ ID NO: 117

QVQLVESGGGLVQPGGSLRLSCAASGFTFNNYGMTWVRQAPGKGLEWVSGISGSGSYTYYADSVKGRFTISRDNSKNTLYLQM
NSLRAEDTAVYYCARTIYMDYWGQGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSKEDPEVKFNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK

TABLE 13B

Light Chain (LC) and Heavy Chain (HC) Sequences - parental

LC (parental) 4910 nucleotide SEQ ID NO: 104

GATATCGCCCTGACCCAGCCCGCCAGCGTGTCCGGCAGCCCTGGCCAGAGCATCACCATCAGCTGTACCGGCACCAGCAGCGA
TGTGGGCGGCTTCAACTACGTGTCCTGGTATCAGCAGCACCCCGGCAAGGCCCCCAAGCTGATGATCCACGACGGCAGCAATA
GACCCAGCGGCGTGTCCAATAGATTCAGCGGCAGCAAGAGCGGCAACACCGCCAGCCTGACCATCAGCGGCCTGCAGGCTGAG
GACGAGGCCGACTACTACTGCCAGAGCTGGGATGTGAGCCCCATCACCGCCGTGTTTGGCGGCGGAACAAAGCTTACCGTCCT
AGGTCAGCCCAAGGCTGCCCCCTCGGTCACTCTGTTCCCGCCCTCCTCTGAGGAGCTTCAAGCCAACAAGGCCACACTGGTGT
GTCTCATAAGTGACTTCTACCCGGGAGCCGTGACAGTGGCCTGGAAGGCAGATAGCAGCCCCGTCAAGGCGGGAGTGGAGACA
ACCACACCCTCCAAACAAAGCAACAACAAGTACGCGGCCAGCAGCTATCTGAGCCTGACGCCTGAGCAGTGGAAGTCCCACAG
AAGCTACAGCTGCCAGGTCACGCATGAAGGGACCACCGTGGAAAAGACAGTGGCCCCTACAGAATGTTCATAG

LC (parental) 4945 SEQ ID NO: 105

GATATCGCCCTGACCCAGCCCGCCAGCGTGTCCGGCAGCCCTGGCCAGAGCATCACCATCAGCTGTACCGGCACCAGCAGCGA
CCTGGGCGGCTACAACTACGTGTCCTGGTATCAGCAGCACCCCGGCAAGGCCCCCAAGCTGATGATCTACGACGTGAACAACA
GACCTAGCGGCGTGTCCAACAGATTCAGCGGCAGCAAGAGCGGCAACACCGCCAGCCTGACCATCTCTGGCCTGCAGGCTGAG
GACGAGGCCGACTACTACTGCCAGACCTACGACCAGATCAAGCTGTCCGCCGTGTTTGGCGGCGGAACAAAGCTTACCGTCCT
AGGTCAGCCCAAGGCTGCCCCCTCGGTCACTCTGTTCCCGCCCTCCTCTGAGGAGCTTCAAGCCAACAAGGCCACACTGGTGT
GTCTCATAAGTGACTTCTACCCGGGAGCCGTGACAGTGGCCTGGAAGGCAGATAGCAGCCCCGTCAAGGCGGGAGTGGAGACA
ACCACACCCTCCAAACAAAGCAACAACAAGTACGCGGCCAGCAGCTATCTGAGCCTGACGCCTGAGCAGTGGAAGTCCCACAG
AAGCTACAGCTGCCAGGTCACGCATGAAGGGAGCACCGTGGAAAAGACAGTGGCCCCTACAGAATGTTCATAG

LC (parental) 4946 nucleotide SEQ ID NO: 106

GACATCGTGCTGACCCAGAGCCCCGCCACCCTGAGCCTGAGCCCTGGCGAGAGAGCCACCCTGTCTTGTAGGGCCAGCCAGAA
CCTGTTCAGCCCTTACCTGGCCTGGTATCAGCAGAAGCCCGGCCAGGCCCCCAGACTGCTGATCTACGGCGCCAGCAACAGAG
CCACCGGCGTGCCCGCCAGATTCAGCGGCAGCGGCTCCGGCACCGACTTCACCCTGACCATCAGCAGCCTGGAGCCTGAGGAT
TTCGCCGTGTACTACTGCCAGCAGTACCTGACCCTGCCCCTGACCTTCGGCCAGGGCACCAAGGTCGAGATCAAACGAACTGT
GGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGCAGACTACGAGAAACACAAAGTCTACGC
CTGCGAAGTCACCCATCAGGGCCTGAGCTCGCCCGTCACAAAGAGCTTCAACAGGGGAGAGTGTTAG

LC (parental) 5145 nucleotide SEQ ID NO: 107

GACATCGTGCTGACCCAGAGCCCCGCCACCCTGAGCCTGAGCCCTGGCGAGAGAGCCACCCTGTCTTGTAGGGCCAGCCAGAA
CCTGTTCAGCCCTTACCTGGCCTGGTATCAGCAGAAGCCCGGCCAGGCCCCCAGACTGCTGATCTACGGCGCCAGCAACAGAG
CCACCGGCGTGCCCGCCAGATTCAGCGGCAGCGGCTCCGGCACCGACTTCACCCTGACCATCAGCAGCCTGGAGCCTGAGGAT
TTCGCCGTGTACTACTGCCAGCAGTACATGACCCTGCCTCTGACCTTCGGCCAGGGCACCAAGGTCGAGATCAAACGAACTGT
GGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGCAGACTACGAGAAACACAAAGTCTACGC
CTGCGAAGTCACCCATCAGGGCCTGAGCTCGCCCGTCACAAAGAGCTTCAACAGGGGAGAGTGTTAG

HC (parental) 4910 nucleotide SEQ ID NO: 108

CAGGCCCAGGTGCAGCTGGTGGAGAGCGGCGGAGGACTGGTGCAGCCTGGCGGCAGCCTGAGACTGAGCTGTGCCGCCAGCGG
CTTCACCTTCAGCAGCTACTGGATGAGCTGGGTGAGGCAGGCCCCTGGCAAGGGCCTGGAGTGGGTGTCCGGCATCAGCTACA
GCGGCAGCAATACCCACTACGCCGACAGCGTGAAGGGCAGGTTCACCATCAGCCGGGACAACAGCAAGAACACCCTGTACCTG
CAGATGAACAGCCTGAGAGCCGAGGACACCGCCGTGTACTACTGTGCCCGGATGGGCATCGACCTGGATTACTGGGGCCAGGG
CACCCTGGTCACCGTCTCCTCAGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTCGTGACCGTGCCCTCCAGCAGCTT
GGGCACCCAGACCTACATCTGCAACGTGAATCACAAGCCCAGCAACACCAAGGTGGACAAGAGAGTTGAGCCCAAATCTTGTG
ACAAAACTCACACATGCCCACCGTGCCCAGCACCTGAACTCCTGGGGGGACCGTCAGTCTTCCTCTTCCCCCCAAAACCCAAG
GACACCCTCATGATCTCCCGGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATCCCGGGAGGAGATGAC
CAAGAACCAGGTCAGCCTGACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTATAGCAAGCTCACCGTGGACAAG
AGCAGGTGGCAGCAGGGGAACGTCTTCTCATGCTCCGTGATGCATGAGGCTCTGCACAACCACTACACGCAGAAGAGCCTCTC
CCTGTCCCCGGGTAAATGA

HC (parental) 4945 nucleotide SEQ ID NO: 109

CAGGCCCAGGTGCAGCTGGTGGAGAGCGGCGGAGGACTGGTGCAGCCTGGCGGCAGCCTGAGACTGAGCTGTGCCGCCAGCGG
CTTCACCTTCAGCAGCTACTGGATGAGCTGGGTGAGGCAGGCCCCTGGCAAGGGCCTGGAGTGGGTGTCCGTGATCAGCAGCG
ATAGCAGCAGCACCTACTACGCCGATAGCGTGAAGGGCCGGTTCACCATCAGCCGGGACAACAGCAAGAACACCCTGTACCTG
CAGATGAACAGCCTGAGAGCCGAGGACACCGCCGTGTACTACTGTGCCAGGCACGGCATCGACTTCGACCACTGGGGCCAGGG
CACCCTGGTCACCGTCTCCTCAGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTCGTGACCGTGCCCTCCAGCAGCTT
GGGCACCCAGACCTACATCTGCAACGTGAATCACAAGCCCAGCAACACCAAGGTGGACAAGAGAGTTGAGCCCAAATCTTGTG
ACAAAACTCACACATGCCCACCGTGCCCAGCACCTGAACTCCTGGGGGGACCGTCAGTCTTCCTCTTCCCCCCAAAACCCAAG
GACACCCTCATGATCTCCCGGACCCCTGAGGTCACATGCGTGGTGGTGGACGTGAGCCACGAAGACCCTGAGGTCAAGTTCAA
CTGGTACGTGGACCGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAACAAAGCCCTCCCAGCCCCC

TABLE 13B-continued

| Light Chain (LC) and Heavy Chain (HC) Sequences - parental |
|---|
| ATCGAGAAAACCATCTCCAAAGCCAAAGGGCAGCCCCGAGAACCACAGGTGTACACCCTGCCCCCATCCCGGGAGGAGATGAC<br>CAAGAACCAGGTCAGCCTGACCTGCCTGGTCAAAGGCTTCTATCCCAGCGACATCGCCGTGGAGTGGGAGAGCAATGGGCAGC<br>CGGAGAACAACTACAAGACCACGCCTCCCGTGCTGGACTCCGACGGCTCCTTCTTCCTCTATAGCAAGCTCACCGTGGACAAG<br>AGCAGGTGGCAGCAGGGGAACGTCTTCTCATGCTCCGTGATGCATGAGGCTCTGCACAACCACTACACGCAGAAGAGCCTCTC<br>CCTGTCCCCGGGTAAATGA |
| HC (parental) 4946 = 5145 nucleotide SEQ ID NO: 110 |
| CAGGTGCAATTGGTGGAAAGCGGCGGCGGCCTGGTGCAACCGGGCGGCAGCCTGCGTCTGAGCTGCGCGGCCTCCGGATTTAC<br>CTTTAATAATTATGGTATGACTTGGGTGCGCCAAGCCCCTGGGAAGGGTCTCGAGTGGGTGAGCGGTATCTCTGGTTCTGGTA<br>GCTATACCTATTATGCGGATAGCGTGAAAGGCCGTTTTACCATTTCACGTGATAATTCGAAAAACACCCTGTATCTGCAAATG<br>AACAGCCTGCGTGCGGAAGATACGGCCGTGTATTATTGCGCGCGTACTATTTATATGGATTATTGGGGCCAAGGCACCCTGGT<br>CACCGTCTCCTCAGCCTCCACCAAGGGCCCATCGGTCTTCCCCCTGGCACCCTCCTCCAAGAGCACCTCTGGGGGCACAGCGG<br>CCCTGGGCTGCCTGGTCAAGGACTACTTCCCCGAACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGTCGTGACCGTGCCCTCCAGCAGCTTGGGCACCCA<br>GACCTACATCTGCAACGTGAATCACAAGCCCAGCAACACCAAGGTGGACAAGAGAGTTGAGCCCAAATCTTGTGACAAAACTC<br>ACACATGCCCACCGTGCCCAGCACCTGAACTCCTGGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCACGAAGACCCTGAGGTCAAGTTCAACTGGTACGT<br>GGACGGCGTGGAGGTGCATAATGCCAAGACAAAGCCGCGGGAGGAGCAGTACAACAGCACGTACCGTGTGGTCAGCGTCCTCA<br>CCGTCCTGCACCAGGACTGGCTGAATGGCAAGGAGTACAAGTGCAAGGTCTCCAACAAAGCCCTCCCAGCCCCCATCGAGAAA<br>ACCATCTCCAAAGCCAAAGGGCAGCCCCGAGAACCACAGGTGTACACCCTGCCCCCATCCCGGGAGGAGATGACCAAGAACCA<br>GGTCAGCCTGACCTGCCTGGTCAAAGGCTTCTATCCCAGCGACATCGCCGTGGAGTGGGAGAGCAATGGGCAGCCGGAGAACA<br>ACTACAAGACCACGCCTCCCGTGCTGGACTCCGACGGCTCCTTCTTCCTCTATAGCAAGCTCACCGTGGACAAGAGCAGGTGG<br>CAGCAGGGGAACGTCTTCTCATGCTCCGTGATGCATGAGGCTCTGCACAACCACTACACGCAGAAGAGCCTCTCCCTGTCCCC<br>GGGTAAATGA |

Example 9

Bioactivity Assays

The biological activity of a neutralizing anti-DKK1/4 antibody is measured in a reporter gene assay, using the genetically modified cell line HEK293 T/17 STF_70 IRES_Krm_(17) called SuperTopflash Krm17. This cell line is derived from the human embryonic kidney cell HEK293 and is stably transfected with i) a reporter construct in which the promoter TCF is fused upstream of the firefly luciferase gene and ii) a construct leading to overexpression of Krm on the surface of this cell. In this cell line, exposure to the Wnt protein stimulates the expression of luciferase in a dose-dependent manner. Addition of graded amounts of anti-DKK1/4 antibody to a fixed, sub-maximal dose of DKK1 in the presence of Wnt causes an increase in the expression of luciferase during an incubation period of sixteen hours. At the end of this period, the amount of luciferase is quantified based on its enzymatic activity in the cell lysate. Luciferase catalyses the conversion of the substrate luciferin to oxyluciferin, a chemiluminescent product. The resultant glow-type chemi-luminescence is then determined with an appropriate luminometer.

The biological potency of a neutralizing anti-DKK1/4 antibody test sample is determined by comparing its ability to increase the luciferase expression to that of a reference standard. The samples and standard are normalized on the basis of protein content. Relative potency is then calculated using a parallel line assay according to the European Pharmaco-poeia 1. The final result is expressed as relative potency (in percent) of a sample compared to the reference standard.

Example 10

In Vitro Activity on Relevant Biological Targets

Lead FAbs are selected that have affinities in the low nanomolar range and potent activity in the cellular assay. The physiological binding partners for DKK1 are LRP5/6 ($K_{a\sim340}$ pM) and Kremen 1 and 2 ($K_{a\sim280}$ pM) [Mao 2001][Mao 2002]. Given these high affinity interactions, it is desirable to further improve affinity in order to better compete with the physiological DKK1 interactions. To increase affinity and biological activity of the selected FAbs, CDR-L3 and CDR-H2 regions are optimized in parallel by cassette mutagenesis using trinucleotide directed mutagenesis [Virnekas 1994] [Knappik 2000][Nagy 2002].

Following affinity maturation, a FAb is selected that has low picomolar affinity, reactivates DKK1 inhibited wnt signaling with an EC50 under 1 nM, and cross reacts with cynomolgus monkey, mouse, and rat DKK1. The variable regions of this FAb are then engineered into two different human IgG1 frameworks.

Anti-DKK1/4 antibody has high affinity for human DKK1 (2 pM) with binding kinetics typical for an antibody of this affinity. See FIG. 6.

Figure 6:
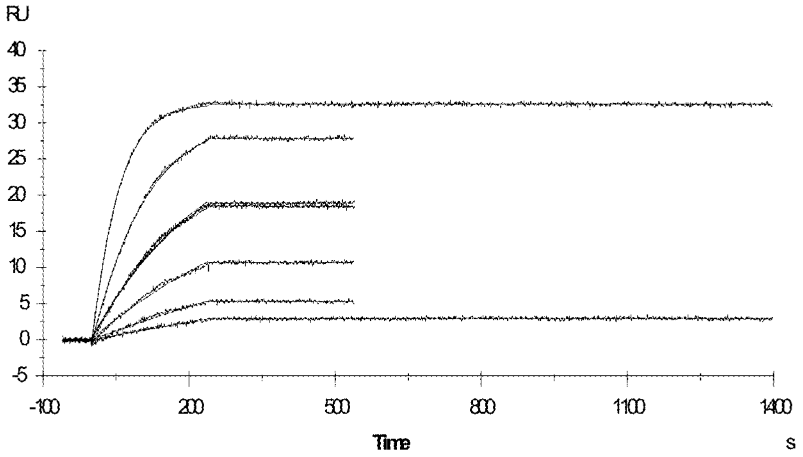
FIG. 6A is a graphic illustration of the surface plasmin resonance measurement of an anti-DKK1/4 antibody binding to DKK1.
FIG. 6B is a tabulation of calculated binding affinity and kinetic values.

FIG. 6. METHODS: The binding affinity and kinetics of lead candidates and rhDKK1 (recombinant human DKK1) (Batch BTP7757) are measured using surface plasmon resonance with a Biacore T100 (Biacore, Uppsala, Sweden) instrument containing a CM5 (S) sensor chip (Cat#BR-1006-68). Anti-Human IgG1 Fc (Jackson Immuno Research, Cat#109-006-098) is immobilized onto each flow cell, followed by capture of a lead candidate at an expected capture of about 100 RU. Finally, six concentrations of DKK1 (range 0.195-6.25 nM), with one repeat concentration, is run over the chip. Flow cells are activated for binding of DKK1 for 240 seconds, and disassociation is followed for 30 minutes. The normalized data (background subtracted) are fit to a 1:1 binding with mass transport model using Kinetics analysis in BIA evaluation 1.0 software. This experiment is carried out in triplicate, and data presented are the average of these three experiments with standard deviation.

Example 11

Epitope Mapping

Mature DKK1 is a 266 amino acid protein with two cysteine rich regions (Cys-1 and Cys-2). The Cys-2 domain is responsible for binding both LRPs and Kremen proteins and is necessary and sufficient for inhibition of Wnt signaling [Li 2002] [Brott 2002] Immunoprecipitation experiments (FIG. 7A, 7B) demonstrate that anti-DKK1/4 antibody binds specifically to the Cys-2 domain, but not the Cys-1 domain. anti-DKK1/4 antibody is only weakly active in Western blotting with denatured DKK1 and in a peptide mapping experiment is not found to specifically bind any of the overlapping 15 amino acid peptides covering the length of the protein (JTP), suggesting that anti-DKK1/4 antibody likely recognizes a non-linear epitope within Cys-2.

Figure 7:
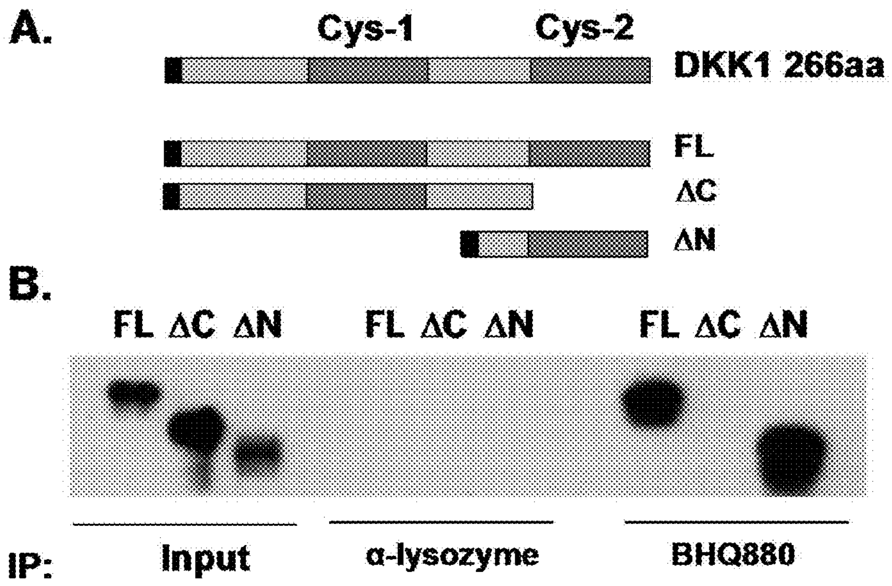
FIG. 7A is a schematic representation of full-length and truncated DKK1 for use in epitope mapping.
FIG. 7B depicts binding of an antibody of the invention to the DKK1 proteins and fragments of FIG. 7A.

FIG. 7(A) shows a schematic representation of full-length and truncated DKK1. Full-length (FL, containing residues 1-266), carboxyl terminal truncated (ΔC, containing residues 1-185), and amino terminal truncated (ΔN, containing residues 1-60 plus residues 157-266), are fused with an HA epitope at their C termini, and cloned into a mammalian expression vector under the control of the cytomegalovirus (CMV) promoter. FIG. 7(B) depicts binding of a neutralizing anti-DKK1/4 antibody and DKK1 proteins. Conditioned medium from transiently transfected Hek293 cells expressing containing full length, amino truncated, carboxyl terminal truncated DKK1 proteins are incubated with anti-lysozyme IgG1 control or the anti-DKK1/4 antibodies for 2 hrs at room temperature, and immunocomplexes are collected on protein G beads, resolved by SDS-PAGE, transferred, and blotted with an anti-HA antibody. 1/10 of total input is loaded as control.

Example 11

Epitope Mapping—N-Glycosylation

A number of proteins within the Wnt signaling pathway are covalently modified by post-translational enzymes which regulate their cellular activity. DKK family members, including DKK1, are modified by N-glycosylation [Krupnik 1999]. DKK1 has one theoretical N-linked glycosylation site at amino acid 256 within the Cys-2 domain. Given the highly conserved nature of the Cys-2 domain, and the potential binding site of both DKK1 for LRP6 and anti-DKK1/4 antibody for DKK1 we sought to determine if anti-DKK1/4 antibody recognized the N-glycosylated form of DKK1. An ELISA demonstrates that anti-DKK1/4 antibody recognizes the N-glycosylated form of rhDKK1 much better then the specifically N-linked de-glycosylated form of rhDKK1 TABLE 14A. While the same proteins are recognized equally well with a second antibody (anti-HIS), directed towards the fused epitope tag region of the recombinant protein. This difference in affinity is quantitated by using surface plasmon resonance and found anti-DKK1/4 antibody to have 100 fold higher KD to the glycosylated rhDKK1, then to the de-glycosylated protein, see TABLE 14B.

TABLE 14A

| Percent Binding - Glycosylation dependence of anti-DKK1/4 antibody binding to DKK1 | | |
|---|---|---|
| Antibody | WT DKK1 | DKK1 (dyglycosylated) |
| anti-HIS tag | 100% | 100% |
| anti-DKK1/4 | 100% | 12-18% |

TABLE 14B

| surface plasmon resonance | | | |
|---|---|---|---|
| Protein | Ka (1/Ms) | Kd (1/s) | KD (M) |
| WT DKK1 | 7.449E+6 | 2.319E−5 | 3.113E−12 |
| DKK1 (N-degly) | 1.424E+6 | 3.071E−4 | 2.157E−10 |

The binding of anti-DKK1/4 antibody to wild type (WT) rhDKK1 (HEK HIS epitope tagged Batch#BTP7757) and N-linked deglycosylated (N-DEGLY, N-linked deglycosylated with the enzyme PNGase F (Sigma, Cat#E-DEGLY) rhDKK1 is measured by ELISA. Briefly, a high binding ELISA (Nunc#442404) plate is coated with 1 μg/ml WT or N-DEGLY DKK1. The ratio of both anti-DKK1/4 antibody and anti-HIS antibody binding to WT DKK1 as compared to their respective binding of N-DEGLY is shown. This experiment is carried out with three different concentrations (data for one representative concentration is shown), all concentrations had similar results. B. The binding affinity and kinetics of anti-DKK1/4 antibody to both WT and N-DEGLY DKK1 (HEK293 Batch#BTP7757) are measured using a Biacore T100. anti-DKK1/4 antibody consistently had a 100 fold lower affinity for N-DEGLY DKK1 then it does for WT DKK1.

Example 12

Percent Identity of DKK Family Members

The human Dickkopf family consists of four paralogs (see Table 15), three of which (DKK1, 2, & 4) bind to LRP6 and Kremen proteins, induce internalization of LRP5/6 and inhibit canonical Wnt signaling [Mao 2001] [Mao 2003]. DKK2 also synergizes with LRP6 overexpression to enhance Wnt signaling, but co-expression of LRP6 and Kremen2 restores DKK2 inhibition of the pathway [Mao 2003]. Thus DKK2 can act as both an agonist and an antagonist depending on the cellular context. DKK3 is the least conserved of the family members, including within the Cys-2 domain responsible for LRP5/6 and Kremen interactions and is distinct from the other DKK family members as it does not bind LRPs or Kremens and does not block Wnt signaling [Mao 2001] [Mao 2003].

TABLE 15

| Percent identity of DKK family members across the whole protein and within Cys-2 domains. | | | | |
|---|---|---|---|---|
| | | DKK2 | DKK3 | DKK4 |
| Whole Protein | DKK1 | 38.7 | 15.5 | 32.5 |
| | DKK2 | — | 13.4 | 34.6 |
| | DKK3 | — | — | 15.1 |
| Cys-2 Domain | DKK1 | 69.3 | 23.0 | 56.6 |
| | DKK2 | — | 24.1 | 54.7 |
| | DKK3 | — | — | 20.8 |

Homology among members of the DKK family is evaluated (Vector NTI Advanced 9.1.0) using AlignX algorithm for pairwise sequence alignments comparing ratios of amino acid identities. Gap opening and gap extension penalties of 10 and 0.1 respectively are applied. This evaluation included comparisons of whole proteins, as well as comparisons of Cys-2 domains only. As indicated in the table above, DKKs 1, 2 and 4 share 30-40% amino acid sequence homology across the entire protein. Comparison of Cys-2 domains alone shows DKKs 1 and 2 share 69% homology within this region, while DKK4 shares roughly 57% with the same domain of DKKs 1 and 2. DKK3 shows the lowest level of homology to other family members. Amongst all members homology within the Cys-2 domain is greatest.

Example 13

Affinity of Anti-DKK1/4 Antibody for Human DKK Family Members

In addition to binding DKK1, anti-DKK1/4 antibody also binds to DKK4, see Table 16. While the affinity for DKK4 is approximately 100 fold less than for DKK1, it is still subnanomolar and therefore likely biologically and clinically relevant. Of note, neither DKK2 nor DKK4 conserve the Asparagine residue that is predicted to be targeted for glycosylation in the Cys-2 domain of DKK1. Preliminary immunoprecipitation experiments suggest that anti-DKK1/4 antibody does not specifically bind DKK2. The binding affinity of anti-DKK1/4 antibody binding to DKK2 will be determined following successful purification of DKK2. Consistent with the distinct function and binding properties of DKK3, anti-DKK1/4 antibody does not bind DKK3.

TABLE 16

Affinity of anti-DKK1/4 antibody for human DKK family members

| DKK Family Member | $K_D$ |
|---|---|
| DKK1 | 2.0 × 10-12M (±0.7) |
| DKK2 | ND |
| DKK3 | NSB |
| DKK4 | 2.97 × 10-10M (±1.5) |

The binding affinity and kinetics of anti-DKK1/4 antibody for other members of human DKK family of proteins are measured using a Biacore T100. As before, experiments are carried out in triplicate for proteins with significant binding to anti-DKK1/4 antibody and are reported as the average of three experiments with standard deviation. DKK3, which is the least homologous family member, did not have binding that is detectable above background levels and so is considered NSB (No Significant binding). Likewise, recent data suggests that an anti-DKK1/4 antibody of the invention also has no significant binding to DKK2.

Example 14

Anti-DKK1/4 Antibody Blocks DKK1 Binding to LRP6

Figure 8:
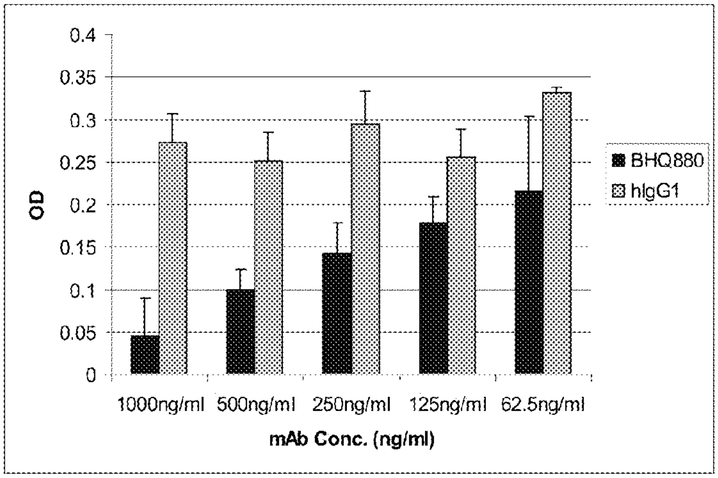
FIG. 8 is a graphic illustration of DKK1/4 antibody binding in a competition ELISA assay.

DKK1 mediates its Wnt antagonist activity through interactions with LRP5/6 and Kremen, inducing internalization and blocking Wnt induced interaction of LRP5/6 with Frizzled receptors. anti-DKK1/4 antibody competitively inhibits DKK1 binding to LRP6 in a competition ELISA assay in FIG. 8.

HEK293T cells do not express sufficient levels of endogenous LRP5 or 6 to allow visualization of DKK1 binding. However, upon co-transfection of LRP6 with a surface trafficking chaperone protein, MESD, GFP-tagged DKK1 can be detected on the cell surface, illustrating the specific nature of the DKK1/LRP6 interaction. MOR04910, which shares the same variable regions as anti-DKK1/4 antibody, specifically blocks this interaction.

The ability of anti-DKK1/4 antibody to inhibit DKK1 binding directly to LRP6 is measured by ELISA. Briefly, non-treated plates (Fisher, Cat#12565501) are coated with 1 μg/ml of recombinant LRP6 (R&D Systems Cat#1505-LR), then 500 ng/ml of rhDKK1 and a concentration curve of either anti-DKK1/4 antibody or hIgG1 (anti-lysozyme MOR3207, ACE10915) are pre-incubated on ice for 30 minutes after which they are placed onto LRP6 coated plates for 2 hours. Plates are washed and the level of DKK1 binding is detected with anti-DKK1 antibody (R&D Systems AF1096). Shown are the raw OD values (background subtracted). Increasing concentrations of anti-DKK1/4 antibody inhibits DKK1 binding directly to LRP6 in a dose dependent manner, while increasing concentrations of hIgG1 does not block DKK1 binding to LRP6.

The ability of MOR04910 to inhibit DKK1/LRP6 binding on cell surface is measured by fluorescence microscopy. HEK293T cells are either mock transfected and transiently transfected with plasmids encoding LRP6 and MESD. Cells are incubated with DKK1-GFP conditioned medium together with anti-lysozyme FAb or anti-DKK1 FAb MOR04910 for 1 hour at 37° C., and examined by fluorescence microscopy. GFP fluorescence reflects DKK1-GFP binding to overexpressed LRP6 on the plasma membrane. The anti-DKK1/4 antibody blocks DKK1 interactions with LRP6 on cell surfaces.

Example 14

Reporter Assays—Reactivation of DKK1 Inhibited TCF/LEF Gene Transcription

Canonical Wnt signaling culminates in beta-catenin translocation to the nucleus where it associates with transcription factors of the TCF/LEF family resulting in enhanced transcription of Wnt-responsive genes. A reporter assay is established using a TCF/LEF responsive promoter driving Luciferase gene transcription, facilitating detection of Wnt pathway modulation. DKK1 effectively blocks luciferase activity induced by Wnt3A conditioned media (CM) in this assay. Anti-DKK1/4 antibody reactivates DKK1 suppressed Wnt signaling with an apparent EC50 of 0.16 nM FIG. 9. Since the assay requires about 1 nM of DKK1 for complete suppression and the affinity of the antibody is 2 pM, it is likely that this EC50 reflects the sensitivity of the assay and relative amounts of each protein rather than an absolute limit of anti-DKK1/4 antibody competition.

293T cells stably transfected with SuperTopflash reporter and Kremen are treated with 10 ng/ml of rhDKK1, 50% Wnt3a conditioned medium, and various amounts of anti-DKK1/4 antibody antibody. Eighteen hours later, luciferase activity is measured by the Bright-Glo luciferase assay kit (Promega).

Example 15

Figure 10:
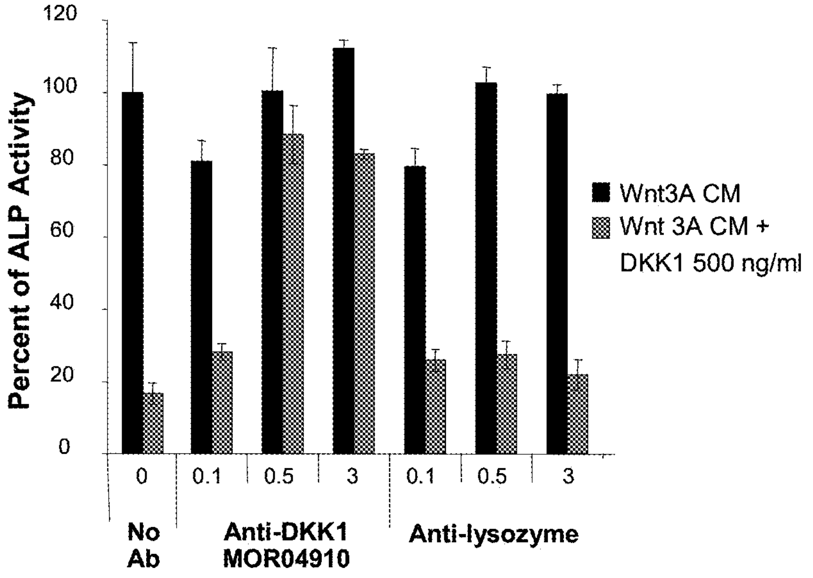
FIG. 10 is a graphic illustration of DKK1/4 antibody reversal DKK1 inhibited of ALP secretion.

Reporter Assays—Reversal of DKK1 Inhibited Alkaline Phosphatase Secretion in Pre-Osteoblast-Like Cells To determine whether anti-DKK1/4 antibody blocks DKK1 functions in a more physiological relevant setting, an in vitro assay is established to measure Wnt-mediated osteoblast differentiation of the pluripotent mouse cell line C3H10T1/2 (10T1/2), see FIG. 10. Upon osteoblast differentiation the 10T1/2 cells secrete alkaline phosphatase (AP), a phenomena which can be inhibited by DKK1. Anti-DKK1/4 antibody, but not IgG control, blocks DKK1 suppression of 10T1/2 differentiation in the presence of Wnt3A conditioned medium.

Wnt has been reported to induce proliferation and inhibit apoptosis in a number of cell contexts and activation of the Wnt pathway, as indicated by beta-catenin stabilization or nuclear localization, is frequently associated with tumor progression. Furthermore, downregulation of DKK1 in some cancers (e.g. colon carcinoma and melanoma) [Gonzalez-Sancho 2005] [Kuphal 2006], has lead some investigators to suggest that DKK1 may be a tumor suppressor for some cancers. To test whether DKK1 has effect on tumor proliferation or survival, tumor cell lines are treated with anti-DKK1/4 antibody and analyzed for changes in growth. No tumor cell line tested is found to be significantly affected by addition of anti-DKK1/4 antibody.

The effect of anti-DKK1/4 antibody on the survival and proliferation of several cancer cell lines is assessed in vitro. In this assay anti-DKK1/4 antibody (100 μg/ml) is incubated with a tumor cell line, after three days cell number is assessed by quantitation of ATP (Promega, Cell Titer Glo Assay®), as a measure of metabolically active cells with a linear relationship to cell number. This assay is carried out in three different serum concentrations (serum free, minimal growth, and complete growth). No significant changes, as compared to untreated and hIgG1 treated cells are found. Cell line supernants are analyzed for DKK1 expression by ELISA.

Example 16

Species Crossreactivity and Neutralization of DKK1

A neutralizing anti-DKK1/4 antibody is selected not for its high affinity against human DKK1 and neutralizing ability, but also based upon its crossreactivity with other species that might be used for efficacy and safety studies. anti-DKK1/4 antibody crossreacts with mouse, rat, and cynomolgus monkey (cyno, *Macaca fascicularis*) DKK1 with similar affinity as for human DKK1, see Table 17. Moreover, anti-DKK1/4 antibody neutralizes all four species' DKK1-mediated Wnt suppressive activity (Table 17), suggesting that these species should be relevant for both safety and efficacy models.

TABLE 17

Species crossreactivity and neutralization of DKK1

| DKK1 Protein | $K_D$ [pM] | Reactivation of wnt3a signaling (TOPFlash) EC50 (pM) |
|---|---|---|
| Human | 17 | 80.6 |
| Cynomolgus | 7 | 54.2 |
| Mouse | 10 | 60.5 |
| Rat | 16 | 255 |

Affinity determination for Human, Cynomolgus, Mouse, and Rat DKK1 is assayed by Solution Equilibrium Titration (SET) using the M-384 SERIES® analyzer (BioVeris, Europe). For KD determination by Solution Equilibrium Titration (SET), monomer fractions (at least 90% monomer content, analyzed by analytical SEC; Superdex75, Amersham Pharmacia) of IgG protein are used. Electrochemiluminescence (ECL) based affinity determination in solution and data evaluation are basically performed as described by [Haenel et al., 2005], the binding fit model is applied as modified according to [Piehler et al., 1997]). A constant amount of MOR4910 IgG is equilibrated with different concentrations (serial 3n dilutions) of human DKK1 (4 nM starting concentration) in solution. Biotinylated human DKK1 coupled to paramagnetic beads (M-280 Streptavidin, Dynal) and BV-tag™ (BioVeris Europe, Witney, Oxfordshire, UK) labelled goat anti-human (Fab)'2 polyclonal antibody is added and incubated for 30 min. Subsequently, the concentration of unbound IgG is quantified via ECL detection using the M-384 SERIES® analyzer (BioVeris, Europe). Affinity determination to rat, mouse, and cynomolgus DKK1 is performed essentially as described above using mouse, rat, and cynomolgus DKK1 as analyte in solution instead of human DKK1. For detection of free IgG molecules, biotinylated human DKK1 coupled to paramagnetic beads is used. MOR4910 and anti-DKK1/4 antibody neutralize human DKK1 (Novartis) with equivalent EC50, anti-DKK1/4 antibody also neutralizes monkey (Novartis), mouse(R&D Systems 1765-DK-010) and rat (Novartis) DKK1. The TOPFLASH reporter assay to human, rat, mouse, and cynomolgus DKK1 is performed essentially as described above (FIG. 9) using each species recombinant DKK1 as the inhibitor of Wnt conditioned media, instead of human DKK1. Rat recombinant DKK1 required higher concentrations of protein to achieve significant inhibition of the TOPFLASH assay.

Example 17

Effect of Anti-DKK1 Antibody on Intratibial Growth of PC3M2AC6 Xenografts

Prostate tumor metastases are unique among bone metastases in that they are overwhelmingly osteoblastic rather than osteolytic [Keller 2001]. However, even predominantly osteoblastic bone metastases have underlying regions of osteolysis and frequently have low bone mass densities (BMD) especially when patients are on androgen ablation therapy [Saad 2006]. Recently, it is demonstrated that DKK1 can act as a switch, whereby expression of DKK1 enhances osteolytic properties of a mixed osteoblastic/osteolytic prostate tumor cell line (C4-2B). In addition, shRNA suppression of DKK1 inhibited osteolytic activity of a predominantly osteolytic prostate tumor cell line (PC3) [Hall 2005] [Hall 2006]. DKK1 knockdown also inhibited intratibial growth of the tumor xenograft, leading the authors to speculate that osteolytic activity may be important for establishing a metastatic niche, but subsequent loss of DKK1 in prostatic metastases converts the tumor to an osteoblastic phenotype.

Figure 11:
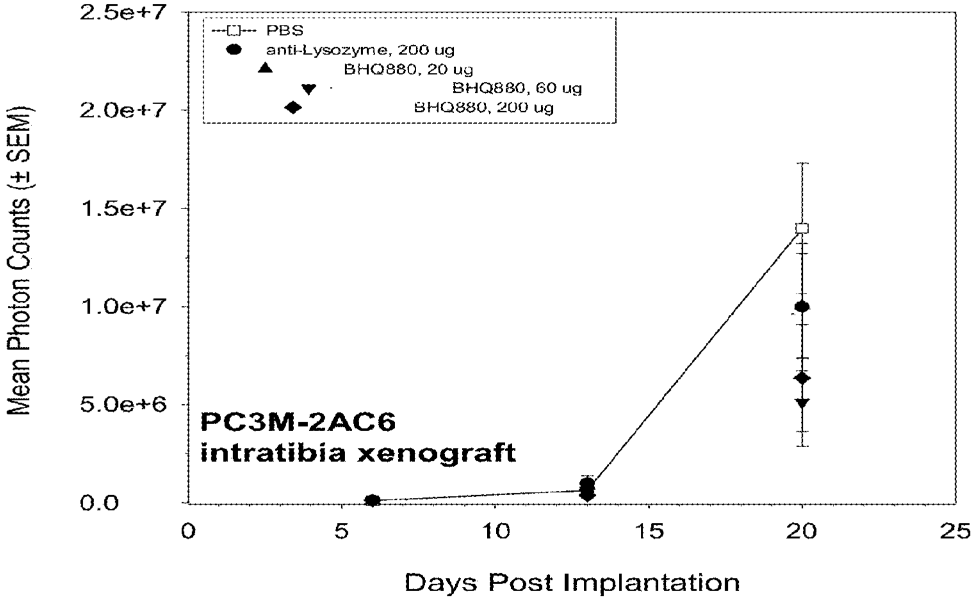
FIG. 11 is a graphic illustration of DKK1/4 antibody effects on in vivo xenografts.

An osteolytic prostate tumor model is adapted from a method by [Kim 2003]. A variant of the osteolytic prostate tumor cell line (PC3M) that stably expresses luciferase (PC3M2AC6) is injected into the tibia of mice. The growth of the tumor is monitored by luciferase while changes in bone are monitored by micro-computerized tomography (micro-CT) and histology. Rather than enhancing tumor growth, anti-DKK1/4 antibody trended toward inhibition of tumor growth. While the inhibition is not significant in any one study, it has occurred consistently in 5/5 studies conducted to date, a representative study showing effects of 3 doses of anti-DKK1/4 antibody on tumor growth is shown FIG. 11. A similar non-significant trend toward inhibition occurred with anti-DKK1/4 antibody treated mice with subcutaneous PC3M2AC6 xenografts.

Treatments are started on day 5 post implantation (0.2 million cells/animal). anti-DKK1/4 antibody is administered i.v., at doses of 20, 60, and 200 μg/mouse/day, q.d., 3 times a week for 2 weeks. Control IgG is administered i.v., at 200 μg/mouse/day, q.d., 3 times a week for 2 weeks. Vehicle control (PBS) is administered i.v., q.d., 3 times a week for 2 weeks. Final efficacy data and body weight change are calculated after treatment.

Figure 12:
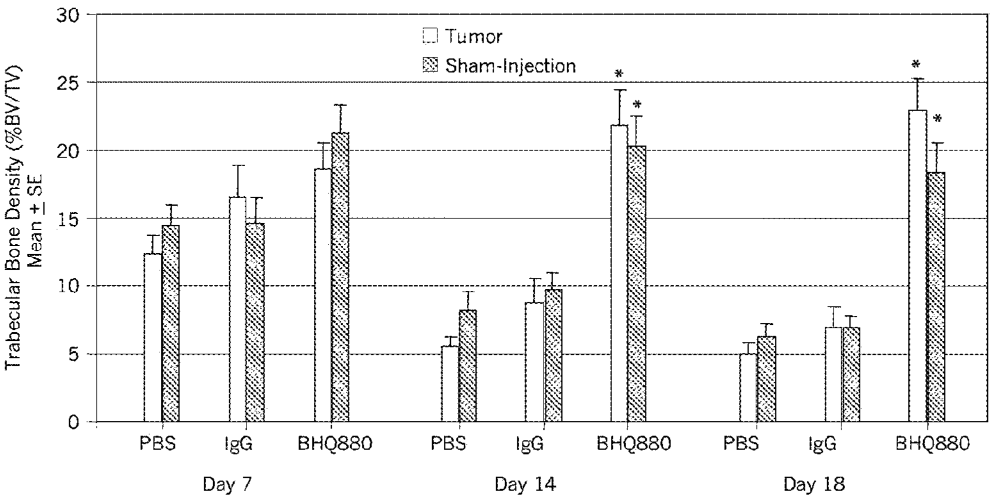
FIG. 12 is a graphic illustration of DKK1/4 antibody-associated elevation of bone density in vivo.

Using this model, we found that an anti-DKK1/4 antibody inhibits tumor-induced cortical bone damage. Effects on trabecular bone are confounded in this model by the observation that both tumor implants and sham implants cause mechanical damage to the bone that result in an initial increase in woven bone which is later remodeled causing a decrease in apparent bone volume. Relative effects of newly formed woven bone and trabeculae on overall bone volume/trabecular volume (BV/TV) ratios are therefore obscured. However, it is clear that anti-DKK1/4 antibody increases the production of bone in both tumor and sham implanted tibias and inhibits or delays the decrease in bone volume accompanying remodeling. Using the same tumor-induced osteolytic model, anti-DKK1/4 antibody demonstrates equivalent anti-osteolytic activity as Zometa, see FIG. 12. The bone metabolic effects of anti-DKK1/4 antibody are dose responsive in the range from 20-200 μg/mouse, with a minimally efficacious dose between 20 and 60 μg/mouse, see FIG. 13. Together these data suggest that anti-DKK1/4 antibody should have an impact in tumor-induced osteolytic disease, but may also be effective in non-tumor bone diseases such as osteoporosis or enhancing repair of bone fractures.

Example 18

Anti-DKK1/4 Antibody Maintains Elevated Bone Density in Both Tumor and Sham Implanted Tibias In an effort to assess pharmacodynamic markers of efficacy in the mice three serum markers of bone metabolism are analyzed: osteocalcin (OC), osteoprotegerin (OPG), and secreted receptor activator of nuclear factor KB ligand (sRANKL). These osteoblast markers are used rather than the more typical osteoclast markers due to the expected mechanism of action of the antibody. However, no consistent changes are detected in animals with tumor versus naïve animals. No correlation of bone loss, as measured by micro-CT or IHC, with any of these markers are consistently observed.

Representative examples of MicroCT reconstructions of the tibias of treated mice are shown in FIG. 12A. Cortical damage is scored from 0=no damage to 3=severe damage. FIG. 12B. Cortical damage in tumor-implanted tibias is manually scored by microCT analysis that are blinded with respect to the study groups. No cortical damage is observed in any of the sham implanted legs.

Methods: Female nude mice at age of 12 weeks old are implanted intatibially with $2\times10^5$ PC-3M2AC6 cells in the left tibia and sham-injection in the right tibia. Treatments started on day 5 post implantation. NVP-anti-DKK1/4 antibody-NX (anti-DKK1/4 antibody) and IgG control are administered i.v., at doses of 200 μg/mouse/day, q.d., 3 times a week for 2 weeks. Vehicle (PBS) control is also administered i.v., q.d., 3 times a week for 2 weeks. Animals are scanned at day 7, 14, and 18 post tumor implantation using the μ-CT VivaCT40 Scanner (SCANCO, Switzerland). Trabecular bone density (BV/TV) is analyzed as described in methods. An asterisks (*) indicates statistical significant difference from both vehicle and IgG controls (n=12) at the same time point at $p<0.05$.

Figure 13:
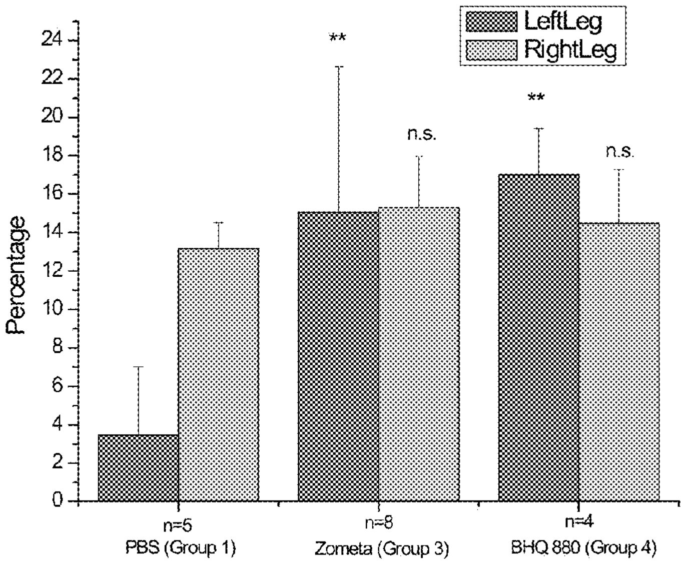
FIG. 13 is a graphic illustration comparing anti-osteolytic efficacy of Zometa with a DKK1/4 antibody.

In FIG. 13, to determine the bone mass, the secondary spongiosa of the tibia is imaged with the Zeiss Imager Z.1 and Axiovision software based on Giemsa stain. The readout is based on the percent calcified bone in the entire field. Every column represents the mean and standard deviation of the stated number of animals. In the PBS, IgG, and anti-DKK1/4 antibody treated groups, only animals with tumor are analyzed. Right legs did not have sham injections and left legs had tumor. Statistic: Dunnett Multiple Comparisons Test One-Way ANOVA. Left legs or right legs compared to the respective leg in the PBS group $p<0.05$*,$p<0.01$**,$p>0.05$ n.s.

Figure 14:
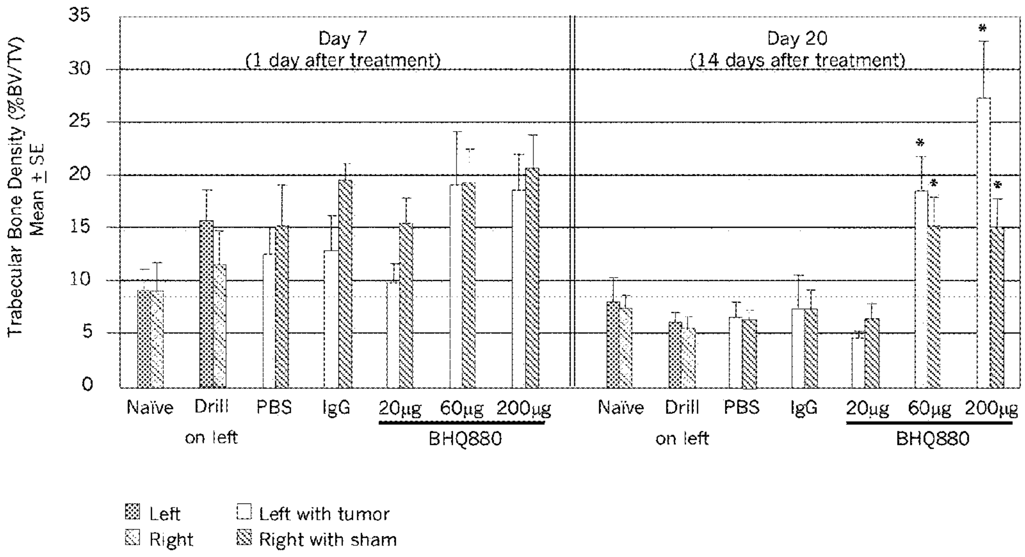
FIG. 14 is a graphic illustration of the dose dependent efficacy of a DKK1/4 antibody on anabolic bone.

FIG. 14 shown an anti-DKK1/4 antibody's anabolic bone efficacy is dose dependent with minimal efficacious dose between 20 and 60 μg/mouse 3x/week. Female nude mice at age of 12 weeks old are implanted intratibially with 2×105 PC-3M2AC6 cells in the left tibia and sham-injection in the right tibia. Treatments started on day 6 post implantation. NVP-anti-DKK1/4 antibody-NX (anti-DKK1/4 antibody) is administered i.v., at doses of 20, 60, and 200 μg/mouse/day, q.d., 3 times a week for 2 weeks. Control IgG is administered i.v., at 200 μg/mouse/day, q.d., 3 times a week for 2 weeks. Vehicle control (PBS) is administered i.v., q.d., 3 times a week for 2 weeks. Animals are scanned at day 7 and 20 post tumor implantation using the μ-CT VivaCT40 Scanner (SCANCO, Switzerland). Trabecular bone density (BV/TV) is analyzed as described in methods. * indicates statistical significant difference from all controls including, vehicle, IgG, drill only, and naïve animals at the same time point at $p<0.05$.

Example 18

Biomarker Status

DKK1 Biomarkers

The RNA expression pattern of DKK1 has been described. Krupnik (1999) showed expression in placenta by Northern Blot analysis, with no expression detected in heart, brain, lung, liver, skeletal muscle or pancreas. Wirths (2003) showed lack of RNA expression in liver, kidney, and breast, although RNA expression is seen in a subset of hepatoblastomas and Wilms' Tumors. Workers examining gastrointestinal tract expression of DKK1 by RNA in situ hybridization showed no expression in stomach and colon, whether normal or malignant (Byun 2006).

RNA expression analysis in mice revealed high DKK1 expression levels in bone, medium expression in fetus and placenta, and weak expression in brown adipose tissue, thymus and duodenum [Li 2006].

DKK1 protein expression is evaluated in myeloma specimens using the same goat antibody employed in the current study (Tian, 2003). In this paper, expression is seen in myeloma cells of patients with low grade morphology; DKK1 protein expression is not detected in the bone marrow biopsy specimens of five control subjects.

Tissue distribution and species crossreactivity of the therapeutic antibody anti-DKK1/4 antibody is studied by screening it against a series of normal human and monkey tissues. Both whole tissue sections and tissue microarrays are evaluated. Positive controls included a commercial antibody for DKK1 that is evaluated in the same tissue set.

DKK1_15 (FITC conjugated anti-DKK1/4 antibody) and DKK1_8 (FITC conjugated Goat anti-DKK1, R&D Systems, # AF1096, lots GBL013101 and GBL14111).

Other Biomarkers

Since little is known about the pathophysiologic role of DKK1, a significant amount of effort is and has been focused on building up the knowledge base about the in vivo effects of anti-DKK1/4 antibody by biomarker studies and how this could be exploited to further the development. Key areas of focus have included 1) Understanding the effect of anti-DKK1/4 antibody in normal and metastatic bone metabolism by the measurement of circulating markers of osteoclastic and osteoblastic activity.

2) Comparative expression levels of DKK1 in multiple myeloma and other tumors to confirm and expand target indications.

3) Effects at a gene expression level in key tissues like colon, bone marrow, lung, skin and breast to assess beta-catenin activation.

Preliminary molecular epidemiology studies have confirmed increased DKK1 serum levels in patients with multiple myeloma and support a POC in this indication.

Based on existing knowledge, Table 18 provides the proposed potential Biomarkers for an anti-DKK1/4 antibody.

TABLE 18

Biomarkers for DKK1 and DKK4 targets

| Categories | Tumor | Blood | Surrogate Tissue |
|---|---|---|---|
| Pharmacodynamic (PD) | N/A | Free and anti-DKK1/4 Ab bound DKK-1 levels | Adipose/ skin |
| Target Downstream Mechanism of Action | | Activation of beta-catenin NTx, CTx, PINP, Osteocalcin, RANKL, OPG, PTH, Vitamin D3, calcitonin | |
| Efficacy | Serum M protein, Urine total M protein, b2 microglobin, LDH | NTx, CTx, PINP, Osteocalcin, RANKL, OPG, PTH, calcitoninBone-ALP, CICP, CTx, NTx, etc | |
| Predictive Markers Stratification Preselection | DKK1 expression | DKK-1, CTx, PINP, Osteocalcin, RANKL, OPG, PTH, Vit D3, calcitonin DKK1 serum levels | |
| Safety | | Immunogenicity | |
| Pharmacokinetic | | anti-DKK1/4 Ab | |

Example 19

Amino Acid Sequences of Heavy and Light Chain Variable Regions of Anti-DKK1 Antibodies The amino acid sequences of the variable regions of the light and heavy chains of anti-DKK1 antibodies, whose CDR regions are shown in Tables 5, 6, 11A and 11B, are provided in full in Table 19.

TABLE 19

Amino Acid Sequences of Heavy and Light Chain Variable Regions of anti-DKK1 Antibodies (SEQ ID NOS: 2-39)

MOR04454 VH: (SEQ ID NO: 2)

QVQLVESGGGLVQPGGSLRLSCAASGFTFSNYGLHWVRQAPGKGLEWVSSISYYGSSTYYADSVKGRFTISRDN
SKNTLYLQMNSLRAEDTAVYYCARDGSHMDKPPGYVFAFWGQGTLVTVSS

MOR04454 VL: (SEQ ID NO: 21)

DIQMTQSPSSLSASVGDRVTITCRASQGIKNYLNWYQQKPGKAPKLLIGAASSLQSGVPSRFSGSGSGTDFTLT
ISSLQPEDFATYYCLQYYGMPPTFGQGTKVEIKRT

MOR04455 VH: (SEQ ID NO: 3)

QVQLVESGGGLVQPGGSLRLSCAASGFTFSSYGMSWVRQAPGKGLEWVSGISGSGSYTYYADSVKGRFTISRDN
SKNTLYLQMNSLRAEDTAVYYCARHYMDHWGQGTLVTVSS

MOR04455 VL: (SEQ ID NO: 22)

DIQMTQSPSSLSASVGDRVTITCRASQDISNYLHWYQQKPGKAPKLLIYGASNLQSGVPSRFSGSGSGTDFTLT
ISSLQPEDFAVYYCQQYDSIPMTFGQGTKVEIKRT

MOR04456 VH: (SEQ ID NO: 4)

QVQLVESGGGLVQPGGSLRLSCAASGFTFNNYGMTWVRQAPGKGLEWVSGISGSGSYTYYADSVKGRFTISRDN
SKNTLYLQMNSLRAEDTAVYYCARTIYMDYWGQGTLVTVSS

TABLE 19-continued

Amino Acid Sequences of Heavy and Light Chain Variable Regions of anti-DKK1 Antibodies (SEQ ID NOS: 2-39)

MOR04456 VL: (SEQ ID NO: 23)

DIVLTQSPATLSLSPGERATLSCRASQNLFSPYLAWYQQKPGQAPRLLIYGASNRATGVPARFSGSGSGTDFTL
TISSLEPEDFATYYCQQYGDEPITFGQGTKVEIKRT

MOR04461 VH: (SEQ ID NO: 5)

QVQLVESGGGLVQPGGSLRLSCAASGFTFSSYWMSWVRQAPGKGLEWVSGISYSGSNTHYADSVKGRFTISRDN
SKNTLYLQMNSLRAEDTAVYYCARMGIDLDYWGQGTLVTVSS

MOR04461 VL: (SEQ ID NO: 24)

DIALTQPASVSGSPGQSITISCTGTSSDVGGFNYVSWYQQHPGKAPKLMIHDGSNRPSGVSNRFSGSKSGNTAS
LTISGLQAEDEADYYCSTWDMTVDFVFGGGTKLTVLGQ

MOR04470 VH: (SEQ ID NO: 6)

QVQLVESGGGLVQPGGSLRLSCAASGFTFSSYWMSWVRQAPGKGLEWVSVISSDSSSTYYADSVKGRFTISRDN
SKNTLYLQMNSLRAEDTAVYYCARHGIDFDHWGQGTLVTVSS

MOR04470 VL: (SEQ ID NO: 25)

DIALTQPASVSGSPGQSITISCTGTSSDLGGYNYVSWYQQHPGKAPKLMIYDVNNRPSGVSNRFSGSKSGNTAS
LTISGLQAEDEADYYCQSYASGNTKVVFGGGTKLTVLGQ

MOR04516 VH: (SEQ ID NO: 7)

QVQLVQSGAEVKKPGESLKISCKGSGYSFTNYYIGWVRQMPGKGLEWMGIIYPTDSYTNYSPSFQGQVTISADK
SISTAYLQWSSLKASDTAMYYCARGIPFRMRGFDYWGQGTLVTVSS

MOR04516 VL: (SEQ ID NO: 26)

DIVLTQPPSVSGAPGQRVTISCSGSSSNIGSSFVNWYQQLPGTAPKLLIGNNSNRPSGVPDRFSGSKSGTSASL
AITGLQSEDEADYYCASFDMGSPNVVFGGGTKLTVLGQ

MOR04907 VH: (SEQ ID NO: 8)

QVQLVESGGGLVQPGGSLRLSCAASGFTFNNYGMTWVRQAPGKGLEWVSGISGSGSYTYYADSVKGRFTISRDN
SKNTLYLQMNSLRAEDTAVYYCARTIYMDYWGQGTLVTVSS

MOR04907 VL: (SEQ ID NO: 27)

DIVLTQSPATLSLSPGERATLSCRASQNLFSPYLAWYQQKPGQAPRLLIYGASNRATGVPARFSGSGSGTDFTL
TISSLEPEDFAVYYCQQYLSLPTTFGQGTKVEIKRT

MOR04913 VH: (SEQ ID NO: 9)

QVQLVESGGGLVQPGGSLRLSCAASGFTFNNYGMTWVRQAPGKGLEWVSGISGSGSYTYYADSVKGRFTISRDN
SKNTLYLQMNSLRAEDTAVYYCARTIYMDYWGQGTLVTVSS

MOR04913 VL: (SEQ ID NO: 28)

DIVLTQSPATLSLSPGERATLSCRASQNLFSPYLAWYQQKPGQAPRLLIYGASNRATGVPARFSGSGSGTDFTL
TISSLEPEDFAVYYCQQYMTLPLTFGQGTKVEINRT

MOR04946 VH: (SEQ ID NO: 10)

QVQLVESGGGLVQPGGSLRLSCAASGFTFNNYGMTWVRQAPGKGLEWVSGISGSGSYTYYADSVKGRFTISRDN
SKNTLYLQMNSLRAEDTAVYYCARTIYMDYWGQGTLVTVSS

MOR04946 VL: (SEQ ID NO: 29)

DIVLTQSPATLSLSPGERATLSCRASQNLFSPYLAWYQQKPGQAPRLLIYGASNRATGVPARFSGSGSGTDFTL
TISSLEPEDFAVYYCQQYLTLPLTFGQGTKVEIKRT

MOR04910 VH: (SEQ ID NO: 11)

QVQLVESGGGLVQPGGSLRLSCAASGFTFSSYWMSWVRQAPGKGLEWVSGISYSGSNTHYADSVKGRFTISRDN
SKNTLYLQMNSLRAEDTAVYYCARMGIDLDYWGQGTLVTVSS

MOR04910 VL: (SEQ ID NO: 30)

DIALTQPASVSGSPGQSITISCTGTSSDVGGFNYVSWYQQHPGKAPKLMIHDGSNRPSGVSNRFSGSKSGNTAS
LTISGLQAEDEADYYCQSWDVSPITAVFGGGTKLTVLGQ

TABLE 19-continued

Amino Acid Sequences of Heavy and Light Chain Variable Regions of anti-DKK1 Antibodies (SEQ ID NOS: 2-39)

| MOR04921 VH: | (SEQ ID NO: 12) |
|---|---|
| QVQLVESGGGLVQPGGSLRLSCAASGFTFSSYWMSWVRQAPGKGLEWVSGISYSGSNTHYADSVKGRFTISRDN SKNTLYLQMNSLRAEDTAVYYCARMGIDLDYWGQGTLVTVSS | |
| MOR04921 VL: | (SEQ ID NO: 31) |
| DIALTQPASVSGSPGQSITISCTGTSSDVGGFNYVSWYQQHPGKAPKLMIHDGSNRPSGVSNRFSGSKSGNTAS LTISGLQAEDEADYYCQTWATSPLSSVFGGGTKLTVLGQ | |
| MOR04948 VH: | (SEQ ID NO: 13) |
| QVQLVESGGGLVQPGGSLRLSCAASGFTFSSYWMSWVRQAPGKGLEWVSGISYSGSNTHYADSVKGRFTISRDN SKNTLYLQMNSLRAEDTAVYYCARMGIDLDYWGQGTLVTVSS | |
| MOR04948 VL: | (SEQ ID NO: 32) |
| DIALTQPASVSGSPGQSITISCTGTSSDVGGFNYVSWYQQHPGKAPKLMIHDGSNRPSGVSNRFSGSKSGNTAS LTISGLQAEDEADYYCQTWDSLSFFVFGGGTKLTVLGQ | |
| MOR04914 VH: | (SEQ ID NO: 14) |
| QVQLVESGGGLVQPGGSLRLSCAASGFTFSSYWMSWVRQAPGKGLEWVSVISSDSSSTYYADSVKGRFTISRDN SKNTLYLQMNSLRAEDTAVYYCARHGIDFDHWGQGTLVTVSS | |
| MOR04914 VL: | (SEQ ID NO: 33) |
| DIALTQPASVSGSPGQSITISCTGTSSDLGGYNYVSWYQQHPGKAPKLMIYDVNNRPSGVSNRFSGSKSGNTAS LTISGLQAEDEADYYCQSYTYTPISPVFGGGTKLTVLGQ | |
| MOR04920 VH: | (SEQ ID NO: 15) |
| QVQLVESGGGLVQPGGSLRLSCAASGFTFSSYWMSWVRQAPGKGLEWVSSIEHKDAGYTTWYAAGVKGRFTISR DNSKNTLYLQMNSLRAEDTAVYYCARHGIDFDHWGQGTLVTVSS | |
| MOR04920 VL: | (SEQ ID NO: 34) |
| DIALTQPASVSGSPGQSITISCTGTSSDLGGYNYVSWYQQHPGKAPKLMIYDVNNRPSGVSNRFSGSKSGNTAS LTISGLQAEDEADYYCQSYASGNTKVVFGGGTKLTVLGQ | |
| MOR04945 VH: | (SEQ ID NO: 16) |
| QVQLVESGGGLVQPGGSLRLSCAASGFTFSSYWMSWVRQAPGKGLEWVSVISSDSSSTYYADSVKGRFTISRDN SKNTLYLQMNSLRAEDTAVYYCARHGIDFDHWGQGTLVTVSS | |
| MOR04945 VL: | (SEQ ID NO: 35) |
| DIALTQPASVSGSPGQSITISCTGTSSDLGGYNYVSWYQQHPGKAPKLMIYDVNNRPSGVSNRFSGSKSGNTAS LTISGLQAEDEADYYCQTYDQIKLSAVFGGGTKLTVLGQ | |
| MOR04952 VH: | (SEQ ID NO: 17) |
| QVQLVESGGGLVQPGGSLRLSCAASGFTFSSYWMSWVRQAPGKGLEWVSVISSDSSSTYYADSVKGRFTISRDN SKNTLYLQMNSLRAEDTAVYYCARHGIDFDHWGQGTLVTVSS | |
| MOR04952 VL: | (SEQ ID NO: 36) |
| DIALTQPASVSGSPGQSITISCTGTSSDLGGYNYVSWYQQHPGKAPKLMIYDVNNRPSGVSNRFSGSKSGNTAS LTISGLQAEDEADYYCQSYDSPTDSVVFGGGTKLTVLGQ | |
| MOR04954 VH: | (SEQ ID NO: 18) |
| QVQLVESGGGLVQPGGSLRLSCAASGFTFSSYWMSWVRQAPGKGLEWVSVIEHKDKGGTTYYAASVKGRFTISR DNSKNTLYLQMNSLRAEDTAVYYCARHGIDFDHWGQGTLVTVSS | |
| MOR04954 VL: | (SEQ ID NO: 37) |
| DIALTQPASVSGSPGQSITISCTGTSSDLGGYNYVSWYQQHPGKAPKLMIYDVNNRPSGVSNRFSGSKSGNTAS LTISGLQAEDEADYYCQSYASGNTKVVFGGGTKLTVLGQ | |
| MOR04947 VH: | (SEQ ID NO: 19) |
| QVQLVQSGAEVKKPGESLKISCKGSGYSFTNYYIGWVRQMPGKGLEWMGIIVPGTSYTIYSPSFQGQVTISADK SISTAYLQWSSLKASDTAMYYCARGIPFRMRGFDYWGQGTLVTVSS | |

TABLE 19-continued

| Amino Acid Sequences of Heavy and Light Chain Variable Regions of anti-DKK1 Antibodies (SEQ ID NOS: 2-39) | |
|---|---|
| MOR04947 VL: | (SEQ ID NO: 38) |
| DIVLTQPPSVSGAPGQRVTISCSGSSSNIGSSFVNWYQQLPGTAPKLLIGNNSNRPSGVPDRFSGSKSGTSASL AITGLQSEDEADYYCASFDMGSPNVVFGGGTKLTVLGQ | |
| MOR05145 VH: | (SEQ ID NO: 20) |
| QVQLVESGGGLVQPGGSLRLSCAASGFTFNNYGMTWVRQAPGKGLEWVSGISGSGSYTYYADSVKGRFTISRDN SKNTLYLQMNSLRAEDTAVYYCARTIYMDYWGQGTLVTVSS | |
| MOR05145 VL: | (SEQ ID NO: 39) |
| DIVLTQSPATLSLSPGERATLSCRASQNLFSPYLAWYQQKPGQAPRLLIYGASNRATGVPARFSGSGSGTDFTL TISSLEPEDFAVYYCQQYMTLPLTFGQGTKVEIKRT | |

The CDR and FR sections of the variable regions in Table 19 are aligned in Table 20A for heavy chains (SEQ ID NOS: 2-20; VH3 is SEQ ID NO:125, VH5 is SEQ ID NO:126), Table 20B for kappa light chains (SEQ ID NOS: 21, 22, 23, 27, 28 and 29; VK1 is SEQ ID NO:127 and VK3 is SEQ ID NO:128), and in Table 20C for lambda light chains (SEQ ID NOS: 24, 25, 30, 31, 32, 33, 34, 35, 36 and 37; VL2 is SEQ ID NO:129 and VL1 is SEQ ID NO:130).

TABLE 20A

Alignment of the Amino Acid Sequences of Heavy Chain Variable Regions of anti-DKK1 Antibodies (SEQ ID NOs: 2-20, 125-126)

| VH | | VH sequences DKK1 binders | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| | | Framework 1 | | | | | | | | | | | | | | | | | | | | | | | | CDR 1 | | | | | | | | | | | |
| Position | | | | | | | | | | | 1 | | | | | | | | | | 2 | | | | | | | | | | 3 | | | | | | | |
| | | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | a | b | 2 | 3 | 4 | 5 |
| | | | | MfeI | | | | | | | | | | | | | | | | | | | | | | BspEI | | | | | | | | | | | | |
| SEQ ID NO 1 | VH3 | Q | V | Q | L | V | E | S | G | G | G | L | V | Q | P | G | G | S | L | R | L | S | C | A | A | S | G | F | T | F | S | S | - | - | Y | A | M | S |
| SEQ ID NO 2 | 4454 | Q | V | Q | L | V | E | S | G | G | G | L | V | Q | P | G | G | S | L | R | L | S | C | A | A | S | G | F | T | F | S | N | - | - | Y | G | L | H |
| SEQ ID NO 3 | 4455 | Q | V | Q | L | V | E | S | G | G | G | L | V | Q | P | G | G | S | L | R | L | S | C | A | A | S | G | F | T | F | S | S | - | - | Y | G | M | S |
| SEQ ID NO 4 | 4456 | Q | V | Q | L | V | E | S | G | G | G | L | V | Q | P | G | G | S | L | R | L | S | C | A | A | S | G | F | T | F | N | N | - | - | Y | G | M | T |
| SEQ ID NO 5 | 4907 | Q | V | Q | L | V | E | S | G | G | G | L | V | Q | P | G | G | S | L | R | L | S | C | A | A | S | G | F | T | F | N | N | - | - | Y | G | M | T |
| SEQ ID NO 6 | 4913 | Q | V | Q | L | V | E | S | G | G | G | L | V | Q | P | G | G | S | L | R | L | S | C | A | A | S | G | F | T | F | N | N | - | - | Y | G | M | T |
| SEQ ID NO 7 | 4946 | Q | V | Q | L | V | E | S | G | G | G | L | V | Q | P | G | G | S | L | R | L | S | C | A | A | S | G | F | T | F | N | N | - | - | Y | G | M | T |
| SEQ ID NO 8 | 5145 | Q | V | Q | L | V | E | S | G | G | G | L | V | Q | P | G | G | S | L | R | L | S | C | A | A | S | G | F | T | F | N | N | - | - | Y | G | M | T |
| SEQ ID NO 9 | 4461 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 10 | 4910 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 11 | 4921 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 12 | 4948 | Q | V | Q | L | V | E | S | G | G | G | L | V | Q | P | G | G | S | L | R | L | S | C | A | A | S | G | F | T | T | S | S | - | - | Y | W | M | S |
| SEQ ID NO 13 | 4470 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 14 | 4914 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 15 | 4920 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 16 | 4945 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 17 | 4952 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 18 | 4954 | Q | V | Q | L | V | E | S | G | G | G | L | V | Q | P | G | G | S | L | R | L | S | C | A | A | S | G | F | T | F | S | S | - | - | Y | W | M | S |
| SEQ ID NO 19 | VH5 | Q | V | Q | L | V | Q | S | G | A | E | V | K | K | P | G | E | S | L | K | I | L | C | K | G | S | G | Y | S | F | T | S | - | - | Y | W | I | G |
| SEQ ID NO 20 | 4516 | Q | V | Q | L | V | Q | S | G | A | E | V | K | K | P | G | E | S | L | K | I | S | C | K | G | S | G | Y | S | F | T | N | - | - | Y | Y | I | G |
| SEQ ID NO 21 | 4947 | Q | V | Q | L | V | Q | S | G | A | E | V | K | K | P | G | E | S | L | K | I | S | C | K | G | S | G | Y | S | F | T | N | - | - | Y | Y | I | G |

TABLE 20A-continued

Alignment of the Amino Acid Sequences of Heavy Chain Variable Regions of anti-DKK1 Antibodies
(SEQ ID NOs: 2-20, 125-126)

| | Framework 2 | | | | | | | | | | | | | | CDR 2 | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | | | | 4 | | | | | | | | | | | 5 | | | | | | | | | | | | | | 6 | | | | |
| | 6 | 7 | 8 | 9 | 0 | 1 | 2 | 3 | 4 | 5 | 6 | 7 | 8 | 9 | 0 | 1 | 2 | a | b | c | 3 | 4 | 5 | 6 | 7 | 8 | 9 | 0 | 1 | 2 | 3 | 4 | 5 |
| | | | | | BstXI | | | | | XhoI | | | | | | | | | | | | | | | | | | | | | | | |
| SEQ ID NO 1 | W | V | R | Q | A | P | G | K | G | L | E | W | V | S | A | I | S | G | - | - | S | G | G | S | T | Y | Y | A | D | S | V | K | G |
| SEQ ID NO 2 | W | V | R | Q | A | P | G | K | G | L | E | W | V | S | S | I | S | Y | - | - | Y | G | S | S | T | Y | Y | A | D | S | V | K | G |
| SEQ ID NO 3 | W | V | R | Q | A | P | G | K | G | L | E | W | V | S | G | I | S | G | - | - | S | G | S | Y | T | Y | Y | A | D | S | V | K | G |
| SEQ ID NO 4 | W | V | R | Q | A | P | G | K | G | L | E | W | V | S | G | I | S | G | - | - | S | G | S | Y | T | Y | Y | A | D | S | V | K | G |
| SEQ ID NO 5 | W | V | R | Q | A | P | G | K | G | L | E | W | V | S | G | I | S | G | - | - | S | G | S | Y | T | Y | Y | A | D | S | V | K | G |
| SEQ ID NO 6 | W | V | R | Q | A | P | G | K | G | L | E | W | V | S | G | I | S | G | - | - | S | G | S | Y | T | Y | Y | A | D | S | V | K | G |
| SEQ ID NO 7 | W | V | R | Q | A | P | G | K | G | L | E | W | V | S | G | I | S | G | - | - | S | G | S | Y | T | Y | Y | A | D | S | V | K | G |
| SEQ ID NO 8 | W | V | R | Q | A | P | G | K | G | L | E | W | V | S | G | I | S | G | - | - | S | G | S | Y | T | Y | Y | A | D | S | V | K | G |
| SEQ ID NO 9 | W | V | R | Q | A | P | G | K | G | L | E | W | V | S | G | I | S | Y | - | - | S | G | S | N | T | H | Y | A | D | S | V | K | G |
| SEQ ID NO 10 | W | V | R | Q | A | P | G | K | G | L | E | W | V | S | G | I | S | Y | - | - | S | G | S | N | T | H | Y | A | D | S | V | K | G |
| SEQ ID NO 11 | W | V | R | Q | A | P | G | K | G | L | E | W | V | S | G | I | S | Y | - | - | S | G | S | N | T | H | Y | A | D | S | V | K | G |
| SEQ ID NO 12 | W | V | R | Q | A | P | G | K | G | L | E | W | V | S | G | I | S | Y | - | - | S | G | S | N | T | H | Y | A | D | S | V | K | G |
| SEQ ID NO 13 | W | V | R | Q | A | P | G | K | G | L | E | W | V | S | V | I | S | S | - | - | D | S | S | S | T | Y | Y | A | D | S | V | K | G |
| SEQ ID NO 14 | W | V | R | Q | A | P | G | K | G | L | E | W | V | S | V | I | S | S | - | - | D | S | S | S | T | Y | Y | A | D | S | V | K | G |
| SEQ ID NO 15 | W | V | R | Q | A | P | G | K | G | L | E | W | V | S | S | I | E | H | K | D | A | G | Y | T | T | W | Y | A | A | G | V | K | G |
| SEQ ID NO 16 | W | V | R | Q | A | P | G | K | G | L | E | W | V | S | V | I | S | S | - | - | D | S | S | S | T | Y | Y | A | D | S | V | K | G |
| SEQ ID NO 17 | W | V | R | Q | A | P | G | K | G | L | E | W | V | S | V | I | S | S | - | - | D | S | S | S | T | Y | Y | A | D | S | V | K | G |
| SEQ ID NO 18 | W | V | R | Q | A | P | G | K | G | L | E | W | V | S | V | I | E | H | K | D | K | G | G | T | T | Y | Y | A | A | S | V | K | G |
| SEQ ID NO 19 | W | V | R | Q | M | P | G | K | G | L | E | W | M | G | I | I | Y | P | - | - | G | D | S | D | T | R | Y | S | P | S | F | Q | G |
| SEQ ID NO 20 | W | V | R | Q | M | P | G | K | G | L | E | W | M | G | I | I | Y | P | - | - | G | D | S | D | T | R | Y | S | P | S | F | Q | G |
| SEQ ID NO 21 | W | V | R | Q | M | P | G | K | G | L | E | W | M | G | I | I | B | P | - | - | G | T | S | Y | T | I | Y | S | P | S | F | Q | G |

| | Framework 3 | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | | | 7 | | | | | | | | | | 8 | | | | | | | | | | | | | 9 | | | | |
| | 6 | 7 | 8 | 9 | 0 | 1 | 2 | 3 | 4 | 5 | 6 | 7 | 8 | 9 | 0 | 1 | 2 | a | b | c | 3 | 4 | 5 | 6 | 7 | 8 | 9 | 0 | 1 | 2 | 3 | 4 |
| | | | | | | | | | BstBI | | | | | | | | | | | | | | | | EagI | | | | | BssHII | | |
| SEQ ID NO 1 | R | F | T | I | S | R | D | N | S | K | N | T | L | Y | L | Q | M | N | S | L | R | A | E | D | T | A | V | Y | Y | C | A | R |
| SEQ ID NO 2 | R | F | T | I | S | R | D | N | S | K | N | T | L | Y | L | Q | M | N | S | L | R | A | E | D | T | A | V | Y | Y | C | A | R |
| SEQ ID NO 3 | R | F | T | I | S | R | D | N | S | K | N | T | L | Y | L | Q | M | N | S | L | R | A | E | D | T | A | V | Y | Y | C | A | R |
| SEQ ID NO 4 | R | F | T | I | S | R | D | N | S | K | N | T | L | Y | L | Q | M | N | S | L | R | A | E | D | T | A | V | Y | Y | C | A | R |
| SEQ ID NO 5 | R | F | T | I | S | R | D | N | S | K | N | T | L | Y | L | Q | M | N | S | L | R | A | E | D | T | A | V | Y | Y | C | A | R |
| SEQ ID NO 6 | R | F | T | I | S | R | D | N | S | K | N | T | L | Y | L | Q | M | N | S | L | R | A | E | D | T | A | V | Y | Y | C | A | R |
| SEQ ID NO 7 | R | F | T | I | S | R | D | N | S | K | N | T | L | Y | L | Q | M | N | S | L | R | A | E | D | T | A | V | Y | Y | C | A | R |
| SEQ ID NO 8 | R | F | T | I | S | R | D | N | S | K | N | T | L | Y | L | Q | M | N | S | L | R | A | E | D | T | A | V | Y | Y | C | A | R |
| SEQ ID NO 9 | R | F | T | I | S | R | D | N | S | K | N | T | L | Y | L | Q | M | N | S | L | R | A | E | D | T | A | V | Y | Y | C | A | R |
| SEQ ID NO 10 | R | F | T | I | S | R | D | N | S | K | N | T | L | Y | L | Q | M | N | S | L | R | A | E | D | T | A | V | Y | Y | C | A | R |
| SEQ ID NO 11 | R | F | T | I | S | R | D | N | S | K | N | T | L | Y | L | Q | M | N | S | L | R | A | E | D | T | A | V | Y | Y | C | A | R |
| SEQ ID NO 12 | R | F | T | I | S | R | D | N | S | K | N | T | L | Y | L | Q | M | N | S | L | R | A | E | D | T | A | V | Y | Y | C | A | R |
| SEQ ID NO 13 | R | F | T | I | S | R | D | N | S | K | N | T | L | Y | L | Q | M | N | S | L | R | A | E | D | T | A | V | Y | Y | C | A | R |
| SEQ ID NO 14 | R | F | T | I | S | R | D | N | S | K | N | T | L | Y | L | Q | M | N | S | L | R | A | E | D | T | A | V | Y | Y | C | A | R |
| SEQ ID NO 15 | R | F | T | I | S | R | D | N | S | K | N | T | L | Y | L | Q | M | N | S | L | R | A | E | D | T | A | V | Y | Y | C | A | R |
| SEQ ID NO 16 | R | F | T | I | S | R | D | N | S | K | N | T | L | Y | L | Q | M | N | S | L | R | A | E | D | T | A | V | Y | Y | C | A | R |
| SEQ ID NO 17 | R | F | T | I | S | R | D | N | S | K | N | T | L | Y | L | Q | M | N | S | L | R | A | E | D | T | A | V | Y | Y | C | A | R |
| SEQ ID NO 18 | R | F | T | I | S | R | D | N | S | K | N | T | L | Y | L | Q | M | N | S | L | R | A | E | D | T | A | V | Y | Y | C | A | R |
| | | BstEII | | | | | | | | | | | | | | | | | | | | | | | | | | | | | | |
| SEQ ID NO 19 | Q | V | T | I | S | A | D | K | S | I | S | T | A | Y | L | Q | W | S | S | L | K | A | S | D | T | A | M | Y | Y | C | A | R |
| SEQ ID NO 20 | Q | V | T | I | S | A | D | K | S | I | S | T | A | Y | L | Q | W | S | S | L | K | A | S | D | T | A | M | Y | Y | C | A | R |
| SEQ ID NO 21 | Q | V | T | I | S | A | D | K | S | I | S | T | A | Y | L | Q | W | S | S | L | K | A | S | D | T | A | M | Y | Y | C | A | R |

TABLE 20A-continued

Alignment of the Amino Acid Sequences of Heavy Chain Variable Regions of anti-DKK1 Antibodies
(SEQ ID NOs: 2-20, 125-126)

| | CDR 3 | | | | | | | | | | | | | | | | | | Framework 4 | | | | | | | | | | |
|---|---|---|---|---|---|---|---|---|---|---|---|---|---|---|---|---|---|---|---|---|---|---|---|---|---|---|---|---|---|
| | | | | | | 10 | | | | | | | | | | | | | | | | | | | | 11 | | | |
| | 5 | 6 | 7 | 8 | 9 | 0 | a | b | c | d | e | f | g | h | i | j | 1 | 2 | 3 | 4 | 5 | 6 | 7 | 8 | 9 | 0 | 1 | 2 | 3 |
| | | | | | | | | | | | | | | | | | | | | | StyI | | | | | | | BlpI | |
| SEQ ID NO 1 | X | X | X | X | X | X | X | X | X | X | X | X | X | X | X | X | X | X | W | G | Q | G | T | L | V | T | V | S | S |
| SEQ ID NO 2 | D | G | S | H | M | D | K | P | P | G | Y | V | - | - | - | F | A | F | W | G | Q | G | T | L | V | T | V | S | S |
| SEQ ID NO 3 | H | Y | - | - | - | - | - | - | - | - | - | - | - | - | - | M | D | H | W | G | Q | G | T | L | V | T | V | S | S |
| SEQ ID NO 4 | T | I | Y | - | - | - | - | - | - | - | - | - | - | - | - | M | D | Y | W | G | Q | G | T | L | V | T | V | S | S |
| SEQ ID NO 5 | T | I | Y | - | - | - | - | - | - | - | - | - | - | - | - | M | D | Y | W | G | Q | G | T | L | V | T | V | S | S |
| SEQ ID NO 6 | T | I | Y | - | - | - | - | - | - | - | - | - | - | - | - | M | D | Y | W | G | Q | G | T | L | V | T | V | S | S |
| SEQ ID NO 7 | T | I | Y | - | - | - | - | - | - | - | - | - | - | - | - | M | D | Y | W | G | Q | G | T | L | V | T | V | S | S |
| SEQ ID NO 8 | T | I | Y | - | - | - | - | - | - | - | - | - | - | - | - | M | D | Y | W | G | Q | G | T | L | V | T | V | S | S |
| SEQ ID NO 9 | M | G | I | D | - | - | - | - | - | - | - | - | - | - | - | L | D | Y | W | G | Q | G | T | L | V | T | V | S | S |
| SEQ ID NO 10 | M | G | I | D | - | - | - | - | - | - | - | - | - | - | - | L | D | Y | W | G | Q | G | T | L | V | T | V | S | S |
| SEQ ID NO 11 | M | G | I | D | - | - | - | - | - | - | - | - | - | - | - | L | D | Y | W | G | Q | G | T | L | V | T | V | S | S |
| SEQ ID NO 12 | M | G | I | D | - | - | - | - | - | - | - | - | - | - | - | L | D | Y | W | G | Q | G | T | L | V | T | V | S | S |
| SEQ ID NO 13 | H | G | I | D | - | - | - | - | - | - | - | - | - | - | - | F | D | H | W | G | Q | G | T | L | V | T | V | S | S |
| SEQ ID NO 14 | H | G | I | D | - | - | - | - | - | - | - | - | - | - | - | F | D | H | W | G | Q | G | T | L | V | T | V | S | S |
| SEQ ID NO 15 | H | G | I | D | - | - | - | - | - | - | - | - | - | - | - | F | D | H | W | G | Q | G | T | L | V | T | V | S | S |
| SEQ ID NO 16 | H | G | I | D | - | - | - | - | - | - | - | - | - | - | - | F | D | H | W | G | Q | G | T | L | V | T | V | S | S |
| SEQ ID NO 17 | H | G | I | D | - | - | - | - | - | - | - | - | - | - | - | F | D | H | W | G | Q | G | T | L | V | T | V | S | S |
| SEQ ID NO 18 | H | G | I | D | - | - | - | - | - | - | - | - | - | - | - | F | D | H | W | G | Q | G | T | L | V | T | V | S | S |
| SEQ ID NO 19 | X | X | X | X | X | X | X | X | X | X | X | X | X | X | X | X | X | X | W | G | Q | G | T | L | V | T | V | S | S |
| SEQ ID NO 20 | G | I | P | F | R | M | R | G | - | - | - | - | - | - | - | F | D | Y | W | G | Q | G | T | L | V | T | V | S | S |
| SEQ ID NO 21 | G | I | P | F | R | M | R | G | - | - | - | - | - | - | - | F | D | Y | W | G | Q | G | T | L | V | T | V | S | S |

TABLE 20B

Alignment of the Amino Acid Sequences of Kappa Light Chain Variable Regions of anti-DKK1 Antibodies
(SEQ ID NOs: 24-25, 30-37, 129-130)

| | VL | VL kappa sequences DKK1 binders | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | Framework 1 | | | | | | | | | | | | | | | | | | | | | | | CDR 1 | | | | | | | | | | | | | | | | |
| | Position | | | | | | | | | | 1 | | | | | | | | | | 2 | | | | | | | | | | 3 | | | | | | | | | | |
| | | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | a | b | c | d | e | f | 1 | 2 | 3 | 4 |
| | | EcoRV | | | | BanII | | | | | | | | | | | | | | | | | | | | PstI | | | | | | | | | | | | | | | |
| SEQ ID NO 22 | VK1 | D | I | Q | M | T | Q | S | P | S | S | L | S | A | S | V | G | D | R | V | T | I | T | C | R | A | S | Q | G | I | S | - | - | - | - | - | - | S | Y | L | A |
| SEQ ID NO 23 | 4454 | D | I | Q | M | T | Q | S | P | S | S | L | S | A | S | V | G | D | R | V | T | I | T | C | R | A | S | Q | G | I | K | - | - | - | - | - | - | N | Y | L | N |
| SEQ ID NO 24 | 4455 | D | I | Q | M | T | Q | S | P | S | S | L | S | A | S | V | G | D | R | V | T | I | T | C | R | A | S | Q | D | I | S | - | - | - | - | - | - | N | Y | L | H |
| SEQ ID NO 25 | VK3 | D | I | V | L | T | Q | S | P | A | T | L | S | L | S | P | G | E | R | A | T | L | S | C | R | A | S | Q | S | V | S | S | - | - | - | - | - | S | Y | L | A |
| SEQ ID NO 26 | 4456 | D | I | V | L | T | Q | S | P | A | T | L | S | L | S | P | G | E | R | A | T | L | S | C | R | A | S | Q | N | L | F | S | - | - | - | - | | P | Y | L | A |
| SEQ ID NO 27 | 4907 | D | I | V | L | T | Q | S | P | A | T | L | S | L | S | P | G | E | R | A | T | L | S | C | R | A | S | Q | N | L | F | S | - | - | - | - | - | P | Y | L | A |
| SEQ ID NO 28 | 4913 | D | I | V | L | T | Q | S | P | A | T | L | S | L | S | P | G | E | R | A | T | L | S | C | R | A | S | Q | N | L | F | S | - | - | - | - | - | P | Y | L | A |
| SEQ ID NO 29 | 4946 | D | I | V | L | T | Q | S | P | A | T | L | S | L | S | P | G | E | R | A | T | L | S | C | R | A | S | Q | N | L | F | S | - | - | - | - | - | P | Y | L | A |
| SEQ ID NO 30 | 5145 | D | I | V | L | T | Q | S | P | A | T | L | S | L | S | P | G | E | R | A | T | L | S | C | R | A | S | Q | N | L | F | S | - | - | - | - | - | P | Y | L | A |

TABLE 20B-continued

Alignment of the Amino Acid Sequences of Kappa Light Chain Variable Regions of anti-DKK1 Antibodies (SEQ ID NOs: 24-25, 30-37, 129-130)

| | Framework 2 | | | | | | | | | | | | | | | CDR 2 | | | | | | |
|---|---|---|---|---|---|---|---|---|---|---|---|---|---|---|---|---|---|---|---|---|---|---|
| | | | | | | 4 | | | | | | | | | | 5 | | | | | | |
| | 5 | 6 | 7 | 8 | 9 | 0 | 1 | 2 | 3 | 4 | 5 | 6 | 7 | 8 | 9 | 0 | 1 | 2 | 3 | 4 | 5 | 6 |
| | | | | | KpnI | | | | | SexAI | | | | | | AseI | | | | | | |
| SEQ ID NO 22 | W | Y | Q | Q | K | P | G | K | A | P | K | L | L | I | Y | A | A | S | S | L | Q | S |
| SEQ ID NO 23 | W | Y | Q | Q | K | P | G | K | A | P | K | L | L | I | G | A | A | S | S | L | Q | S |
| SEQ ID NO 24 | W | Y | Q | Q | K | P | G | K | A | P | K | L | L | I | Y | G | A | S | N | L | Q | S |
| SEQ ID NO 25 | W | Y | Q | Q | K | P | G | Q | A | P | R | L | L | I | Y | G | A | S | S | R | A | T |
| SEQ ID NO 26 | W | Y | Q | Q | K | P | G | Q | A | P | R | L | L | I | Y | G | A | S | N | R | A | T |
| SEQ ID NO 27 | W | Y | Q | Q | K | P | G | Q | A | P | R | L | L | I | Y | G | A | S | N | R | A | T |
| SEQ ID NO 28 | W | Y | Q | Q | K | P | G | Q | A | P | R | L | L | I | Y | G | A | S | N | R | A | T |
| SEQ ID NO 29 | W | Y | Q | Q | K | P | G | Q | A | P | R | L | L | I | Y | G | A | S | N | R | A | T |
| SEQ ID NO 30 | W | Y | Q | Q | K | P | G | Q | A | P | R | L | L | I | Y | G | A | S | N | R | A | T |

| | Framework 3 | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | | 6 | | | | | | | | | | 7 | | | | | | | | | | 8 | | | | | | | | |
| | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 |
| | SanDI | | | | | | | BamHI | | | | | | | | | | | | | | | | | BbsI | | | | | | | |
| SEQ ID NO 22 | G | V | P | S | R | F | S | G | S | G | S | G | T | D | F | T | L | T | I | S | S | L | Q | P | E | D | F | A | TN | Y | Y | C |
| SEQ ID NO 23 | G | V | P | S | R | F | S | G | S | G | S | G | T | D | F | T | L | T | I | S | S | L | Q | P | E | D | F | A | T | Y | Y | C |
| SEQ ID NO 24 | G | V | P | S | R | F | S | G | S | G | S | G | T | D | F | T | L | T | I | S | S | L | Q | P | E | D | F | A | V | Y | Y | C |
| SEQ ID NO 25 | G | V | P | A | R | F | S | G | S | G | S | G | T | D | F | T | L | T | I | S | S | L | E | P | E | D | F | A | TN | Y | Y | C |
| SEQ ID NO 26 | G | V | P | A | R | F | S | G | S | G | S | G | T | D | F | T | L | T | I | S | S | L | E | P | E | D | F | A | T | Y | Y | C |
| SEQ ID NO 27 | G | V | P | A | R | F | S | G | S | G | S | G | T | D | F | T | L | T | I | S | S | L | E | P | E | D | F | A | T | Y | Y | C |
| SEQ ID NO 28 | G | V | P | A | R | F | S | G | S | G | S | G | T | D | F | T | L | T | I | S | S | L | E | P | E | D | F | A | T | Y | Y | C |
| SEQ ID NO 29 | G | V | P | A | R | F | S | G | S | G | S | G | T | D | F | T | L | T | I | S | S | L | E | P | E | D | F | A | T | Y | Y | C |
| SEQ ID NO 30 | G | V | P | A | R | F | S | G | S | G | S | G | T | D | F | T | L | T | I | S | S | L | E | P | E | D | F | A | T | Y | Y | C |

| | CDR 3 | | | | | | | | | | Framework 4 | | | | | | | | | | | | |
|---|---|---|---|---|---|---|---|---|---|---|---|---|---|---|---|---|---|---|---|---|---|---|---|
| | | 9 | | | | | | | | | | | | 10 | | | | | | | | | |
| | 9 | 0 | 1 | 2 | 3 | 4 | 5 | A | B | 6 | 7 | 8 | 9 | 0 | 1 | 2 | 3 | 4 | 5 | 6 | 7 | 8 | 9 |
| | | | | | | | | | | | | | MscI | | | | | | | | | BslWI | |
| SEQ ID NO 22 | X | X | X | X | X | X | X | - | - | X | T | F | G | Q | G | T | K | V | E | I | K | R | T |
| SEQ ID NO 23 | L | Q | Y | Y | G | M | P | - | - | P | T | F | G | Q | G | T | K | V | E | I | K | R | T |
| SEQ ID NO 24 | Q | Q | Y | D | S | I | P | - | - | M | T | F | G | Q | G | T | K | V | E | I | K | R | T |
| SEQ ID NO 25 | X | X | X | X | X | X | X | - | - | X | T | F | G | Q | G | T | K | V | E | I | K | R | T |
| SEQ ID NO 26 | Q | Q | Y | G | D | E | P | - | - | I | T | F | G | Q | G | T | K | V | E | I | K | R | T |
| SEQ ID NO 27 | Q | Q | Y | L | S | L | P | - | - | T | T | F | G | Q | G | T | K | V | E | I | K | R | T |
| SEQ ID NO 28 | Q | Q | Y | M | T | L | P | - | - | L | T | F | G | Q | G | T | K | V | E | I | N | R | T |
| SEQ ID NO 29 | Q | Q | Y | L | T | L | P | - | - | L | T | F | G | Q | G | T | K | V | E | I | K | R | T |
| SEQ ID NO 30 | Q | Q | Y | M | T | L | P | - | - | L | T | F | G | Q | G | T | K | V | E | I | K | R | T |

TABLE 20C

Alignment of the Amino Acid Sequences of Lambda Light Chain Variable Regions of anti-DKK1 Antibodies (SEQ ID NOs:)

VL — VL lambda sequences DKK1 binders

| Position | | Framework 1 (1 2 / 3 4 5 6 7 8 9 10 1 2 3 4) | (5 6) | (7 8 9 20 1) | (2 3) | CDR 1 (4 5 6 7 8 9 30 a b c d e f 1 2 3 4) |
|---|---|---|---|---|---|---|
| | | EcoRV | SexA | | BssSI | |
| SEQ ID NO 31 | V12 | D I / A L T Q P A - S V S G S | P G | Q S I T I | S C | T G T S S D V G G Y - - - N Y V S |
| SEQ ID NO 32 | 4461 | D I / A L T Q P A - S V S G S | P G | Q S I T I | S C | T G T S S D V G G Y - - - N Y V S |
| SEQ ID NO 33 | 4910 | D I / A L T Q P A - S V S G S | P G | Q S I T I | S C | T G T S S D V G G Y - - - N Y V S |
| SEQ ID NO 34 | 4921 | D I / A L T Q P A - S V S G S | P G | Q S I T I | S C | T G T S S D V G G Y - - - N Y V S |
| SEQ ID NO 35 | 4948 | D I / A L T Q P A - S V S G S | P G | Q S I T I | S C | T G T S S D V G G Y - - - N Y V S |
| SEQ ID NO 36 | 4470 | D I / A L T Q P A - S V S G S | P G | Q S I T I | S C | T G T S S D L G G Y - - - N Y V S |
| SEQ ID NO 37 | 4914 | D I / A L T Q P A - S V S G S | P G | Q S I T I | S C | T G T S S D L G G Y - - - N Y V S |
| SEQ ID NO 38 | 4920 | D I / A L T Q P A - S V S G S | P G | Q S I T I | S C | T G T S S D L G G Y - - - N Y V S |
| SEQ ID NO 39 | 4945 | D I / A L T Q P A - S V S G S | P G | Q S I T I | S C | T G T S S D L G G Y - - - N Y V S |
| SEQ ID NO 40 | 4952 | D I / A L T Q P A - S V S G S | P G | Q S I T I | S C | T G T S S D L G G Y - - - N Y V S |
| SEQ ID NO 41 | 4954 | D I / A L T Q P A - S V S G S | P G | Q S I T I | S C | T G T S S D L G G Y - - - N Y V S |
| SEQ ID NO 42 | VH5 | D I / V L T Q P P - S V S G A | P G | Q R V T I | S C | S G S S S N I G S - - - - N Y V S |
| SEQ ID NO 43 | 4516 | D I / V L T Q P P - S V S G A | P G | Q R V T I | S C | S G S S S N I G S - - - - S F V N |
| SEQ ID NO 44 | 4947 | D I / V L T Q P P - S V S G A | P G | Q R V T I | S C | S G S S S N I G S - - - - S F V N |

| | Framework 2 (5 6) | (7 8 9) | (40 1) | (2) | (3 4) | (5 6 7 8 9) | CDR 2 (50 1 2 3 4 5 6) |
|---|---|---|---|---|---|---|---|
| | | KpnI | | | XmaI | BbeI | |
| SEQ ID NO 31 | W Y | Q Q H | P G | K | A P | K L M I Y | D V S N R P S |
| SEQ ID NO 32 | W Y | Q Q H | P G | K | A P | K L M I H | D G S N R P S |
| SEQ ID NO 33 | W Y | Q Q H | P G | K | A P | K L M I H | D G S N R P S |
| SEQ ID NO 34 | W Y | Q Q H | P G | K | A P | K L M I H | D G S N R P S |
| SEQ ID NO 35 | W Y | Q Q H | P G | K | A P | K L M I H | D G S N R P S |
| SEQ ID NO 36 | W Y | Q Q H | P G | K | A P | K L M I Y | D V N N R P S |
| SEQ ID NO 37 | W Y | Q Q H | P G | K | A P | K L M I Y | D V N N R P S |
| SEQ ID NO 38 | W Y | Q Q H | P G | K | A P | K L M I Y | D V N N R P S |
| SEQ ID NO 39 | W Y | Q Q H | P G | K | A P | K L M I Y | D V N N R P S |
| SEQ ID NO 40 | W Y | Q Q H | P G | K | A P | K L M I Y | D V N N R P S |
| SEQ ID NO 41 | W Y | Q Q H | P G | K | A P | K L M I Y | D V N N R P S |
| SEQ ID NO 42 | W Y | Q Q L | P G | T | A P | K L L I Y | D N N Q R P S |
| SEQ ID NO 43 | W Y | Q Q L | P G | T | A P | K L L I G | N N S N R P S |
| SEQ ID NO 44 | W V | Q Q L | P G | T | A P | K L L I G | N N S N R P S |

| | Framework 3 (7) | (8 9 60 1 2 3) | (4 5) | (6 7 8 9 70 1 2 3 4 5 6 7 8 9 80) | (1 2) | (3 4 5 6 7 8) |
|---|---|---|---|---|---|---|
| | Bsu36I | | BamHI | | BbsI | |
| SEQ ID NO 31 | G | V S N R F S | G S | K S G N T A S L T I S G L Q A | E D | E A D Y Y C |
| SEQ ID NO 32 | G | V S N R F S | G S | K S G N T A S L T I S G L Q A | E D | E A D Y Y C |
| SEQ ID NO 33 | G | V S N R F S | G S | K S G N T A S L T I S G L Q A | E D | E A D Y Y C |
| SEQ ID NO 34 | G | V S N R F S | G S | K S G N T A S L T I S G L Q A | E D | E A D Y Y C |
| SEQ ID NO 35 | G | V S N R F S | G S | K S G N T A S L T I S G L Q A | E D | E A D Y Y C |
| SEQ ID NO 36 | G | V S N R F S | G S | K S G N T A S L T I S G L Q A | E D | E A D Y Y C |
| SEQ ID NO 37 | G | V S N R F S | G S | K S G N T A S L T I S G L Q A | E D | E A D Y Y C |
| SEQ ID NO 38 | G | V S N R F S | G S | K S G N T A S L T I S G L Q A | E D | E A D Y Y C |
| SEQ ID NO 39 | G | V S N R F S | G S | K S G N T A S L T I S G L Q A | E D | E A D Y Y C |
| SEQ ID NO 40 | G | V S N R F S | G S | K S G N T A S L T I S G L Q A | E D | E A D Y Y C |
| SEQ ID NO 41 | G | V S N R F S | G S | K S G N T A S L T I S G L Q A | E D | E A D Y Y C |
| SEQ ID NO 42 | G | V P D R F S | G S | K S G T S A S L A I T G L Q S | E D | E A D Y Y C |
| SEQ ID NO 43 | G | V P D R F S | G S | K S G T S A S L A I T G L Q S | E D | E A D Y Y C |
| SEQ ID NO 44 | G | V P D R F S | G S | K S G T S A S L A I T G L Q S | E D | E A D Y Y C |

TABLE 20C-continued

Alignment of the Amino Acid Sequences of Lambda Light Chain Variable Regions of anti-DKK1 Antibodies (SEQ ID NOs:)

| | CDR 3 | | | | | | | | | | Framework 4 | | | | | | | | | | | |
|---|---|---|---|---|---|---|---|---|---|---|---|---|---|---|---|---|---|---|---|---|---|---|
| | | 9 | | | | | | | | | | | | 10 | | | | | | | | |
| | 9 | 0 | 1 | 2 | 3 | 4 | 5 | A | B | 6 | 7 | 8 | 9 | 0 | 1 | 2 | 3 | 4 | 5 | 6 | 7 | 8 | 9 |
| | | | | | | | | | | | | | | | | | | HpaI | | | | MscI | |
| SEQ ID NO 31 | X | X | X | X | X | X | X | X | X | X | V | F | G | G | G | T | K | L | T | V | L | G | Q |
| SEQ ID NO 32 | S | T | W | D | M | T | V | D | - | F | V | F | G | G | G | T | K | L | T | V | L | G | Q |
| SEQ ID NO 33 | Q | S | W | D | V | S | P | I | T | A | V | F | G | G | G | T | K | L | T | V | L | G | Q |
| SEQ ID NO 34 | Q | T | W | A | T | S | P | L | S | S | V | F | G | G | G | T | K | L | T | V | L | G | Q |
| SEQ ID NO 35 | Q | T | W | D | S | L | S | F | - | F | V | F | G | G | G | T | K | L | T | V | L | G | Q |
| SEQ ID NO 36 | Q | S | Y | A | S | G | N | T | K | V | V | F | G | G | G | T | K | L | T | V | L | G | Q |
| SEQ ID NO 37 | Q | S | Y | T | Y | T | P | I | S | P | V | F | G | G | G | T | K | L | T | V | L | G | Q |
| SEQ ID NO 38 | Q | S | Y | A | S | G | N | T | K | V | V | F | G | G | G | T | K | L | T | V | L | G | Q |
| SEQ ID NO 39 | Q | T | Y | D | Q | I | K | L | S | A | V | F | G | G | G | T | K | L | T | V | L | G | Q |
| SEQ ID NO 40 | Q | S | Y | D | S | P | T | D | S | V | V | F | G | G | G | T | K | L | T | V | L | G | Q |
| SEQ ID NO 41 | Q | S | Y | A | S | G | N | T | K | V | V | F | G | G | G | T | K | L | T | V | L | G | Q |
| SEQ ID NO 42 | X | X | X | X | X | X | X | X | X | X | V | F | G | G | G | T | K | L | T | V | L | G | Q |
| SEQ ID NO 43 | A | S | F | D | M | G | S | P | N | V | V | F | G | G | G | T | K | L | T | V | L | G | Q |
| SEQ ID NO 44 | A | S | F | D | M | G | S | P | N | V | V | F | G | G | G | T | K | L | T | V | L | G | Q |

Consensus CDR sequences are provided at least in SEQ ID NOS:40-48 and in Table 11B. Additional consensus CDR sequences may be determined by one skilled in the art from the alignments in Tables 20A-20C using standard methods and methods provided herein.

EQUIVALENTS

From the foregoing detailed description of the specific embodiments of the invention, it should be apparent that novel antibodies and immunological fragments thereof have been described. Although particular embodiments have been disclosed herein in detail, this has been done by way of example for purposes of illustration only. In particular, it is contemplated by the inventor that various substitutions, alterations, and modifications may be made to the invention without departing from the spirit and scope of the invention.

What is claimed is:

1. A composition comprising:

(1) an isolated antibody or a functional fragment thereof comprising:

(a) CDR sequences of a variable heavy chain comprising: CDR1 with a sequence comprising amino acids 22 to 35 of SEQ ID NO: 11, CDR2 with a sequence comprising amino acids 47 to 66 of SEQ ID NO: 11, and CDR3 with a sequence comprising amino acids 99 to 105 of SEQ ID NO: 11, and (b) CDR sequences of a variable light chain comprising: CDR1 with a sequence comprising amino acids 23 to 36 of SEQ ID NO: 30, CDR2 with a sequence comprising amino acids 48 to 58 of SEQ ID NO: 30, and CDR3 with a sequence comprising amino acids 91 to 100 of SEQ ID NO: 30, wherein the antibody or functional fragment thereof specifically binds to human DKK1 and/or human DKK4; and (2) a bisphosphonate.

2. The composition according to claim 1, wherein binding to DKK1 or DKK4 is determined in at least one assay selected from: antagonism of Wnt-signaled transcription; electrochemiluminescence-based binding analysis; enzyme-linked immunosorbent assay binding; FMAT; SET; SPR; osteocalcin (OCN) serum concentration; osteoprotegrin (OPG) serum concentration; procollagen type 1 nitrogenous propeptide (P1NP) serum concentration, ALP production; TopFlash or ameliorating osteolysis.

3. The composition according to claim 1, wherein the isolated antibody or functional fragment is an isolated antibody.

4. The composition according to claim 1, which comprises a scaffold selected from an IgM and an IgG, wherein the IgG is selected from an IgG1, an IgG2, and IgG3 or an IgG4.

5. The composition according to claim 4, wherein the IgM or the IgG is selected from a polyclonal or monoclonal.

6. The composition according to claim 1, which is selected from a whole immunoglobulin or Fab fragment or scFv antibody fragment thereof, a heavy chain antibody, and an antigen-binding region thereof on a non-immunoglobulin scaffold.

7. The composition according to claim 1, wherein the bisphosphonate is zoledronic acid.

8. A composition comprising:

(1) an isolated antibody or a functional fragment thereof comprising:

(a) CDR sequences of a variable heavy chain comprising: CDR1 with a sequence comprising amino acids 22 to 35 of SEQ ID NO: 11, CDR2 with a sequence comprising amino acids 47 to 66 of SEQ ID NO: 11, and CDR3 with a sequence comprising amino acids 99 to 105 of SEQ ID NO: 11, and (b) CDR sequences of a variable light chain comprising: CDR1 with a sequence comprising amino acids 23 to 36 of SEQ ID NO: 30, CDR2 with a sequence comprising amino acids 48 to 58 of SEQ ID NO: 30, and CDR3 with a sequence comprising amino acids 91 to 100 of SEQ ID NO: 30, wherein the antibody or functional fragment thereof specifically binds to human DKK1 and/or human DKK4;

(2) a bisphosphonate; and (3) a pharmaceutically acceptable carrier or excipient.

9. The composition according to claim 8, wherein the isolated antibody or functional fragment is an isolated antibody.

10. The composition according to claim 8, which comprises a scaffold selected from an IgM and an IgG, wherein the IgG is selected from an IgG1, an IgG2, and IgG3 or an IgG4.

11. The composition according to claim 10, wherein the IgM or the IgG is selected from a polyclonal or monoclonal.

12. The composition according to claim 8, which is selected from a whole immunoglobulin or Fab fragment or scFv antibody fragment thereof, a heavy chain antibody, and an antigen-binding region thereof on a non-immunoglobulin scaffold.

13. The composition according to claim 8, wherein the bisphosphonate is zoledronic acid.

14. A composition comprising:

(1) an immunoconjugate comprising a first component which is an antibody or functional fragment thereof comprising:

(a) CDR sequences of a variable heavy chain comprising: CDR1 with a sequence comprising amino acids 22 to 35 of SEQ ID NO: 11, CDR2 with a sequence comprising amino acids 47 to 66 of SEQ ID NO: 11, and CDR3 with a sequence comprising amino acids 99 to 105 of SEQ ID NO: 11, and (b) CDR sequences of a variable light chain comprising: CDR1 with a sequence comprising amino acids 23 to 36 of SEQ ID NO: 30, CDR2 with a sequence comprising amino acids 48 to 58 of SEQ ID NO: 30, and CDR3 with a sequence comprising amino acids 91 to 100 of SEQ ID NO: 30, wherein the antibody or functional fragment thereof specifically binds to human DKK1 and/or human DKK4; and (2) a bisphosphonate.

15. The composition according to claim 14, wherein the isolated antibody or functional fragment is an isolated antibody.

16. The composition according to claim 14, which comprises a scaffold selected from an IgM and an IgG, wherein the IgG is selected from an IgG1, an IgG2, and IgG3 or an IgG4.

17. The composition according to claim 16, wherein the IgM or the IgG is selected from a polyclonal or monoclonal.

18. The composition according to claim 14, which is selected from a whole immunoglobulin or Fab fragment or scFv antibody fragment thereof, a heavy chain antibody, and an antigen-binding region thereof on a non-immunoglobulin scaffold.

19. The composition according to claim 14, wherein the bisphosphonate is zoledronic acid.

* * * * *